United States Patent
Eder et al.

(10) Patent No.: US 11,452,786 B2
(45) Date of Patent: Sep. 27, 2022

(54) DOUBLE-LABELED PROBE FOR MOLECULAR IMAGING AND USE THEREOF

(71) Applicants: Deutsches Krebsforschungszentrum, Heidelberg (DE); Ruprecht-Karls-Universitaet Heidelberg, Heidelberg (DE)

(72) Inventors: Ann-Christin Eder, Simonswald (DE); Matthias Eder, Simonswald (DE); Klaus Kopka, Dresden (DE); Martin Schaefer, Neckarsteinach (DE); Ulrike Bauder-Wuest, Schriesheim (DE); Uwe Haberkorn, Schwetzingen (DE)

(73) Assignees: Deutsches Krebsforschungszentrum, Heidelberg (DE); Ruprecht-Karls-Universitaet Heidelberg, Heidelberg (DE)

( * ) Notice: Subject to any disclaimer, the term of this patent is extended or adjusted under 35 U.S.C. 154(b) by 287 days.

(21) Appl. No.: 16/763,667

(22) PCT Filed: Nov. 12, 2018

(86) PCT No.: PCT/EP2018/080936
§ 371 (c)(1),
(2) Date: May 13, 2020

(87) PCT Pub. No.: WO2019/092242
PCT Pub. Date: May 16, 2019

(65) Prior Publication Data
US 2020/0368374 A1   Nov. 26, 2020

(30) Foreign Application Priority Data
Nov. 13, 2017  (EP) .................................... 17201264

(51) Int. Cl.
*A61K 51/04* (2006.01)
*C07D 403/14* (2006.01)

(52) U.S. Cl.
CPC ........ *A61K 51/0478* (2013.01); *C07D 403/14* (2013.01)

(58) Field of Classification Search
CPC .............................. A61K 51/04; C07D 403/14
See application file for complete search history.

(56) References Cited

U.S. PATENT DOCUMENTS

2015/0110715 A1 *  4/2015  Eder .................. A61K 51/0402
546/41

FOREIGN PATENT DOCUMENTS

| CN | 105636924 A | 6/2016 |
|---|---|---|
| WO | WO-2010/108125 A2 | 9/2010 |
| WO | WO-2015/055318 A1 | 4/2015 |
| WO | WO2019/101729 | 5/2019 |

OTHER PUBLICATIONS

U.S. Appl. No. 16/765,927, Eder et al.
Banerjee et al., "Sequential SPECT and optical imaging of experimental models of prostate cancer with a dual modality inhibitor of the prostate-specific membrane antigen," available in PMC Sep. 19, 2012, published in final edited form as: Angew Chem Int Ed Engl. 50(39):9167-9170 (2011) (7 pages).
Baranski et al., "Improving the imaging contrast of 68Ga-PSMA-11 by targeted linker design: charged spacer moieties enhance the pharmacokinetic properties," Bioconjug Chem. 28(9):2485-2492 (2017).
Eder et al., "68Ga-Complex Lipophilicity and the Targeting Property of a Urea-Based PSMA Inhibitor for PET Imaging," Bioconjugate Chem. 23(4):688-697 (2012).
Eder et al., "Pharmacokinetic properties of peptidic radiopharmaceuticals: reduced uptake of (EH)3-conjugates in important organs." J Nucl Med. 54(8):1327-1330 (2013).
Eder et al., "Tetrafluorophenolate of HBED-CC: a versatile conjugation agent for 68Ga-labeled small recombinant antibodies," Eur J Nucl Med Mol Imaging. 35(10):1878-1886 (2008).
International Search Report for European Patent Application No. PCT/EP2018/080936 dated Feb. 13, 2019 (4 pages).
Liolios et al., "Novel bispecific PSMA/GRPr targeting radioligands with optimized pharmacokinetics for improved PET imaging of prostate cancer." Bioconjug Chem. 27(3):737-751 (2016).

(Continued)

*Primary Examiner* — Michael G. Hartley
*Assistant Examiner* — Jagadishwar R Samala
(74) *Attorney, Agent, or Firm* — Clark & Elbing LLP

(57) ABSTRACT

The present invention relates to a compound or a pharmaceutically acceptable salt thereof having a chemical structure comprising: A compound or a pharmaceutically acceptable salt thereof of formula (I): (A)-$x_1$-(B)-$x_2$-(C), wherein (A) is at least one motif specifically binding to cell membranes of neoplastic cells; (B) at least one chelator moiety of radiometals; (C) a dye moiety; $x_1$ is a spacer covalently connecting (A) and (B); $x_2$ is a spacer or a chemical single bond connecting (B) and (C); wherein (C) has the formula wherein $R^1$ to $R^4$, $R^9$, a, b, Y and $X^1$ to $X^4$ have the meaning as indicated in the claims and description. The invention further relates to compositions comprising said compounds as well as a method for detecting neoplastic cells in a sample in vitro with the aid of the compounds or composition.

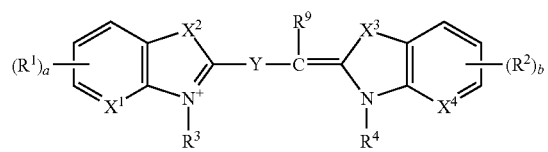

66 Claims, No Drawings
Specification includes a Sequence Listing.

(56) References Cited

OTHER PUBLICATIONS

Schäfer et al., "A dimerized urea-based inhibitor of the prostate-specific membrane antigen for 68Ga-PET imaging of prostate cancer." EJNMMI Res. 2(1):23 (2012) (11 pages).
Schuhmacher et al., "A new 68Ge/68Ga radioisotope generator system for production of 68Ga in dilute HCl*," Appl Radiat Isot. 32(1):31-36 (1981).
Seibold et al., "Bimodal imaging probes for combined PET and OI: recent developments and future directions for hybrid agent development," Biomed Res Int. 2014:153741 (2014) (14 pages).

* cited by examiner

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: linker sequence

<400> SEQUENCE: 1

Glu His Glu His Glu His
1               5
```

DOUBLE-LABELED PROBE FOR MOLECULAR IMAGING AND USE THEREOF

The present invention relates to a compound or a pharmaceutically acceptable salt thereof having a chemical structure of formula (I): (A)-$x_1$-(B)-$x_2$-(C), wherein (A) is at least one motif specifically binding to cell membranes of neoplastic cells; (B) at least one chelator moiety of radiometals; (C) a dye moiety; $x_1$ is a spacer covalently connecting (A) and (B); $x_2$ is a spacer or a chemical single bond connecting (B) and (C). The invention further relates to compositions comprising said compounds as well as a method for detecting neoplastic cells in a sample in vitro with the aid of the compounds or composition.

During the recent years, molecular imaging has gained increasing importance for the diagnosis of neoplasia, in particular cancer. Physicians thereby are able to obtain valuable information on the size, localization and shape of a neoplastic pitch.

In order to visualize neoplastic tissue in vivo, a variety of techniques has been developed. Exemplarily, magnetic resonance imaging (MRI), radiography (in particular computer tomography (CT)), fluorescence molecular tomography (FMT) and positron emission tomography (PET) are methods regularly used for localization of neoplasia today.

However, these methods still bear severe drawbacks. While MRI achieves a high resolution of visualization and enables measurements without any stain, MRI renders it comparably difficult, when not even impossible, to reliably distinguish between healthy and neoplastic tissue. Radiography, such CT, also achieves a comparably high resolution but, like MRI, fails to clearly distinguish between diseased and healthy tissue and, additionally, often requires unwanted high doses of contrast agents. FMT in turn enables detecting a specifically stained tissue but typically bears a poor resolution and allows only detections of neoplasia located nearby the outer surface of the patient's body and does, additionally, not enable the visualization of the surrounding tissue what renders it difficult for the examiner to infer diagnostic conclusions and to decide on further treatment strategies. PET enables the detection of neoplasia inside the entire patient's body, but merely depicts a neoplasm itself and does, like FMT, not show the localization of a neoplasm insight its tissue context.

MRI and PET are regularly combined with another, sometimes in a single apparatus, in order to enable distinct detection of neoplasia and the surrounding tissue. This enables the precise localization of a neoplasm in its tissue context and further shows the shape and size of a neoplasm.

However, apparatuses for MRI and PET are rather large size apparatuses comprising parts surrounding the patient's body and, thereby, impeding contemporary surgical interventions. When molecular imaging by means of MRT and/or PET has once been completed, the surgeon intending to remove the neoplastic tissue has to assess the position, size and shape of the neoplastic tissue in the patient's body by mentally projecting the image obtained from molecular imaging onto the patient's body. In other words, while performing the surgery, the surgeon is unable to visually see the neoplastic tissue in the patient' body because, often, the neoplastic tissue does not or merely slightly appears different from the surrounding non-neoplastic tissue. Exemplarily, lymph knots including neoplastic cells are typically not distinguishable from their healthy counterparts. The surgeon thus has to either remember the respective localization of the neoplastic tissue seen by molecular imaging before or, from time to time, has to digress his attention from the patient's body and turn to the results obtained from the molecular imaging in order to mentally project these results onto the patient's body.

This procedure has the major drawback that the surgeon can never be entirely sure to have removed the entire neoplastic tissue. Therefore, often rather large parts of the tissue are removed, including large amounts of healthy tissue. And, otherwise, often residual parts of neoplastic tissue still remain in the patient.

Improved radiopharmaceuticals are already proposed where compounds are described having a binding site to neoplastic cells and a chelator moiety, where the improvements lie in the combination of dual targeting radioligands using bispecific PSMA/GRPr addressing chemical moieties (C. Liolios et al., Bioconjugate Chemistry, 2016, 27, 737-751) or in a reduced uptake of peptidic radioligands in important organs (Eder et al., The Journal of Nuclear Medicine, 2013, 54 (8), 1327-1330). Improving the imaging contrast of $^{68}$Ga-PSMA-11 is described by A.-C. Baranski et al., Bioconjugate Chem. 2017, 28 (9), 1485-2492.

However there is still a need for improvement by further combining radiochemcials with binding site and chelator with a fluorescence chemical moiety.

Therefore, compounds bearing a cellular binding site binding to neoplastic cells (e.g., a prostate-specific membrane antigen (PSMA)), a fluorophore and a chelator, in particular an 1,4,7,10-tetraazacyclododecane-N,N',N'',N'''-tetraacetic acid (DOTA) chelator have been developed (Banerjee S R, Pullambhatla M, Byun Y, Nimmagadda S, Foss C, Green G, Fox J J, Lupold S E, Mease R, Pomper M G (2011); Sequential SPECT and optical imaging of experimental models of prostate cancer with a dual modality inhibitor of the prostate-specific membrane antigen. Angew Chem Int Ed Engl. 50(39):9167-9170; and WO 2010/108125). Herein, both the chelator as well as the fluorophore are each conjugated via independent spacers to a common molecular backbone that is conjugated to the cellular binding site.

This approach however bears the significant disadvantage that the flexibility in using various dyes is limited. Indeed, it has been found that using chelators like DOTA bears significant disadvantages such as diminished binding to a target structure when not combined with particular fluorophore structures such as IRDye800CW as used by Banerjee et al. Therefore, the structures known in the art are not used in a modular manner. In particular, the dyes conjugated therewith are not freely selectable and several fluorophors regularly and preferably used in the art are not usable with this strategy.

Further, cell-staining structures comprising a fluorophore, a chelator and a motif binding to cellular markers which are present in various cell populations are known (Seibold U, Wängler B, Schirrmacher R and Wängler C (2014); Bimodal imaging probes for combined PET and 01: recent developments and future directions for hybrid agent development. Biomed Res Int. 2014:153741. doi: 10.1155/2014/153741). These structures, however, do not comprise a motif specifically binding to cell membranes of neoplastic cells but rather to cellular structures present in various cell types including non-neoplastic physiological cells. Further, in these structures shown by Seibold et al., the binding site is not freely selectable in a modular manner, but rather integrated into the structure in a rather complex manner.

In view of the above, there is still an unmet need for compounds that enable in vivo molecular imaging in a patient as well as imaging during a surgery that are easy to synthesize in a modular manner and widely flexible with respect to the selection of the dye.

US 2015/110715 A1 describes compounds having a chemical structure comprising at least one motif (A) specifically binding to cell membranes of neoplastic cells, at least one chelator moiety (B) of radiometals; and at least one dye moiety (C). The chemical moieties (A), (B) and (C) can be directly connected to each other or by way of spacers. As one of the most important fluorescence chemical structures the afore-mentioned IRDye800CW and derivatives thereof are described.

Even though the radiochemical compounds described in US 2015/110715 A1 show good performance, there is still a need to further improve the properties of said compounds especially when IRDye800CW is used.

One of the important properties is given by the selectivity of such IRDye800CW comprising radiochemical compounds, i.e. the specific uptake in the tumor compared to a low uptake in important organs. This selectivity is expressed by the respective tumor-to-organ-ratio for a variety of different important organs.

Thus an object of the present invention is to provide IRDye800CW comprising compounds having improved tumor-to-organ-ratios.

This object is achieved by a compound or a pharmaceutically acceptable salt thereof of formula (I):

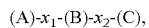

wherein
(A) is at least one motif specifically binding to cell membranes of neoplastic cells,
(B) at least one chelator moiety of radiometals;
(C) a dye moiety;
$x_1$ is a spacer covalently connecting (A) and (B);
$x_2$ is a spacer or a chemical single bond connecting (B) and (C);
wherein (C) has the formula

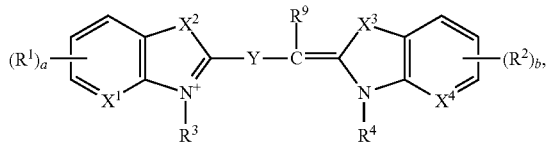

wherein
$X^1$ and $X^4$ are independently selected from the group consisting of —N=, —N($R^5$)=, and —C($R^6$)=;
$X^2$ and $X^3$ are independently selected from the group consisting of O, S, Se, N($R^5$), and C($R^6R^7$);
Y is a linker connecting the two moieties of (C) and permitting electron delocalization between said moieties, wherein Y optionally comprises a group (L-)$_c Z^0$;
a and b are independently selected from the group consisting of 1, 2, and 3;
each $R^1$ and each $R^2$ is independently (L-)$_c Z$, (L-)$_c Z^0$ or H; and two adjacent $R^1$ and/or two adjacent $R^2$ can also form an aromatic ring, which is optionally substituted with one or more (L)$_c Z$ or (L-)$_c Z^0$;
$R^3$, $R^4$, $R^5$, $R^6$, $R^7$, $R^9$ are independently selected from the group consisting of (L-)$_c Z$, (L-)$_c Z^0$, and H;
each c is independently 0, or 1;
each L is independently $T^1$, —O$T^1$-, —S$T^1$-, —C(O)$T^1$-, —C(O)O$T^1$-, —OC(O)$T^1$-, —C(O)NH$T^1$-, —NHC(O)$T^1$, or a $C_{1-10}$ alkylene group, which is optionally interrupted and/or terminated by one or more of —O—, —S—, —C(O)—, —C(O)O—, —OC(O)—, —C(O)NH—, —NHC(O)O—, and $T^1$;
$T^1$ is phenyl, naphthyl, indenyl, indanyl, tetralinyl, decalinyl, adamantyl, $C_{3-7}$ cycloalkyl, 3 to 7 membered heterocyclyl, or 7 to 11 membered heterobicyclyl,
wherein $T^1$ is optionally substituted with one or more substituents selected from the group consisting of halogen, CN, C(O)$R^8$, COO$R^8$, O$R^8$, C(O)N($R^8R^{8a}$), S(O)$_2$N($R^8R^{8a}$), S(O)N($R^8R^{8a}$), S(O)$_2R^8$, N($R^8$)S(O)$_2$N($R^{8a}R^{8b}$), S$R^8$, N($R^8R^{8a}$), NO$_2$, OC(O)$R^8$, N($R^8$)C(O)$R^{8a}$, N($R^8$)S(O)$_2R^{8a}$, N($R^8$)S(O)$R^{8a}$, N($R^8$)C(O)N($R^{8a}R^{8b}$), N($R^8$)C(O)O$R^{8a}$, OC(O)N($R^8R^{8a}$), oxo (=O), where the ring is at least partially saturated, or $C_{1-6}$ alkyl, wherein $C_{1-6}$ alkyl is optionally substituted with one or more halogen, which are the same or different;
each Z is independently H, halogen, CN, C(O)$R^8$, C(O)O$R^8$, C(O)O$^-$ O$R^8$, C(O)N($R^8R^{8a}$), S(O)$_2$O$R_8$, S(O)$_2$O$^-$, S(O)$_2$N($R^8R^{8a}$), S(O)N($R^8R^{8a}$), S(O)$_2R^8$, S(O)$R^8$, N($R^8$)S(O)$_2$N($R^{8a}R^{8b}$), S$R^8$, N($R^8R^{8a}$), NO$_2$; P(O)(O$R^8$)$_2$, P(O)(O$R^8$)O$^-$, OC(O)$R^8$, N($R^8$)C(O)$R^{8a}$, N($R^8$)S(O)$_2R^{8a}$, N($R^8$)S(O)$R^{8a}$, N($R^8$)C(O)N($R^{8a}R^{8b}$), N($R^8$)C(O)O$R^{8a}$, or OC(O)N($R^8R^{8a}$);
$R^8$, $R^{8a}$, $R^{8b}$ are independently selected from the group consisting of H, or $C_{1-6}$ alkyl, wherein $C_{1-6}$ alkyl is optionally substituted with one or more halogen, which are the same or different;
$Z^0$ is a chemical bond connecting (C) to $x_2$ or to (B) in case $x_2$ is a chemical single bond;
provided that one of $R^1$, $R^2$, $R^3$, $R^4$, $R^5$, $R^6$, $R^7$, $R^9$ is (L-)$_c Z^0$ or that Y comprises (L-)$_c Z^0$;
wherein $x_1$ comprises a group -AA-, wherein AA is an amino acid sequence of 4 to 8 (preferably 5 to 7, more preferably 6) naturally occurring amino acids and wherein at least two amino acids are histidine
and wherein any remaining positive or negative charge or charges are compensated by pharmaceutically acceptable negatively or positively charged counterion or counterions.

Surprisingly it has been found that dyes derived from dye moiety (C) as described herein and especially IRDye800CW comprising compounds with moieties (A), (B) and (C) described in the prior art have reduced tumor-to-organ-ratios compared to compounds with moieties (A) and (B) and the lower ratios can be improved by introduction of the amino acid sequence AA as part of the spacer $x_1$ between moieties (A) and (B).

The compound or pharmaceutically acceptable salt thereof of the present invention exemplarily enables a positron emission tomography (PET) scan as well as fluorescence imaging.

As used herein, the term "pharmaceutically acceptable salt" may be understood in the broadest sense as any charged form of the compound of the present invention. Depending on the chemical structure of the compound and on the environment it is dissolved in, the compound may, exemplarily, comprise one or more charged residue(s) selected from the group consisting of but not limited to carboxylate anion residue(s), primary ammonium cation(s), secondary ammonium cation residue(s), tertiary ammonium cation residue(s), primary phosphate anion residue(s), secondary phosphate anion residue(s), sulfate anion residue(s), sulfite anion residue(s) and an alkoxide residue(s). The counterions may be any ions known to be pharmaceutically acceptable in the art such as, e.g., acetate, fatty acid carboxylate, chloride, sodium ions, potassium ion, magnesium ion, calcium ion, aluminum ion, lithium ion, ammonium, phosphate, hydroxyl, proton and fluoride ion.

As used throughout the present invention, the term "motif" may be understood in the broadest sense as a molecular structure pattern that enables specific binding to cell membranes of neoplastic cells.

As used in the context of the present invention, the term "neoplastic cell" may be understood in the broadest sense as any cell that shows an abnormal growth and/or division rate, also including metaplastic and dysplastic cells. Typically, a neoplastic cell will tend to form a bulk of cells known as neoplasia. The growth of neoplastic cells typically is less or not coordinated with the normal tissues around it. The growth of a neoplastic cell preferably persists in the same excessive manner even after cessation of the stimuli. Neoplastic cells may form a benign neoplasia, a pre-malignant neoplasia (carcinoma in situ) or a malignant neoplasia (cancer). Neoplasia may also be characterized by the International Classification of Diseases Vol. 10 (ICD-10 nomenclature) in the version of 2013, i.e., as any pathological condition according to ICD-10 classes C00-D48. In the context of the present invention cancer also includes metastases.

Cancer in the sense of the present invention is any malignant neoplasia. Exemplarily, cancer may be a carcinoma (e.g., prostate carcinoma, breast carcinoma, lung carcinoma, pancreas carcinoma, liver carcinoma or colon carcinoma), a sarcoma (e.g. sarcoma in the bone, cartilage, fat and/or nerve tissue, or mesenchymal sarcoma), a lymphoma, a leukemia, germ cell (e.g., testicle or ovary cancer (seminoma and dysgerminoma, respectively)) or a blastoma e.g., liver blastoma).

The at least one motif (A) specifically binding to cell membranes of neoplastic cells enables the binding of its target structure present on the surface of neoplastic cells with a higher affinity compared to other molecular structures.

Target structure preferably is typical for neoplastic cells. Therefore, the target structure may preferably be found on the surface of neoplastic cells exclusively or at a higher local concentration compared to normal, i.e., non-neoplastic cells. Accordingly, the local concentration of the target structure recognized by the at least one motif (A) according to the present invention at the cell membrane of neoplastic cells preferably is at least 2 fold, more preferably at least 5 fold, even more preferably at least 10 fold, even more preferably at least 100 fold, even more preferably at least 500 fold higher compared to corresponding normal, i.e., non-neoplastic cells.

Preferably, the motif binds to its target structure on neoplastic cells with an at least 5 fold higher, more preferably at least 10 fold higher, even more preferably at least 20 fold higher, even more preferably at least 50 fold higher, in particular at least 100 fold higher affinity than to other molecular structures of the same charge and hydrophobicity in comparable chemical environments. Preferably, the motif binds to the target structure on cell membranes of neoplastic cells with a dissociation constant of not more than 10 µM, more preferably not more than 5 µM, even more preferably not more than 1 µM, even more preferably not more than 100 nM in particular not more than 50 nM.

The compound or pharmaceutically acceptable salt thereof of the present invention comprises a moiety (A) with at least one motif. Accordingly moiety (A) can represent one or more motifs. Exemplarily moiety (A) represents a chemical structure with one, two or three motifs. However, preferably (A) represents one motif.

Preferably, the motif comprises at least one naturally occurring amino acid moiety, more preferably at least two naturally occurring amino acid moieties.

As used throughout the present invention, the terms "moiety", "residue" and "rest" in the context of a chemical structure may be understood interchangeably in the broadest sense as a part of a molecule tightly bound to the other parts of the molecule, in particular via a covalent bond. Further, the terms "conjugated to" and "bound to" as used herein may be understood interchangeably.

Preferably, the motif comprises at least one non-proteinogenic amide bond, more preferably at least two non-proteinogenic amide bonds. More preferably, the motif comprises at least one naturally occurring amino acid moiety conjugated via a non-proteinogenic amide bond, even more preferably at least two naturally occurring amino acid moieties conjugated via non-proteinogenic amide bonds.

Preferably, the motif specifically binding to cell membranes of neoplastic cells comprises not more than 20 amino acid moieties, more preferably not more than ten amino acid moieties, even more preferably not more than five amino acid moieties, even more preferably not more than four amino acid moieties, in particular not more than three amino acid moieties.

Preferably, the motif further comprises at least one urea moiety, more preferably at least one urea moiety covalently bound to two amino acids via amide bond formation.

The at least one motif specifically binding to cell membranes of neoplastic cells (A) is covalently linked with the at least one chelator moiety of radiometals (B) via spacer $x_1$. In this context, preferably, the spacer $x_1$ is of not more than 5 nm in length, preferably of not more than 2 nm in length, in particular of not more than 1 nm in length. The motif may preferably be conjugated to chelator moiety of radiometals (B) via the epsilon amino group of a lysine moiety.

The term "chelator moiety" as used in the context of the present invention may be understood in the broadest sense as any moiety that is able to form a complex with a radiometal under suitable conditions. Herein, the terms "chelator moiety", "chelant", "chelating moiety", "sequestering moiety" and "complexing moiety" may be understood interchangeably. The chelator moiety is preferably an organic moiety. Complexing by chelation preferably involves the formation or presence of two or more separate coordinate bonds between a polydentate (multiple bonded) ligand and a single central radiometal. The common definition of the International Union of Pure and Applied Chemistry (IUPAC) on chelation, interpreted in its broadest sense, may also be noted. Chelator moieties as used herein will typically bear at least two heteroatoms enabling an interaction with a radiometal. Preferably, the chelator moiety will have at least three, in particular at least four heteroatoms enabling an interaction with a radiometal.

A "radiometal" as used in the context of the present invention may be understood in the broadest sense as any radioactive metal or radioactive metal ion, i.e., a metal or metal ion that emits radioactive emission. It may be a metal or metal ion that is typically radioactive or a radioactive isotope of a metal that also has non-radioactive isotopes. Exemplarily, a radiometal may be a radioactive isotope of gallium (Ga) (e.g., $^{67}$Ga, $^{68}$Ga), copper (e.g., $^{64}$Cu, $^{67}$Cu), iron (e.g., $^{59}$Fe), zirconium (e.g., $^{89}$Zr), scandium (e.g., $^{44}$Sc), indium (e.g., $^{111}$In), yttrium (e.g., $^{90}$Y) rubidium (e.g., $^{82}$Rb), cobalt (e.g., $^{60}$Co), lutetium (e.g., $^{177}$Lu), gadolinium (e.g., $^{153}$Gd, $^{155}$Gd, $^{157}$Gd), bismuth (e.g., $^{213}$Bi), strontium (e.g., $^{90}$Sr), actinium (e.g., $^{225}$Ac) or technetium (e.g., $^{99m}$Tc). Preferably, the radiometal is a radioactive isotope of $^{67}$Ga, $^{68}$Ga, $^{111}$In, $^{90}$Y, $^{177}$Lu, $^{64}$Cu, $^{67}$Cu, $^{153}$Gd, $^{155}$Gd, $^{157}$Gd, $^{89}$Zr, $^{44}$Sc, $^{99m}$Tc, $^{213}$Bi, $^{225}$Ac, $^{59}$Fe or $^{82}$Rb, more preferably $^{68}$Ga, $^{64}$Cu, $^{89}$Zr, $^{44}$Sc, or $^{82}$Rb, even more preferably $^{68}$Ga or $^{64}$Cu, in particular $^{68}$Ga. The person skilled in the art will know several examples for chelator moieties suitable for complexing each of the aforementioned radiometals and may select the chelator moiety accordingly. Exemplarily, a chelator moiety suitable for complexing $^{99m}$Tc or $^{82}$Rb, may or may not differ from that suitable for complexing $^{68}$Ga or $^{64}$Cu.

Preferably, the radiometal is such that has a half-life of no longer than four days, more preferably of no longer than one day, even more preferably no longer than 12 h, even more preferably, not more than 6 h, even more preferably not more than 3 h, even more preferably not more than 2.5 h, even more preferably not more than 120 min, even more preferably not more than 100 min, even more preferably not more than 80 min, in particular not more than 70 min.

The radiometal may be obtained from any source suitable for this purpose. The radiometal may be obtained and isolated from nature or artificially be generated such as, e.g., $^{68}$Ga from a gallium-68-generator. The person skilled in the art will know how to obtain the respective radiometal.

The compound or pharmaceutically acceptable salt thereof of the present invention comprises a moiety (B) with at least one chelator moiety of radiometals.

Accordingly moiety (B) can represent one or more chelators. Exemplarily moiety (B) represents a chemical structure with one, two or three chelators. However, preferably (B) represents one chelator. Moiety (B) is connected to moiety (A) via spacer $x_1$ as outlined herein.

The compound or pharmaceutically acceptable salt thereof of the present invention comprises a dye moiety (C). Moiety (C) is connected to (B) via $x_2$, which represents a spacer or a chemical single bond.

The moiety (C) has the formula

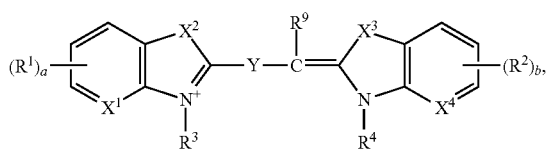

wherein
$X^1$ and $X^4$ are independently selected from the group consisting of —N=, —N($R^5$)=, and —C($R^6$)=;
$X^2$ and $X^3$ are independently selected from the group consisting of O, S, Se, N($R^5$), and C($R^6R^7$);
Y is a linker connecting the two moieties of (C) and permitting electron delocalization between said moieties, wherein Y optionally comprises a group (L-)$_c Z^0$;
a and b are independently selected from the group consisting of 1, 2, and 3;
each $R^1$ and each $R^2$ is independently (L-)$_c Z$, (L-)$_c Z^0$ or H; and two adjacent $R^1$ and/or two adjacent $R^2$ can also form an aromatic ring, which is optionally substituted with one or more (L-)$_c Z$ or (L-)$_c Z^0$;
$R^3$, $R^4$, $R^5$, $R^6$, $R^7$, $R^9$ are independently selected from the group consisting of (L-)$_c Z$, (L-)$_c Z^0$, and H;
each c is independently 0, or 1;
each L is independently $T^1$, —O$T^1$-, —S$T^1$-, —C(O)$T^1$-, —C(O)O$T^1$-, —OC(O)$T^1$-, —C(O)NH$T^1$-, —NHC(O)$T^1$, or a $C_{1-10}$ alkylene group, which is optionally interrupted and/or terminated by one or more of —O—, —S—, —C(O)—, —C(O)O—, —OC(O)—, —C(O)NH—, —NHC(O)O—, and $T^1$;
$T^1$ is phenyl, naphthyl, indenyl, indanyl, tetralinyl, decalinyl, adamantyl, $C_{3-7}$ cycloalkyl, 3 to 7 membered heterocyclyl, or 7 to 11 membered heterobicyclyl, wherein $T^1$ is optionally substituted with one or more substituents selected from the group consisting of halogen, CN, C(O)$R^8$, COO$R^8$, O$R^8$, C(O)N($R^8R^{8a}$), S(O)$_2$N($R^8R^{8a}$), S(O)N($R^8R^{8a}$), S(O)$_2R^8$, N($R^8$)S(O)$_2$N($R^{8a}R^{8b}$), S$R^8$, N($R^8R^{8a}$), NO$_2$; OC(O)$R^8$, N($R^8$)C(O)$R^{8a}$, N($R^8$)S(O)$_2R^{8a}$, N($R^8$)S(O)$R^{8a}$, N($R^8$)C(O)N($R^{8a}R^{8b}$), N($R^8$)C(O)O$R^{8a}$, OC(O)N($R^8R^{8a}$), oxo (=O), where the ring is at least partially saturated, or $C_{1-6}$ alkyl, wherein $C_{1-8}$ alkyl is optionally substituted with one or more halogen, which are the same or different;
each Z is independently H, halogen, CN, C(O)$R^8$, C(O)O$R^8$, C(O)O$^-$ O$R^8$, C(O)N($R^8R^{8a}$), S(O)$_2$O$R_8$, S(O)$_2$O$^-$, S(O)$_2$N($R^8R^{8a}$), S(O)N($R^8R^{8a}$), S(O)$_2R^8$, S(O)$R^8$, N($R^8$)S(O)$_2$N($R^{8a}R^{8b}$), S$R^8$, N($R^8R^{8a}$), NO$_2$; P(O)(O$R^8$)$_2$, P(O)(O$R^8$)O$^-$, OC(O)$R^8$, N($R^8$)C(O)$R^{8a}$, N($R^8$)S(O)$_2R^{8a}$, N($R^8$)S(O)$R^{8a}$, N($R^8$)C(O)N($R^{8a}R^{8b}$), N($R^8$)C(O)O$R^{8a}$, or OC(O)N($R^8R^{8a}$);
$R^8$, $R^{8a}$, $R^{8b}$ are independently selected from the group consisting of H, or $C_{1-6}$ alkyl, wherein $C_{1-8}$ alkyl is optionally substituted with one or more halogen, which are the same or different;
$Z^0$ is a chemical bond connecting (C) to $x_2$ or to (B) in case $x_2$ is a chemical single bond;
provided that one of $R^1$, $R^2$, $R^3$, $R^4$, $R^5$, $R^6$, $R^7$, $R^9$ is (L-)$_c Z^0$ or that Y comprises (L-)$_c Z^0$.

The term "optionally substituted" means unsubstituted or substituted. Generally—but not limited to—, "one or more substituents" means one, two or three, preferably one or two substituents and more preferably one substituent. Generally these substituents can be the same or different.

"Alkyl" means a straight-chain or branched hydrocarbon chain. Each hydrogen of an alkyl carbon may be replaced by a substituent as further specified herein.

As used throughout the present application, the terms "alkyl", "alkyl residue" and "alkyl group" and "alkyl moiety" may be understood as a straight-chain or branched saturated hydrocarbon chain. "Straight-chain" may be also designated as "unbranched" or "linear". Preferably, the alkyl is a straight chain.

As used throughout the present application, the term "alkylene" means a straight-chain or branched saturated hydrocarbon chain wherein two moieties of a molecule are linked by the alkylene residue. "Straight-chain" may be also designated as "unbranched" or "linear". Each hydrogen of an alkylene carbon may or may not be replaced by a substituent (i.e., may be substituted or unsubstituted) as further specified herein).

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a $C_{1-4}$ alkyl carbon may be replaced by a substituent as further specified herein.

"$C_{1-8}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a $C_{1-8}$ alkyl carbon may be replaced by a substituent as further specified herein.

"$C_{1-8}$ alkylene residue" means an alkylene chain having 1-8 carbon atoms, e.g. —$CH_2$—, —$CH_2$—$CH_2$—, —CH($CH_3$)—, —$CH_2$—$CH_2$—$CH_2$—, —CH($C_2H_5$)—, —C($CH_3$)$_2$—, —$CH_2$—C($CH_3$)$_2$—, —C($CH_2$—$CH_3$)$_2$—, —CH($CH_2$—$CH_3$)—, —$CH_2$—CH($CH_3$)($CH_2$—$CH_3$)—, —CH($CH_3$)($CH_2$—$CH_3$)—, —($CH_2$)$_4$—, —($CH_2$)$_5$—, —($CH_2$)$_6$—, —($CH_2$)$_7$—, —($CH_2$)$_8$—, etc., when two moieties of a molecule are linked by the alkylene group. The terms "$C_{4-8}$ alkylene" and "$C_6$ alkylene" are defined accordingly. The terms "$C_{3-7}$ alkylene" and "$C_5$ ($C_4$) alkylene" are defined accordingly.

The term "$C_{1-10}$ alkylene group" means a bivalent straight-chain or branched hydrocarbon chain having 1 to 10 carbon atoms. Each hydrogen of an alkyl carbon may be replaced by a substituent as further specified herein. Examples are methylene (—$CH_2$—) —$CH_2$—$CH_2$—, —CH($CH_3$)—, —$CH_2$—$CH_2$—$CH_2$—, —CH($C_2H_5$)—, —C($CH_3$)$_2$—. Each hydrogen of a $C_{1-10}$ alkylene group carbon may be replaced by a substituent as further specified herein.

Accordingly, "$C_{1-10}$ alkylene residue" means an alkylene chain having 1-10 carbon atoms when two moieties of a molecule are linked by the alkylene group. Preferably, but not necessarily, the $C_{1-10}$ alkylene residue in the context of residue f of the spacer y is a straight-chain, i.e., unbranched, $C_{1-10}$ alkylene residue, in which optionally one or more hydrogen(s) are substituted and/or in which optionally one or more —$CH_2$— moieties may be replaced by —O— or NH—.

The expression "one or more —$CH_2$— moieties may optionally be replaced by" means that the indicated number of $CH_2$ groups can be replaced by an atom or group specified herein. In addition one or more hydrogens as specified herein can be replaced by a substituent $C_{1-10}$ alkylene group "optionally interrupted and/or terminated" means that the alkylene chain is interrupted between two carbon atoms by an atom or a chemical group as specified herein or the alkylene group is terminated by said atom or group following the carbon at least at one end of the alkylene chain or the alkylene chain is both, interrupted and terminated or the alkylene chain is neither interrupted nor terminated. As an example without being bound to that example a $C_3$ alkylene group which is optionally interrupted and/or terminated with one or more X may have the sequence C—C—C, C—C—C—X, X—C—C—C, X—C—C—C—X, C—X—C—C, C—C—X—C, C—X—C—X—C, X—C—C—X—C, X—C—X—C—X—C, X—C—X—C—C—X, X—C—X—C—X—C—X.

The term "carbocycle" refers to a partly or fully saturated or aromatic carbocyclic mono-, bi- or tricyclic fused or unfused ring system. This includes phenyl and $C_{3-7}$ cycloalkyl rings. Preferred carbocycles having 5, 6 or 7 carbon atoms are cyclopentene, cyclohexene, phenyl, cycloheptane, especially cyclohexane.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Preferably, cycloalkyl refers to cyclopropyl, cyclobutyl, cyclopentyl, cyclohexyl, or cycloheptyl. Each hydrogen of a cycloalkyl carbon may be replaced by a substituent as further specified herein. The term "$C_{3-5}$ cycloalkyl" or "$C_{3-5}$ cycloalkyl ring" is defined accordingly.

"Halogen" means fluoro, chloro, bromo or iodo. It is generally preferred that halogen is fluoro or chloro.

Within the meaning of the present invention the term "aromatic ring" means a carbocyclic or heterocyclic aromatic ring. Examples are benzene, naphthalene, 5 to 6 membered aromatic heterocycle and 9 to 11 membered aromatic heterobicyclyl.

"3 to 7 membered heterocyclyl" or "3 to 7 membered heterocycle" means a ring with 3, 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 3 to 7 membered heterocycle are aziridine, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "4 to 7 membered heterocyclyl" or "4 to 7 membered heterocycle" is defined accordingly. The term "5 to 6 membered heterocyclyl" or "5 to 6 membered heterocycle" is defined accordingly.

"5 to 6 membered aromatic heterocyclyl" or "5 to 6 membered aromatic heterocycle" means a heterocycle derived from cyclopentadienyl or benzene, where at least one carbon atom is replaced by a heteroatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, triazole, tetrazole, pyridine, pyrimidine, pyridazine, pyrazine, triazine.

"5 membered aromatic heterocyclyl" or "5 membered aromatic heterocycle" means a heterocycle derived from cyclopentadienyl, where at least one carbon atom is replaced by a heteroatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, triazole, tetrazole.

"7 to 11 membered heterobicyclyl" or "7 to 11 membered heterobicycle" means a heterocyclic system of two rings with 7 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 7 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 7 to 11 membered heterobicycle also includes spiro structures of two rings like 6-oxa-2-azaspiro[3,4]octane, 2-oxa-6-azaspiro[3.3]heptan-6-yl or 2,6-diazaspiro[3.3]heptan-6-yl or bridged heterocycles like 8-aza-bicyclo[3.2.1]octane or 2,5-diazabicyclo[2.2.2]octan-2-yl or 3,8-diazabicyclo[3.2.1]octane.

"9 to 11 membered aromatic heterobicyclyl" or "9 to 11 membered aromatic heterobicycle" means a heterocyclic system of two rings, wherein at least one ring is aromatic and wherein the heterocyclic ring system has 9 to 11 ring atoms, where two ring atoms are shared by both rings and that may contain up to the maximum number of double bonds (fully or partially aromatic) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered aromatic heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, tetrahydroquinoline, isoquinoline, tetrahydroisoquinoline, dihydroisoquinoline, benzazepine, purine or pteridine. The terms "9 to 10 membered aromatic heterobicyclyl" or "9 to 10 membered aromatic heterobicycle" are defined accordingly.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

Where tautomerism, like e.g. keto-enol tautomerism, of compounds of formula (I) may occur, the individual forms, like e.g. the keto and enol form, are comprised separately and together as mixtures in any ratio. Same applies for stereoisomers, like e.g. enantiomers, cis/trans isomers, conformers and the like.

Especially, when enantiomeric or diastereomeric forms are given in a compound according to formula (I) each pure form separately and any mixture of at least two of the pure forms in any ratio is comprised by formula (I) and is a subject of the present invention.

Isotopic labeled compounds of formula (I) are also within the scope of the present invention. Methods for isotope labeling are known in the art. Preferred isotopes are those of the elements H, C, N, O and S. Solvates of compounds of formula (I) are also within the scope of the present invention.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials, reagents and/or catalysts.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

It is to be understood that the compounds or pharmaceutically acceptable salts thereof of the present invention show one or more charged functional groups, wherein each negative charge is compensated by a positive charge so that the molecule is neutral. Intramolecular compensation is possible as well as by other ions in form of inner and outer salts. Suitable counterions are those cited above. Accordingly, in the formulas of the present invention any remaining positive or negative charge or charges are compensated by pharmaceutically acceptable negatively or positively charged counterion or counterions. Likewise any protonated form may be partly or fully deprotonated with appropriate counterion(s).

A counterion as used herein may be any pharmaceutically acceptable ion that is suitable for neutralizing the charge of a residue or the compound of the present invention. It will be understood that a single counterion does not necessarily has the same valency as a charged residue or a charged compound of the present invention. Also two or more counterions may be used to neutralize a compound bearing a charge of higher charge valency than +1 or −1. Likewise, the other way round, also a single counterion bearing a charge of higher valency than +1 or −1 may be used to neutralize more than one compound. Preferably, the counterion is well-soluble in aqueous liquids.

A pharmaceutically acceptable negatively charged counterion $X^−$ in the context of the present invention may have any charge valency. Therefore, $X^−$ may exemplarily have a charge of −1, −2, −3 or −4, preferably of −1 or −2. Charge may also optionally depend on ion strength and pH, respectively. $X^−$ may be any pharmaceutically acceptable negatively charged ion. Preferably, the ion is such well-soluble in aqueous liquids. Exemplarily, $X^−$ may be selected from the group consisting of a halide anion (e.g., F⁻ or Cl⁻), acetate, phosphate, hydrogen phosphate, and a pharmaceutically acceptable carboxylate (e.g., a fatty acid carboxylate). Further, it will be understood that the counterion typically depends on the surrounding liquids such as those comprised in the buffer the compound is dissolved in and the body fluids after injection in vivo. In vivo, extracellularly, one of the main, but not sole negatively charged counterions is Cl⁻.

As used in the context of the present invention, the terms "dye moiety", "label" and "stain" may be understood interchangeably in the broadest sense as any moiety with the above formula that provides a visible stain. Preferably, the dye moiety may be a fluorescent dye moiety and/or a chromatic moiety, particularly preferably the dye moiety is a fluorescent dye moiety.

A fluorescent dye moiety as used herein may be understood in the broadest sense as any dye moiety enabling fluorescence detection. Preferably, such fluorescence detection is in a range of from 400 to 1000 nm, i.e. in the visible spectrum and in the Near Infrared (NIR) spectrum, in particular in a range of from 400 to 800 nm, i.e. in the visible spectrum. Preferably, the fluorescence signal emitted by the fluorescence dye moiety is well-distinguishable from the autofluorescence of the neoplasia and the surrounding tissue. Numerous fluorescent dye moieties are known in the art, and will be readily apparent to one of ordinary skill. Many fluorescent dyes are commercially available with activated groups used to react with protein sidechains or other compounds such as precursor compounds for the preparation of a compound of the present invention.

Additionally or alternatively, the dye moiety may also be chromatic, i.e., provoke a colour perception when illuminated by any light. Such chromatic effect may be provoked by absorbing light of one or more particular wavelength range(s) in the visible range (i.e., in range(s) from approximately 400 nm to approximately 800 nm) and/or by emitting light of one or more particular wavelength range(s) in the visible range. Preferably, the colour is different from the neoplasia and the surrounding tissue intended to be examined. Therefore, a dye moiety, when not intended for fluorescence detection, is preferably not red or brown, but rather preferably blue or green. When the dye moiety is intended for fluorescence detection, the difference in colour will typically play a minor role as long as the fluorescence is detectable over the autofluorescence background. Preferably, the chromatic dye moiety in the context of the present invention is a small-molecule dye, i.e., a dye moiety having a molecular weight (MW) of not more than 1000 Da, preferably not more than 750 Da, in particular nor more than 500 Da.

The dye moiety (C) is covalently linked with the at least one motif specifically binding to cell membranes of neoplastic cells (A) and the at least one chelator moiety of radiometals (B) via (A)-$x_1$-(B)-$x_2$-(C). Such covalent conjugation to a chelator moiety of radiometals (B) may be the formation of a covalent bond directly between the dye moiety (C) and the chelator moiety of radiometals (B) or may be covalent linkage via a spacer, preferably via spacer. Preferably, a spacer is of not more than 5 nm in length, preferably of not more than 2 nm in length, in particular of not more than 1 nm in length.

Accordingly, the molecular distance between the motif specifically binding to cell membranes of neoplastic cells (A) and the dye moiety (C) is preferably not longer than 20 nm, more preferably not longer than 10 nm, in particular not longer than 5 nm.

This may, depending on the chemical properties of the fluorescence dye moiety/moieties in the compound of the present invention and the presence of fluorophore(s) and/or quenchers on the surface of the target cells, i.e., the cell membranes of the respective neoplastic cells, also enable to observe effects such as fluorescence energy transfer (FRET) and/or fluorescence quenching upon binding of the compound according to the present invention to said cell membranes. Additionally or alternatively, the presence of the fluorescence dye moiety/moieties also enables to conduct further examination methods based on fluorescence such as, e.g., fluorescence recovery after photobleaching (FRAP), fluorescence loss in photobleaching (FLIP). These methods may provide information on the mobility of the compound or salt thereof bound to or associated with the cell membranes of a neoplastic cell.

Preferably, the compound or pharmaceutically acceptable salt thereof according to the present invention has a molecular weight (MW) of not more than 10 kDa, more preferably not more than 5 kDa, even more preferably not more than 3.5 kDa, even more preferably not more than 3 kDa, in particular not more than 2.5 kDa.

As mentioned above, motif specifically binding to cell membranes of neoplastic cells (A) may bind to any molecular structures typically found on neoplastic cells and may have any molecular structure.

In a preferred embodiment, the motif specifically binding to cell membranes of neoplastic cells (A) is a motif specifically binding to cell membranes of cancerous cells, preferably wherein said motif comprises a prostate-specific membrane antigen (PSMA) binding motif.

Herein, the terms "prostate-specific membrane antigen", "prostate-specific membrane antigen binding motif" and "PSMA binding motif", may be understood interchangeably.

In a more preferred embodiment, the motif specifically binding to cell membranes of neoplastic cells (A) is a PSMA binding motif having the following structure:

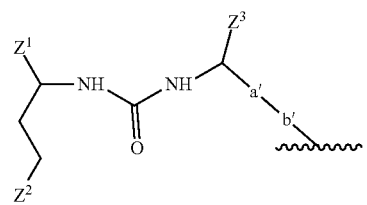

wherein $Z^1$, $Z^2$ and $Z^3$ are each independently from another selected from the group consisting of —C(O)OR$^{1a}$, —SO$_2$R$^{1a}$, —SO$_3$R$^{1a}$, —SO$_4$R$^{1a}$, —PO$_2$R$^{1a}$, —PO$_3$R$^{1a}$, and —PO$_4$R$^{1a}$R$^{2a}$, wherein R$^{1a}$ and R$^{2a}$ are independently from another H or a C$_{1-4}$-alkyl residue (preferably the same and more preferably H);

wherein a' represents a —[CH$_2$]$_o$— residue, wherein o is an integer from 1 to 4, preferably wherein o is 3 or 4, in particular wherein o is 4.

wherein b' represents a residue selected from the group consisting of —NH—, —C(O)— and —O—, in particular wherein b' is —NH—; and wherein the wavy line indicates the conjugation site to the chelator moiety of radiometals (B), conjugated via a spacer molecule $x_1$.

Preferably, $Z^1$, $Z^2$, $Z^3$ are the same and more preferably, $Z^1$, $Z^2$, $Z^3$ are —C(O)OR$^{1a}$.

In a particularly preferred embodiment, the motif specifically binding to cell membranes of neoplastic cells (A) is a PSMA binding motif having the following structure:

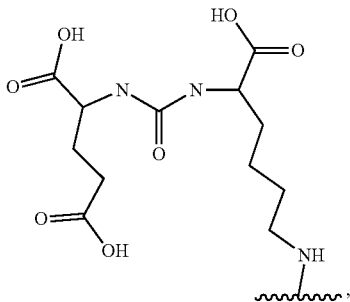 [SMILES: *NCCCCC(NC(=O)NC(CCC(=O)O)C(=O)O)C(=O)O]

wherein the wavy line indicates the conjugation site to the chelator moiety of radiometals (B), conjugated via the spacer molecule $x_1$.

The spacers $x_1$ and $x_2$ may be spacers with not more than 5 nm in length, preferably of not more than 2 nm in length, in particular of not more than 1 nm in length.

The spacer $x_1$ comprises a group -AA-, wherein AA is an amino acid sequence of 4 to 8 (preferably 5 to 7, more preferably 6) naturally occurring amino acids and wherein at least two amino acids are histidine.

The term "naturally occurring amino acids" refer to an amino acid selected from the group consisting of:

| | |
|---|---|
| Ala | Alanine |
| Arg | Arginine |
| Asn | Asparagine |
| Asp | Aspartic acid |
| Cys | Cysteine |
| Gln | Glutamine |
| Glu | Glutamic acid |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

The naturally occurring amino acids may be present in racemic, D- or L-form, preferably in L-form.

Preferably, AA comprises three histidine amino acids. Preferably, AA consists of histidine and glutamic acid. Preferably, AA is represented by the formula -His-Glu-His-Glu-His-Glu-. Accordingly the compound or pharmaceutically acceptable salt thereof may comprise the amino acid sequence -His-Glu-His-Glu-His-Glu-bound to the rest of the molecule via C- and N-terminus and is thus derived from the following free polypeptide sequence:
SEQ ID NO:1
EHEHEH.

Preferably, the C-terminus or the N-terminus, preferably the C-terminus, of AA forms an amide bond with (A), preferably with histidine comprised in AA.

Accordingly, in a preferred embodiment the (A)-$x_1$ comprises the following partial structure with histidine as part of AA and $x_1$ bound to (A):

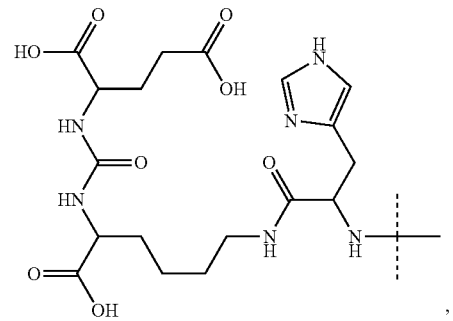

wherein the dashed line indicates the attachment to the rest of AA comprised in $x_1$.

In a preferred embodiment, the spacer $x_1$ bears the following structure:

-AA-[b''-e-b''']$_n$-b''''-$d^1$-, wherein b'' is —C(O)— or —N(H)—, preferably forming an amide bond with AA;

wherein e represents a residue selected from the group consisting of an $C_{1-8}$-alkylene wherein one or more —CH$_2$— moieties may optionally be replaced by one or more —O—, —S—, —C(O)NH— —C(O)N($C_{1-6}$ alkyl), —C(O)O—, succinimide, triazole.

wherein b''' is selected from the group consisting of —NH—, and —C(O)—;

wherein b'''' is selected from the group consisting of —C(O)—, and —NH—;

and wherein b''' and b'''' or a terminus of AA, preferably the N-terminus of AA, and b'''' together form an amide group;

wherein $d^1$ is —[CH$_2$]$_p$—, wherein p is 1 or 2, in particular 2; and wherein n is 0 or 1, preferably 0.

Preferably, b'' is C(O)

Preferably e is without any replacement, or with one, two or three replacements, preferably one replacement, especially with triazole.

preferably wherein e is a residue selected from the group consisting of an unsubstituted $C_{1-8}$-alkylene, $C_{1-8}$ alkylene, where one —CH$_2$— is replaced by triazole, $C_{4-8}$ alkylene (especially $C_6$ alkylene), where one —CH$_2$— is replaced by triazole, —CH$_2$—(O—CH$_2$—CH$_2$)$_2$—CH$_2$—, —(CH$_2$)$_2$—(O—CH$_2$—CH$_2$)$_2$—, —(CH$_2$)$_3$—O—CH$_2$—CH$_2$—O—CH$_2$—, —CH$_2$—O—(CH$_2$)$_6$—, —(CH$_2$)$_2$—O—(CH$_2$)$_5$—, —(CH$_2$)$_3$—O—(CH$_2$)$_4$—, —(CH$_2$)$_4$—O—(CH$_2$)$_3$—, —(CH$_2$)$_5$—O—(CH$_2$)$_2$—, —(CH$_2$)$_6$—O—CH$_2$—, —CH$_2$—(O—CH$_2$—CH$_2$)$_2$—, —(CH)$_2$—O—CH$_2$—CH$_2$—O—CH$_2$—, —CH$_2$—O—(CH$_2$)$_5$—, —(CH$_2$)$_2$—O—(CH$_2$)$_4$—, —(CH$_2$)$_3$—O—(CH$_2$)$_3$—, —(CH$_2$)$_4$—O—(CH$_2$)$_2$—, —(CH$_2$)$_5$—O—CH$_2$—, —CH$_2$—O—CH$_2$—CH$_2$—O—CH$_2$—, —CH$_2$—O—(CH$_2$)$_4$—, —(CH$_2$)$_2$—O—(CH$_2$)$_3$—, —(CH$_2$)$_3$—O—(CH$_2$)$_2$—, —(CH$_2$)$_4$—O—CH$_2$—, —CH$_2$—O—(CH$_2$)$_3$—, —(CH$_2$)$_2$—O—(CH$_2$)$_2$—, —(CH$_2$)$_3$—O—CH$_2$—, —CH$_2$—O—(CH$_2$)$_2$—, —(CH$_2$)$_2$—O—CH$_2$—, and —CH$_2$—O—CH$_2$— in particular a residue selected from the group consisting of a butylene residue, a pentylene residue, a hexylene residue, or $C_{4-8}$ alkylene, where one —CH$_2$— is replaced by triazole;

In particular e is represented by the structure

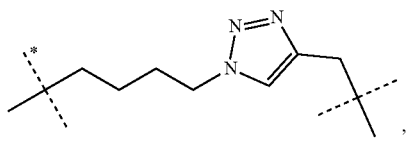

wherein the dashed line with the star represents attachment to b" and the dashed line without star represents attachment to b'".

Preferably, b" is —NH—. Preferably b'" is —C(O)—. Preferably n is 1.

Preferably, b" and b"" or—in case n=0- a terminus of AA, preferably the N-terminus of AA, and b"" together form an amide group.

In a more preferred embodiment, the spacer $x_1$ bears the following structure:

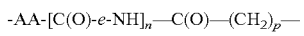

wherein e is $C_{4-8}$ alkylene, where one —$CH_2$— is replaced by triazole, in particular $C_6$ alkylene, where one —$CH_2$— is replaced by triazole;
wherein n is 0 or 1, in particular 1; and
wherein p is 1 or 2, in particular 2.

In a particularly preferred embodiment, the spacer $x_1$ bears the following structure:

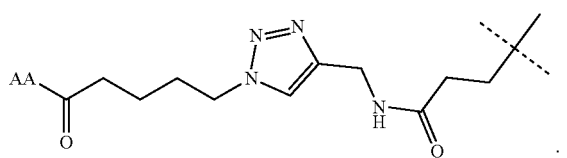

In a particular preferred embodiment (A)-$x_1$ is represented by the following structure:

In formula (I) $x_2$ is a spacer or a chemical single bond connecting (B) and (C). Preferably, $x_2$ is a spacer. The spacer $x_2$ preferably is rather hydrophilic.

In a preferred embodiment, the spacer $x_2$ bears the following structure:

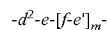

wherein $d^2$ is —[$CH_2$]$_r$—, wherein r is 1 or 2, in particular 2; and
wherein e is selected from the group consisting of —C(O)—NH—, —NH—C(O)—, —C(O)—O—, —O—C(O)—, —NH—C(O)—NH—, —NH—C(S)—NH—,

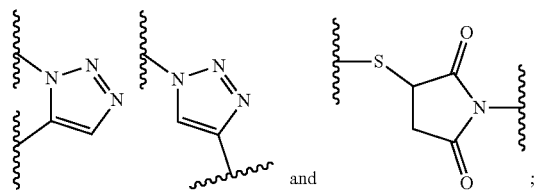

wherein one of the wavy lines indicates the conjugation site to $d^2$ and the other wavy line indicates the conjugation site to f, in particular wherein e is —C(O)—NH—;

Preferably e is —C(O)NH—.

wherein each f independently represents a residue selected from the group consisting of an $C_{1-10}$-alkylene wherein one or more —$CH_2$— moieties may optionally be replaced by —O— or —NH—, and wherein f is unsubstituted or substituted with one or more groups independently selected from the group consisting of —$NH_2$, —COOH and $R^{3a}$,

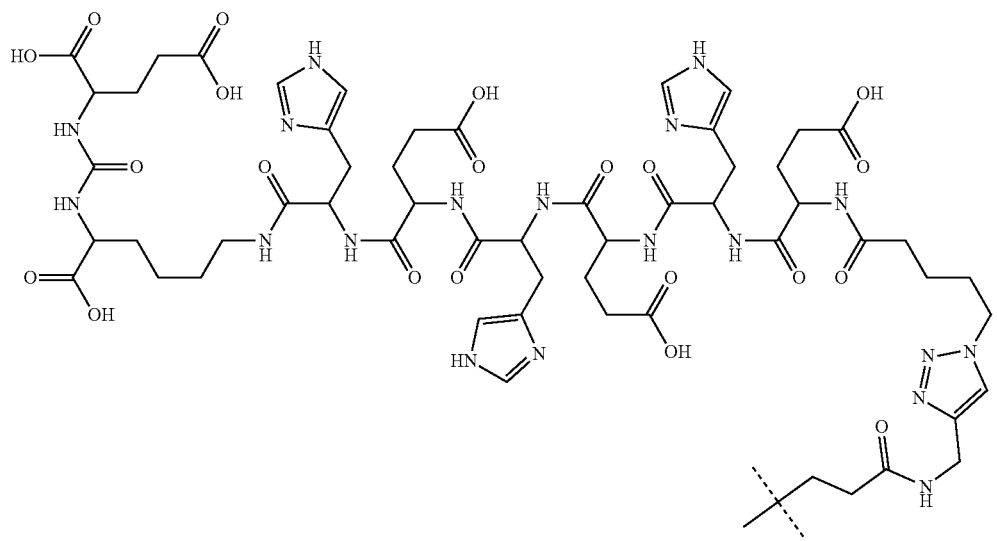

wherein $R^{3a}$ is selected from the group consisting of —(CH$_2$)$_2$—COOH, —(CH$_2$)$_4$—NH$_2$, —(CH$_2$)$_4$—N$^+$(CH$_3$)$_3$+X$^-$, —CH$_2$—COOH, —CH$_2$—SH, —CH$_2$—SO$_3$H, and

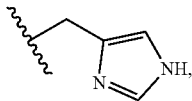

wherein X$^-$ is a pharmaceutically acceptable negatively charged counterion;
preferably wherein f is selected from the group consisting of —CH$_2$—(O—CH$_2$—CH$_2$)$_2$—CH$_2$—, —(CH$_2$)$_2$—(O—CH$_2$—CH$_2$)$_2$—, —(CH$_2$)$_2$—(CH$_2$—CH$_2$—O)$_2$—(CH$_2$)$_2$—, —(CH$_2$)$_3$—(CH$_2$—CH$_2$—O)$_2$—CH$_2$—, —(CH$_2$—CH$_2$—O)$_3$—CH$_2$—, —(CH$_2$)$_2$—(CH$_2$—CH$_2$—O)$_2$—CH$_2$—, —(CH$_2$)$_2$—(CH$_2$—CH$_2$—NH)$_2$—(CH$_2$)$_2$—, —(CH$_2$)$_3$—(CH$_2$—CH$_2$—NH)$_2$—CH$_2$—, —(CH$_2$—CH$_2$—NH)$_3$—CH$_2$—, —(CH$_2$)$_2$—(CH$_2$—CH$_2$—NH)$_2$—CH$_2$—, —(CH$_2$)$_3$—O—CH$_2$—CH$_2$—O—CH$_2$—, —CH$_2$—O—(CH$_2$)$_6$—, —(CH$_2$)$_2$—O—(CH$_2$)$_5$—, —(CH$_2$)$_3$—O—(CH$_2$)$_4$—, —(CH$_2$)$_4$—O—(CH$_2$)$_3$—, —(CH$_2$)$_5$—O—(CH$_2$)$_2$—, —(CH$_2$)$_6$—O—CH$_2$—, —CH$_2$—(O—CH$_2$—CH$_2$)$_2$—, —(CH$_2$)$_2$—O—CH$_2$—CH$_2$—O—CH$_2$—O—(CH$_2$)$_5$—, —(CH$_2$)$_2$—O—(CH$_2$)$_4$—, —(CH$_2$)$_3$—O—(CH$_2$)$_3$—, —(CH$_2$)$_4$—O—(CH$_2$)$_2$—, —(CH$_2$)$_5$—O—CH$_2$—, —CH$_2$—O—CH$_2$—CH$_2$—O—CH$_2$—, —CH$_2$—O—(CH$_2$)$_4$—, —(CH$_2$)$_2$—O—(CH$_2$)$_3$—, —(CH$_2$)$_3$—O—(CH$_2$)$_2$—, —(CH$_2$)$_4$—O—CH$_2$—, —CH$_2$—O—(CH$_2$)$_3$—, —(CH$_2$)$_2$—O—(CH$_2$)$_2$—, —(CH$_2$)$_3$—O—CH$_2$—, —CH$_2$—O(CH$_2$)$_2$—(CH$_2$)$_2$, —CH$_2$—(O—CH$_2$—, —CH$_2$—O—CH$_2$—, —(CH$_2$)$_3$—(O—CH$_2$—CH$_2$)$_2$—CH$_2$—, —(CH$_2$)$_2$—(O—CH$_2$—CH$_2$)$_2$—(CH$_2$)$_2$, —CH$_2$—(O—CH$_2$—CH$_2$)$_2$—(CH$_2$)$_3$, —CH$_2$—(O—CH$_2$—CH$_2$)$_3$—, —(CH$_2$)$_2$—(O—CH$_2$—CH$_2$)$_2$—CH$_2$—, —CH$_2$—(O—CH$_2$—CH$_2$)$_2$—(CH$_2$)$_2$—, and —(CH$_2$)$_3$—(O—CH$_2$—CH$_2$)$_2$—, CH$_2$—(NH—CH$_2$—CH$_2$)$_2$—CH$_2$—, —(CH$_2$)$_2$—(NH—CH$_2$—CH$_2$)$_2$—, —(CH$_2$)$_3$—NH—CH$_2$—CH$_2$—NH—CH$_2$—, —CH$_2$—NH—(CH$_2$)$_6$—, —(CH$_2$)$_2$—NH—(CH$_2$)$_5$—, —(CH$_2$)$_3$—NH—(CH$_2$)$_4$—, —(CH$_2$)$_4$—NH—(CH$_2$)$_3$—, —(CH$_2$)$_5$—NH—(CH$_2$)$_2$—, —(CH$_2$)$_6$—NH—CH$_2$—, —CH$_2$—(NH—CH$_2$—CH$_2$)$_2$—, —(CH$_2$)$_2$—NH—CH$_2$—CH$_2$—NH—CH$_2$—, —CH$_2$—NH—(CH$_2$)$_5$—, —(CH$_2$)$_2$—NH—(CH$_2$)$_4$—, —(CH$_2$)$_3$—NH—(CH$_2$)$_3$—, —(CH$_2$)$_4$—NH—(CH$_2$)$_2$—, —(CH$_2$)$_5$—NH—CH$_2$—, —CH$_2$—NH—CH$_2$—CH$_2$—NH—CH$_2$—, —CH$_2$—NH—(CH$_2$)$_4$—, —(CH$_2$)$_2$—NH—(CH$_2$)$_3$—, —(CH$_2$)$_3$—NH—(CH$_2$)$_2$—, —(CH$_2$)$_4$—NH—CH$_2$—, —CH$_2$—NH—(CH$_2$)$_3$—, —(CH$_2$)$_2$—NH—(CH$_2$)$_2$—, —(CH$_2$)$_3$—NH—CH$_2$—, —CH$_2$—NH—(CH$_2$)$_2$—, —(CH$_2$)$_2$—NH—CH$_2$—, —CH$_2$—NH—CH$_2$—, —(CH$_2$)$_3$—(NH—CH$_2$—CH$_2$)$_2$—CH$_2$—, —(CH$_2$)$_2$—(NH—CH$_2$—CH$_2$)$_2$—(CH$_2$)$_2$, —CH$_2$—(NH—CH$_2$—CH$_2$)$_2$—(CH$_2$)$_3$, —CH$_2$—(NH—CH$_2$—CH$_2$)$_3$—, —(CH$_2$)$_2$—(NH—CH$_2$—CH$_2$)$_2$—CH$_2$—, —CH$_2$—(NH—CH$_2$—CH$_2$)$_2$—(CH$_2$)$_2$—, —(CH$_2$)$_3$—(NH—CH$_2$—CH$_2$)$_2$—, —CH$_2$—O—(CH$_2$)$_8$—, —(CH$_2$)$_2$—O—(CH$_2$)$_7$—, —(CH$_2$)$_3$—O—(CH$_2$)$_6$—, —(CH$_2$)$_4$—O—(CH$_2$)$_5$—, —(CH$_2$)$_5$—O—(CH$_2$)$_4$—, —(CH$_2$)$_6$—O—(CH$_2$)$_3$—, —(CH$_2$)$_7$—O—(CH$_2$)$_2$—, —(CH$_2$)$_8$—O—CH$_2$—, —CH$_2$—O—(CH$_2$)$_7$—, —(CH$_2$)$_2$—O—(CH$_2$)$_6$—, —(CH$_2$)$_3$—O—(CH$_2$)$_5$—, —(CH$_2$)$_4$—O—(CH$_2$)$_4$—, —(CH$_2$)$_5$—O—(CH$_2$)$_3$—, —(CH$_2$)$_6$—O—(CH$_2$)$_2$—, —(CH$_2$)$_7$—O—CH$_2$—, —CH$_2$—NH—(CH$_2$)$_8$—, —(CH$_2$)$_2$—NH—(CH$_2$)$_7$—, —(CH$_2$)$_3$—NH—(CH$_2$)$_6$—, —(CH$_2$)$_4$—NH—(CH$_2$)$_5$—, —(CH$_2$)$_5$—NH—(CH$_2$)$_4$—, —(CH$_2$)$_6$—NH—(CH$_2$)$_3$—, —(CH$_2$)$_7$—NH—(CH$_2$)$_2$—, —(CH$_2$)$_8$—NH—CH$_2$—, —CH$_2$—NH—(CH$_2$)$_7$—, —(CH$_2$)$_2$—NH—(CH$_2$)$_6$—, —(CH$_2$)$_3$—NH—(CH$_2$)$_5$—, —(CH$_2$)$_4$—NH—(CH$_2$)$_4$—, —(CH$_2$)$_5$—NH—(CH$_2$)$_3$—, —(CH$_2$)$_6$—NH—(CH$_2$)$_2$—, —(CH$_2$)$_7$—NH—CH$_2$—, —CH(NH$_2$)—CH$_2$—, —CH$_2$—CH(NH$_2$)—, —CH(COOH)—CH$_2$—, —CH$_2$—CH(COOH)—, and —CH(R$^3$)—,
in particular f is a residue selected from the group consisting of —(CH$_2$)$_2$—(O—CH$_2$—CH$_2$)$_2$—, —CH$_2$—(O—CH$_2$—CH$_2$)$_2$—CH$_2$—, and —(CH$_2$)$_3$—O—CH$_2$—CH$_2$—O—CH$_2$—, especially —(CH$_2$)$_2$—(O—CH$_2$—CH$_2$)$_2$—;
wherein each e″ is independently selected from the group consisting of a chemical bond, —NH—C(O)—, —C(O)—NH—, —C(O)—O— and —O—C(O)—, —NH—C(O)—NH—, —NH—C(S)—NH—, —C(O)—N(CH$_3$)—, —N(CH$_3$)—C(O)—, —NH—C(S)—, —C(S)—NH—,

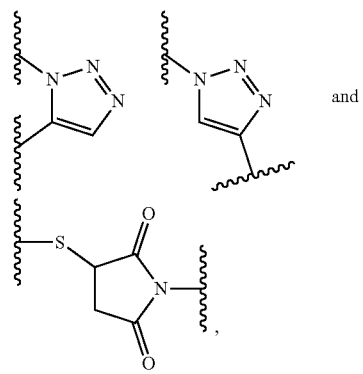

and wherein one of the wavy lines indicates the conjugation site to f and the other wavy line indicates the conjugation site to the at least one dye moiety (C), in particular wherein e″ is —NH—C(O)—; and
wherein m indicates an integer from 0 to 8, preferably 0 to 4, even more preferably 0 to 2, even more preferably 0 or 1 and in particular 1.
In a more preferred embodiment, the spacer $x_2$ bears one of the following structures:
—(CH$_2$)$_t$—C(O)—NH—(CH$_2$)$_u$—(O—CH$_2$—CH$_2$)$_v$—(CH$_2$)$_w$-e″-, or
—(CH$_2$)$_t$—C(O)—NH—(CH$_2$—CH$_2$—O)$_v$—CH$_2$-e″-
wherein t is 1 or 2, in particular 2;
wherein u is an integer from 1 to 10, preferably from 1 to 3, in particular 2;
wherein v is an integer from 0 to 3, in particular 2;
wherein w is an integer from 0 to 2, in particular 0;
In an even more preferred embodiment, the spacer y bears one of the following structures:
—(CH$_2$)$_2$—C(O)—NH—(CH$_2$)$_2$—(O—CH$_2$—CH$_2$)$_2$-e″-
—(CH$_2$)$_2$—C(O)—NH—(CH$_2$)$_2$—(O—CH$_2$—CH$_2$)$_2$—NH—C(O)—CH$_2$—(O—CH$_2$—CH$_2$)$_{n'}$—O—CH$_2$-e″-,
—(CH$_2$)$_2$—C(O)—NH—(CH$_2$)$_2$—(O—CH$_2$—CH$_2$)$_2$—NH—[C(O)—CH((CH$_2$)$_2$COOH)—NH]$_{n''}$—C(O)—CH((CH$_2$)$_2$COOH)-e″-,
—(CH$_2$)$_2$—C(O)—NH—(CH$_2$)$_2$—(O—CH$_2$—CH$_2$)$_2$—NH—[C(O)—CH((CH$_2$)$_4$NH$_2$)—NH]$_{n''}$—C(O)—CH((CH$_2$)$_4$NH$_2$)-e″-, or —(CH$_2$)$_2$—C(O)—NH—(CH$_2$)$_2$—(O—CH$_2$—CH$_2$)$_2$—NH—[C(O)—CH((CH$_2$)$_4$N$^+$(CH$_3$)$_3$)—NH]$_{n''}$—C(O)—CH((CH$_2$)$_4$N$^+$(CH$_3$)$_3$)-e''-+X$^-$, wherein n' is an integer from 1 to 3;

wherein n'' is an integer from 0 to 2;

wherein X$^-$ is a pharmaceutically acceptable negatively charged counterion; and wherein each e'' is independently selected from the group consisting of a chemical bond, —NH—C(O)—, —C(O)—NH—, —C(O)—O— and —O—C(O)—, —NH—C(O)—NH—, —NH—C(S)—NH—, —C(O)—N(CH$_3$)—, —N(CH$_3$)—C(O)—, —NH—C(S)—, —C(S)—NH—,

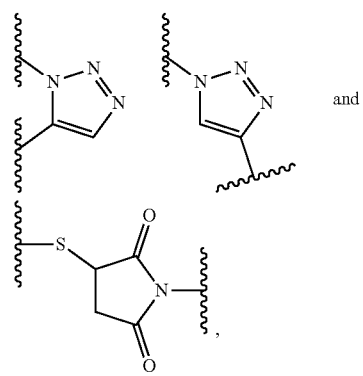
and wherein one of the wavy lines indicates the conjugation site to f and the other wavy line indicates the conjugation site to the at least one dye moiety (C), in particular wherein e'' is —NH—C(O)—.

In particular x$_2$ is represented by formula —(CH$_2$)$_2$—C(O)—NH—(CH$_2$)$_2$—(O—CH$_2$—CH$_2$)$_2$-e''-.

The compound according to the present invention or a pharmaceutically acceptable salt thereof may preferably complex one or more radiometal(s) and may thereby form a compound-radiometal complex or, alternatively, may be non-complexed. Evidently, for detecting a radioactivity signal, said compound or salt thereof is preferably complexed with at least one radiometal, whereas, for detecting a fluorescence signal, it is optional whether said compound or salt thereof complexes a radiometal or not. Accordingly, in the context of detecting a radioactivity signal the term "compound" may be understood in a way that the compound preferably complexes at least one radiometal. However the molecular weight of the compound or salt indicated herein is based on the structure without radiometal.

As mentioned above, the chelator moiety or radiometals (B) is preferably a chelator suitable to complex $^{68}$Ga, $^{99m}$Tc or $^{8a}$Rb, in particular suitable to complex $^{68}$Ga in aqueous environment.

Gallium-68 ($^{68}$Ga) has a half-life of approximately 68 minutes and is thus rather inconvenient for longer transports. Therefore, it may typically be generated nearby the site where it is complexed with the compound of the present invention or a pharmaceutically acceptable salt thereof and administered to a patient in vivo and/or a sample in vitro.

Therefore, in a preferred embodiment, the chelator moiety of radiometals (B) is a $^{68}$Ga-chelator moiety, preferably a $^{68}$Ga-chelator moiety.

The chelator moiety of radiometals (B) is preferably:

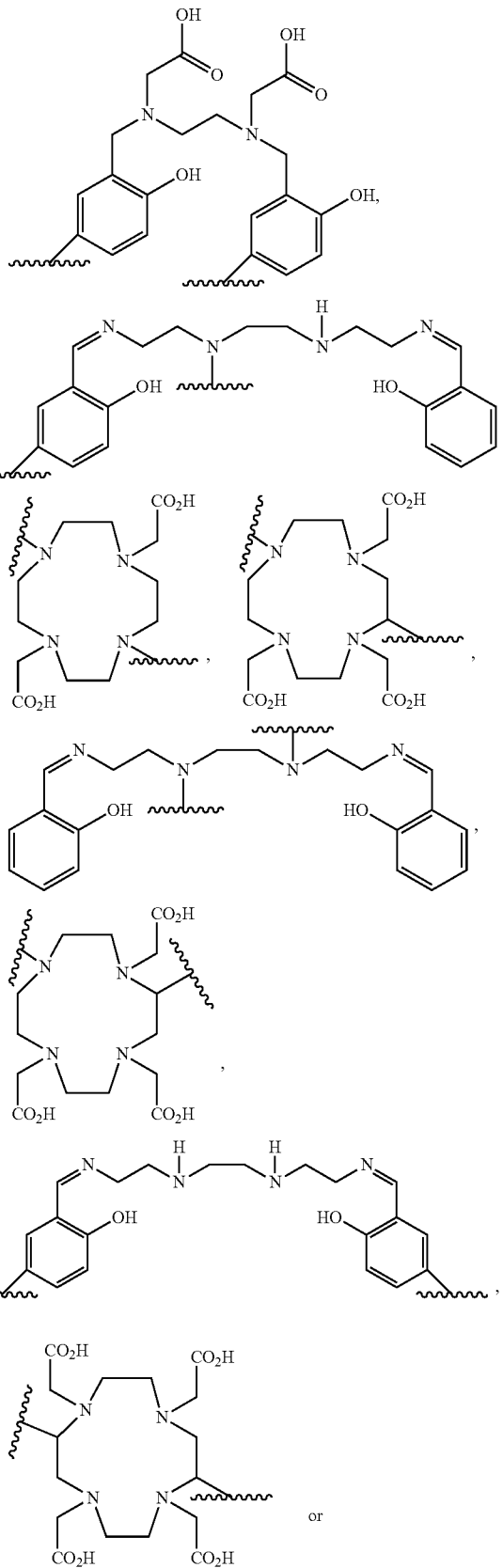

or

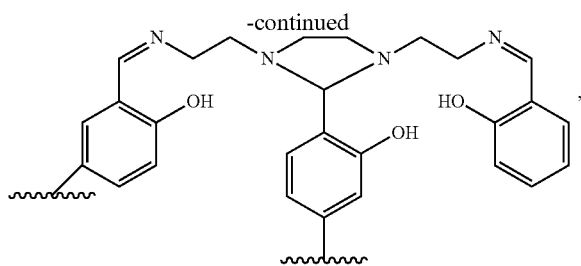

wherein in each of the structures one of the wavy lines indicates the conjugation site to the at least one motif specifically binding to cell membranes of neoplastic cells (A) via spacer $x_1$ as defined herein, and the other wavy line indicates the conjugation site to the dye moiety (C), preferably via the spacer $x_2$ as defined herein.

In particular, the chelator moiety is

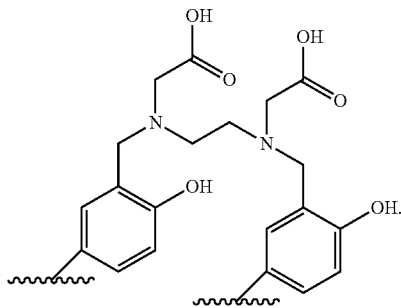 [SMILES: *c1ccc(O)c(CN(CCN(CC(=O)O)Cc2cc(*)ccc2O)CC(=O)O)c1]

When this chelator is used, b'''' preferably is —C(O)—, $d^1$ and $d^2$ preferably are each —(CH$_2$)$_2$—, and e' preferably is —C(O)—NH or —C(O)—O—, especially —C(O)NH—. Therefore, the chelator moiety is conjugated with two —C(O)—(CH$_2$)$_2$—# moieties, wherein these are conjugated at the position indicated by "#" with the binding sites of the aforementioned chelator moiety indicated by the wavy lines. Then, this residue is also designated as "HBED-CC".

Preferably, (A)-$x_1$-(B)-$x_2$- is represented by the following formula:

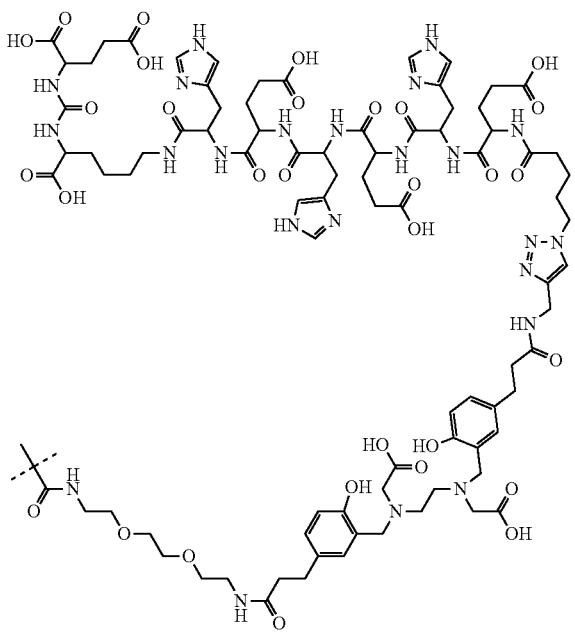

It will be noted that several of these "$^{68}$Ga-chelator moieties" exemplarily listed above, may also serve as structures complexing one or more other radiometal(s) such as, e.g., $^{64}$Cu, in particular in aqueous environment of approximate neutral pH.

Preferably, neither the motif specifically binding to cell membranes of neoplastic cells (A) nor the complexed radiometal nor the chelator moiety of radiometals (B) quench the intensity of the fluorescence signal obtainable from the dye moiety (C) at its emission maximum in an aqueous environment of approximately neutral pH (i.e., pH 6-8, in particular 6.5-7.5) by more than 50%.

Preferably, the dye moiety (C) is suitable for emit light in an aqueous environment of approximately neutral pH, i.e., pH 6-8, in particular 6.5-7.5, in particular pH 7.0-7.5.

In a preferred embodiment, the dye moiety (C) is a fluorescent dye moiety having an emission maximum in the range from 400 nm to 1000 nm.

The dye moiety (C) has the formula

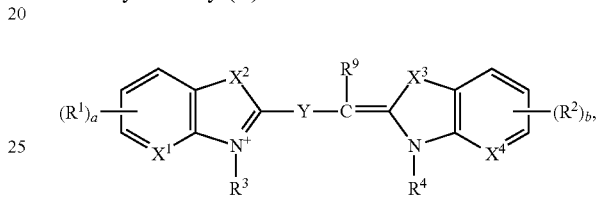

wherein
$X^1$ and $X^4$ are independently selected from the group consisting of —N=, —N(R$^5$)=, and —C(R$^6$)=;
$X^2$ and $X^3$ are independently selected from the group consisting of O, S, Se, N(R$^5$), and C(R$^6$R$^7$);
Y is a linker connecting the two moieties of (C) and permitting electron delocalization between said moieties, wherein Y optionally comprises a group (L-)$_c$Z$^0$;
a and b are independently selected from the group consisting of 1, 2, and 3;
each $R^1$ and each $R^2$ is independently (L-)$_c$Z, (L-)$_c$Z$^0$ or H; and two adjacent $R^1$ and/or two adjacent $R^2$ can also form an aromatic ring, which is optionally substituted with one or more (L)$_c$Z or (L-)$_c$Z$^0$;
$R^3$, $R^4$, $R^5$, $R^6$, $R^7$, $R^9$ are independently selected from the group consisting of (L-)$_c$Z, (L-)$_c$Z$^0$, and H;
each c is independently 0, or 1;
each L is independently $T^1$, —OT$^1$-, —ST$^1$-, —C(O)T$^1$-, —C(O)OT$^1$-, —OC(O)T$^1$-, —C(O)NHT$^1$-, —NHC(O)T$^1$, or a C$_{1-10}$ alkylene group, which is optionally interrupted and/or terminated by one or more of —O—, —S—, —C(O)—, —C(O)O—, —OC(O)—, —C(O)NH—, —NHC(O)O—, and $T^1$;
$T^1$ is phenyl, naphthyl, indenyl, indanyl, tetralinyl, decalinyl, adamantyl, C$_{3-7}$ cycloalkyl, 3 to 7 membered heterocyclyl, or 7 to 11 membered heterobicyclyl, wherein $T^1$ is optionally substituted with one or more substituents selected from the group consisting of halogen, CN, C(O)R$^8$, COOR$^8$, OR$^8$, C(O)N(R$^8$R$^{8a}$), S(O)$_2$N(R$^8$R$^{8a}$), S(O)N(R$^8$R$^{8a}$), S(O)$_2$R$^8$, N(R$^8$)S(O)$_2$N(R$^{8a}$R$^{8b}$), SR$^8$, N(R$^8$R$^{8a}$), NO$_2$; OC(O)R$^8$, N(R$^8$)C(O)R$^{8a}$, N(R$^8$)S(O)$_2$R$^{8a}$, N(R$^8$)S(O)R$^{8a}$, N(R$^8$)C(O) N(R$^{8a}$R$^{8b}$), N(R$^8$)C(O)OR$^{8a}$, OC(O)N(R$^8$R$^{8a}$), oxo (=O), where the ring is at least partially saturated, or C$_{1-6}$ alkyl, wherein C$_{1-8}$ alkyl is optionally substituted with one or more halogen, which are the same or different;
each Z is independently H, halogen, CN, C(O)R$^8$, C(O)OR$^8$, C(O)O—OR$^8$, C(O)O$^-$ OR$^8$, C(O)N(R$^8$R$^{8a}$), S(O)$_2$OR$_8$, S(O)$_2$O$^-$, S(O)$_2$N(R$^8$R$^{8a}$), S(O)N(R$^8$R$^{8a}$), S(O)$_2$R$^8$, S(O)R$^8$, N(R$^8$)S(O)$_2$N(R$^{8a}$R$^{8b}$), SR$^8$, N(R$^8$R$^{8a}$), NO$_2$; P(O)(OR$^8$)$_2$, P(O)(OR$^8$)O$^-$, OC(O)R$^8$, N(R$^8$)C(O)R$^{8a}$, N(R$^8$)S(O)$_2$R$^{8a}$, N(R$^8$)S(O)R$^{8a}$, N(R$^8$)C(O)N(R$^{8a}$R$^{8b}$), N(R$^8$)C(O)OR$^{8a}$, or OC(O)N(R$^8$R$^{8a}$);

R$^{8a}$, R$^{8a}$, R$^{8b}$ are independently selected from the group consisting of H, or C$_{1-6}$ alkyl, wherein C$_{1-8}$ alkyl is optionally substituted with one or more halogen, which are the same or different;

Z$^0$ is a chemical bond connecting (C) to x$_2$ or to (B) in case x$_2$ is a chemical single bond;

provided that one of R$^1$, R$^2$, R$^3$, R$^4$, R$^5$, R$^6$, R$^7$, R$^9$ is (L-)$_c$Z$^0$ or that Y comprises (L-)$_c$Z$^0$.

Accordingly, one of the residues R$^1$, R$^2$, R$^3$, R$^4$, R$^5$, R$^6$, R$^7$ serve as connecting group, atom or bond (L-)$_c$Z$^0$ of dye moiety (C) to x$_2$ or (B). Preferably R$^3$ or R$^4$ represent (L-)$_c$Z$^0$. More preferably, R$^3$ is (L-)$_c$Z$^0$.

Preferably, in formula (C) X$^1$ and X$^4$ are the same and preferably C(R$^6$), more preferably CH.

Preferably, in formula (C) X$^2$ and X$^3$ are the same and preferably C(R$^6$R$^7$), more preferably R$^6$ and R$^7$ are the same and even more preferably L-Z with L=C$_{1-10}$ alkylene, and even more preferably L=CH$_2$, and Z=H.

Preferably, R$^9$ is H.

Preferably, in formula (C) Y does not comprise (L-)$_c$Z$^0$ and preferably Y is

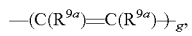

wherein g is 1, 2, 3, or 4 (preferably 2 or 3, more preferably 3) and each R$^{9a}$ is (L-)$_c$Z, or H; and two R$^{9a}$ can also form a carbocyclic ring having 5, 6, or 7 carbon atoms or a 4 to 7 membered heterocylic ring;

each c is independently 0, or 1;

each L is independently T$^1$, —OT$^1$-, —ST$^1$-, —C(O)T$^1$-, —C(O)OT$^1$-, —OC(O)T$^1$-, —C(O)NHT$^1$-, —NHC(O)T$^1$-, or a C$_{1-10}$ alkylene group, which is optionally interrupted and/or terminated by one or more of —O—, —S—, —C(O)—, —C(O)O—, —OC(O)—, —C(O)NH—, —NHC(O)O—, and T$^1$;

T$^1$ is phenyl, naphthyl, indenyl, indanyl, tetralinyl, decalinyl, adamantyl, C$_{3-7}$ cycloalkyl, 4 to 7 membered heterocyclyl, or 7 to 11 membered heterobicyclyl, wherein T$^1$ is optionally substituted with one or more substituents selected from the group consisting of halogen, CN, C(O)R$^8$, COOR$^8$, OR$^8$, C(O)N(R$^8$R$^{8a}$), S(O)$_2$N(R$^8$R$^{8a}$), S(O)N(R$^8$R$^{8a}$), S(O)$_2$R$^8$, N(R$^8$)S(O)$_2$N(R$^{8a}$R$^{8b}$), SR$^8$, N(R$^8$R$^{8a}$), NO$_2$; OC(O)R$^8$, N(R$^8$)C(O)R$^{8a}$, N(R$^8$)S(O)$_2$R$^{8a}$, N(R$^8$)S(O)R$^{8a}$, N(R$^8$)C(O)N(R$^{8a}$R$^{8b}$), N(R$^8$)C(O)OR$^{8a}$, OC(O)N(R$^8$R$^{8a}$), oxo (=O), where the ring is at least partially saturated, or C$_{1-6}$ alkyl, wherein C$_{1-6}$ alkyl is optionally substituted with one or more halogen, which are the same or different;

R$^8$, R$^{8a}$, R$^{8b}$ are independently selected from the group consisting of H, or C$_{1-6}$ alkyl, wherein C$_{1-6}$ alkyl is optionally substituted with one or more halogen, which are the same or different;

each Z is independently H, halogen, CN, C(O)R$^8$, C(O)OR$^8$, C(O)O$^-$ OR$^8$, C(O)N(R$^8$R$^{8a}$), S(O)$_2$OR$_8$, S(O)$_2$O$^-$, S(O)$_2$N(R$^8$R$^{8a}$), S(O)N(R$^8$R$^{8a}$), S(O)$_2$R$^8$, S(O)R$^8$, N(R$^8$)S(O)$_2$N(R$^{8a}$R$^{8b}$), SR$^8$, N(R$^8$R$^{8a}$), NO$_2$; P(O)(OR$^8$)$_2$, P(O)(OR$^8$)O$^-$, OC(O)R$^8$, N(R$^8$)C(O)R$^{8a}$, N(R$^8$)S(O)$_2$R$^{8a}$, N(R$^8$)S(O)R$^{8a}$, N(R$^8$)C(O)N(R$^{8a}$R$^{8b}$), N(R$^8$)C(O)OR$^{8a}$, or OC(O)N(R$^8$R$^{8a}$).

Preferably, Y is

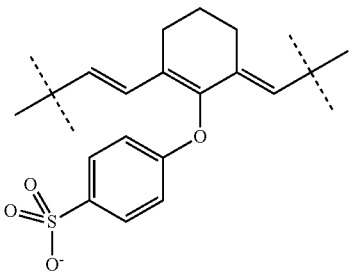

or —(C(R$^{9a}$)=C(R$^{9a}$)—)$_g$ with g=2 and each R$^{9a}$=H.

Preferably, in formula (C) a and b are the same and preferably 1, more preferably with R$^1$ and R$^2$=SO$_3^-$.

Preferably, in formula (C) a and b are the same and 2, preferably wherein two adjacent R$^1$ and two adjacent R$^2$ form a phenyl ring.

Preferably, in formula (C) one of R$^3$ and R$^4$ is (L-)$_c$Z$^{Z0}$ and the other is (L)$_c$Z with L-=C$_{1-10}$ alkylene and Z=H or SO$_3^-$ and c preferably =1.

Preferably, (L-)$_c$Z$^0$ is C$_{1-10}$ alkylene (c=1, Z$^0$ a chemical bond), preferably C$_{3-7}$ alkylene, more preferably C$_5$ alkylene, connecting (C) to x$_2$ or to (B) in case x$_2$ is a chemical single bond.

Preferably, (L)$_c$Z is C$_{1-10}$ alkylene, preferably C$_{3-7}$ alkylene, more preferably C$_4$ alkylene, c is 1 and Z is SO$_3^-$.

In a highly preferred embodiment, the dye moiety (C) is a fluorescent dye moiety selected from the group consisting of the following structures:

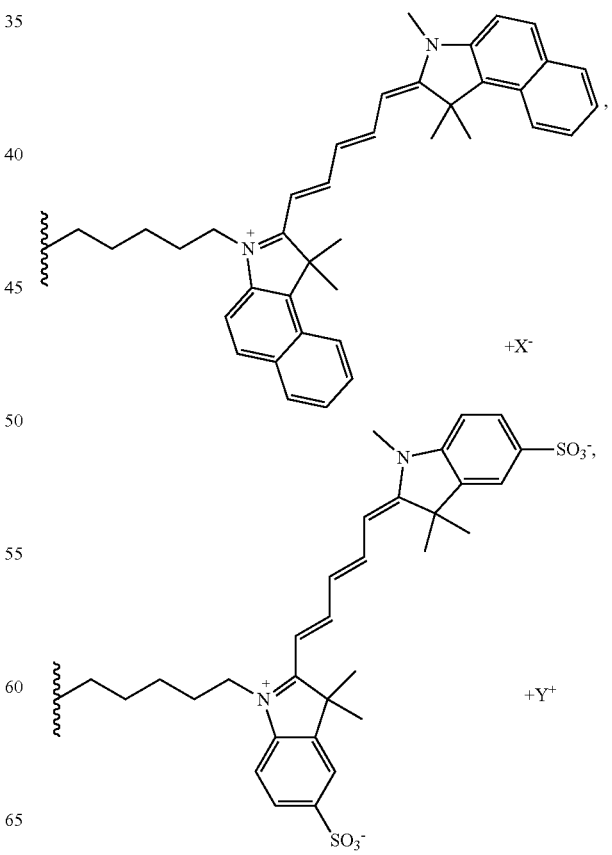

27

-continued

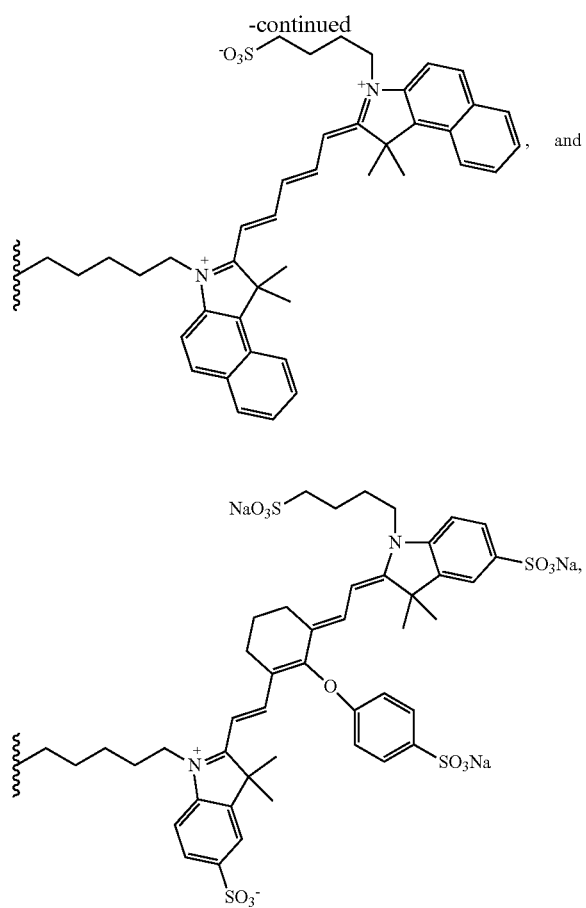

, and wherein X⁻ is a pharmaceutically acceptable negatively charged counterion;
wherein Y⁺ is a pharmaceutically acceptable positively charged counterion; and
wherein the wavy line indicates the conjugation site to the rest of the compound of the present invention.

28

Most preferred is

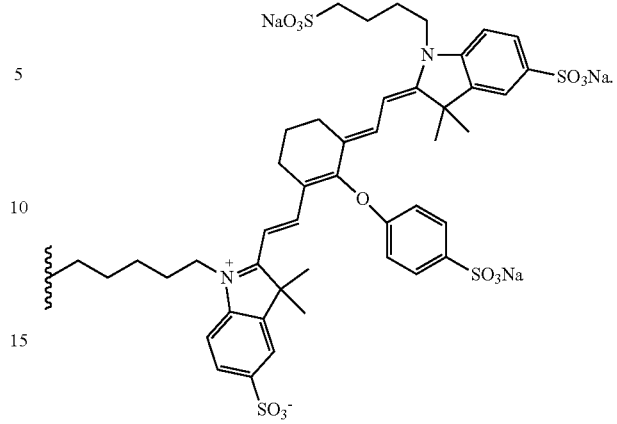

A pharmaceutically acceptable negatively charged counterion X⁻ may be understood in the broadest sense as laid out above.

Likewise, also a pharmaceutically acceptable positively charged counterion Y⁺ may have any valency. Therefore, Y⁺ may exemplarily have a charge of +1, +2, +3 or +4, preferably of +1 or +2. Y⁺ may be any pharmaceutically acceptable positively charged ion. Preferably, the ion is such well-soluble in aqueous liquids. Exemplarily, Y⁺ may be selected from the group consisting of a cation of an alkali metal (e.g., Na⁺, K⁺, Li⁺), a cation of an alkaline earth metal (e.g., $Mg^{2+}$, $Ca^{2+}$), $Al^{3+}$, $NH_4^+$, H⁺ and a cation of an organically bound amine. Further, it will be understood that the counterion typically depends on the surrounding liquids such as those comprised in the buffer the compound is dissolved in and the body fluids after injection in vivo. In vivo, extracellularly, one of the main, but not sole positively charged counterions is Na⁺.

Preferably, the wavy line indicates the conjugation site to the spacer $x_2$. More preferably, the wavy line indicates the conjugation site to e".

Accordingly, in a highly preferred embodiment, the compound of the present invention has the following chemical structure:

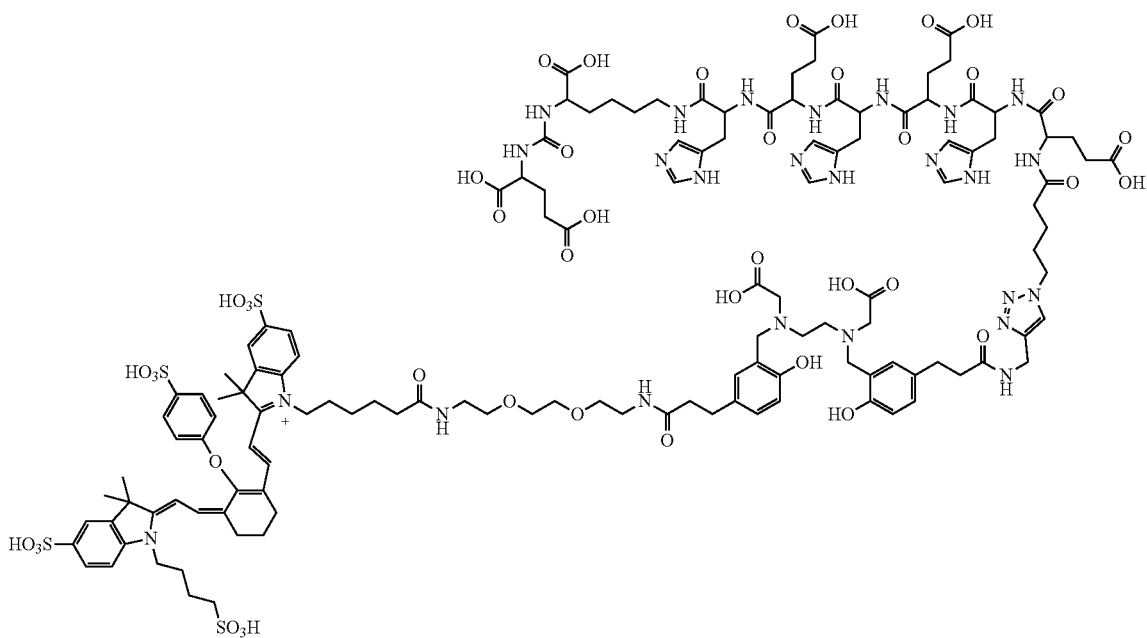

The compound according to the present invention may be obtained from rational chemical synthesis. Exemplary routes for the preparation of compounds or pharmaceutically acceptable salts thereof of the present invention are described in US 2015/0110715 A1.

The compound according to the present invention may be essentially pure or may form part of a composition further comprising a radiometal and one or more pharmaceutically acceptable carriers.

The present invention further relates to a composition comprising:
(a) the compound according to the present invention or a pharmaceutically acceptable salt thereof as defined above;
(b) a radiometal, preferably selected from the group consisting of $^{89}$Zr, $^{44}$Sc, $^{111}$In, $^{90}$Y, $^{67}$Ga, $^{68}$Ga, $^{177}$Lu, $^{99m}$TC, $^{82}$Rb, $^{64}$Cu, $^{67}$Cu, $^{153}$Gd, $^{155}$Gd, $^{157}$Gd, $^{213}$Bi, $^{225}$Ac and $^{59}$Fe, in particular $^{68}$Ga; and optionally
(c) one or more pharmaceutically acceptable carriers.

A pharmaceutically acceptable carrier may be any agent that is pharmaceutically acceptable and addable to the compound complexed with the radiometal (compound-radiometal complex).

Exemplarily, a pharmaceutically acceptable carrier may comprise a solvent with no or low toxicity such as, e.g., water, an aqueous buffer (e.g., a Hepes, Tris, or phosphate buffer, a phosphate buffer), a pharmaceutically acceptable organic solvent (e.g., dimethyl sulfoxide (DMSO), ethanol, vegetable oil, paraffin oil) or a combination of two or more thereof.

Furthermore, the pharmaceutically acceptable carrier may contain one or more detergents, one or more foaming agents (e.g., sodium lauryl sulfate (SLS)/sodium doceyl sulfate (SDS)), one or more coloring agents (e.g., $TiO_2$, food coloring), one or more vitamins, one or more salts (e.g., sodium, potassium, calcium, zinc salts), one or more humectants (e.g., sorbitol, glycerol, mannitol, propylenglycol, polydextrose), one or more enzymes, one or more preserving agents (e.g., benzoic acid, methylparabene), one or more texturing agents (e.g., carboxymethyl cellulose (CMC), polyethylene glycol (PEG), sorbitol), one or more emulsifiers, one or more bulking agents, one or more glacing agents, one or more separating agents, one or more antioxidants, one or more herbal and plant extracts, one or more stabilizing agents, one or more polymers (e.g., hydroxypropyl methacrylamide (HPMA), polyethylene imine (PEI), carboxymethyl cellulose (CMC), polyethylene glycol (PEG)), one or more uptake mediators (e.g., polyethylene imine (PEI), dimethyl sulfoxide (DMSO), a cell-penetrating peptide (CPP), a protein transduction domain (PTD), an antimicrobial peptide, etc.) one or more antibodies, one or more sweeteners (e.g., acesulfame, an acesulfame salt (e.g., acesulfame potassium (acesulfame K), aspartame, cyclamate, saccharin, a saccharin salt (e.g., saccharin sodium (saccharin Na)), alitame, neotame, sucralose, dulcin, salt of aspartame-acesulfame, sorbitol, stevia, glycerol, inulin, mannitol, isomalt, maltitol, malto-oligosaccharide, lactitol, xylitol, glucin, neohesperidin dihydrochalcone, P-4000, brazzein, curculin, erythritol, glycyrrhizin, hydrogenated starch hydrolysates, luo han guo, mabinlin, miraculin, monatin, monellin, osladin, pentadin, tagatose, thaumatin), one or more counterstain dyes (e.g., fluorescein, fluorescein derivatives, Cy dyes, an Alexa Fluor dyes, rhodamine, quantum dots, etc.), one or more homeopathic ingredients one or more gustatory substances and/or one or more fragrances. The diagnostic composition will typically be formed by contacting the aforementioned component with another by any way known in the art. Preferably, the diagnostic composition is formed, thus, the above-referenced components are contacted with another prior to being administered to a patient.

The radiometal may be obtained commercially of, may be obtained from nature or may be obtained from a cyclotron. Preferably, the radiometal is obtained from a gallium-68 generator or a cyclotron, in particular from a gallium-68 generator or a cyclotron that is localized near the site where the composition according to the present invention is mixed and where optionally also the diagnosis in vivo and/or in vitro is performed. Particularly preferably, the radiometal $^{68}$Ga is obtained from a gallium-68 generator, thus, a device used to extract the positron-emitting isotope $^{68}$Ga of gallium from a source of decaying germanium-68. The parent isotope $^{68}$Ge is known to have a half-life of 271 days and may thus be shipped to the site where the gallium-68 generator is located.

Such composition may be used for diagnosing a patient for neoplasia, in particular cancerous tissue or tissue of risk of becoming cancerous, in a patient in vivo as well as in tissue culture in vitro.

Accordingly, a further aspect of the present invention relates to a method for diagnosing a neoplasm in a patient suffering therefrom or being at risk thereof, comprising administering sufficient amounts of the composition according to the present invention to said patient.

Preferably, the composition of the present invention is used as diagnostic agent.

In the context of the diagnostic method, the definitions of the terms as specified in the context of the compound, the compound-radiometal complex or a pharmaceutically acceptable salt thereof above also apply.

As used in the context of the present invention, the term "patient" may be understood in the broadest sense as a subject or individual the compound or compound-radiometal complex of the present invention or pharmaceutically acceptable salt thereof is administered to, irrespective, whether it is a human or an animal and whether clinical symptoms occur or do not occur. Preferably, the patient is a mammalian including human, more preferably a human, a dog, a horse, a bovine, a pig, a mule, a donkey, a sheep, a goat, or a camel. Particularly preferably, the patient is a human patient.

A patient suffering from neoplasia may be understood in the broadest sense as any patient having a neoplasm. Herein, the patient suffering from neoplasia does not necessarily bear any clinical symptoms. The patient may be aware of a neoplasm or may not be aware of having a neoplasm. Likewise, the physician of the patient may be aware of the presence of a neoplasm or may not be aware thereof. The patient may optionally also suffer from pain, a feeling of pressure and/or gastrointestinal and/or urinal dysfunction.

The term "patient at risk thereof" may be understood in the broadest sense as any patient who could potentially develop a neoplasm. In particular, the patient may be at an age, may live at conditions, be exposed to a medicinal treatment influencing gene expression and/or may have a genetic heredity associated with an increased risk of developing a neoplasm. Exemplarily, the patient at risk may be older than 40 years, preferably older than 45 years, more preferably older than 50 years, even more preferably older than 60 years, even more preferably older than 70 years, in particular older than 80 years. Alternatively or additionally, the patient may be overweight. Alternatively or additionally, the patient may bear a family history, wherein cancer is comparably common, in particular wherein first-degree family members suffer from cancer.

The compound, compound-radiometal complex or a pharmaceutically acceptable salt thereof may be administered to the patient by any means. Preferably, it is injected into the tissue of interest (i.e., the neoplastic tissue or tissue being of risk of being neoplastic) or into a blood vessel via a syringe or a drip. Alternatively it may also be injected intraperitoneally or may be administered orally, nasally, respiratorically, topically or subcutaneously.

Exemplarily, the compound, compound-radiometal complex or pharmaceutically acceptable salt thereof may be injected intravenously (i.v.), intraperitoneally (i.p.), intraarterially (i.a.), intramusculary (i.m.) and/or subcutaneously (s.c.). Alternatively, the compound, compound-radiometal complex or pharmaceutically acceptable salt thereof may be taken up orally, e.g., as a powder, a tablet, a pill, a capsule, a chewable capsule, syrup, juice, gel, liquid or paste. Alternatively, the compound, compound-radiometal complex or pharmaceutically acceptable salt thereof may be taken up nasally (intra nasal) (e.g., as spray or aerosol), percutaneously (e.g., as cream, spray or ointment and/or via a coated plaster) and/or respiratorically (e.g., by inhalation of an aerosol or of a spray). It will be understood that the compound, compound-radiometal complex or pharmaceutically acceptable salt thereof may be administered locally or systemically.

Sufficient amounts of the compound, compound-radiometal complex or pharmaceutically acceptable salt thereof suitable for the treatment may depend on the physicochemical and pharmacological properties of said compound pharmaceutically acceptable salt thereof (e.g., the bioavailability, charge, lipophilicity, molecular weight etc.), the route of administration (e.g., including or excluding a first pass effect), the body mass of the patient, the metabolism of the patient (e.g., the rate of metabolism and excretion of the compound, compound-radiometal complex or pharmaceutically salt thereof) and the accuracy of the employed analytical apparatuses (i.e., analytical apparatuses of higher sensitivity may typically require lower amounts of compound, compound-radiometal complex or pharmaceutically salt thereof).

Neoplasia detectable by the composition of the present invention may be any neoplasia known in the art.

In a preferred embodiment, the neoplasia is cancer, in particular prostate cancer.

Prostate cancer as used herein may be understood in the broadest sense as any form of cancer that develops in the prostate, i.e., a gland in the male reproductive system. Preferably, prostate cancer is prostate carcinoma.

A patient of risk of developing prostate cancer may optionally have one or more risk factors selected from the group consisting of:
a conspicuous family history (e.g., having a first-degree relative (father or brother) suffers from prostate cancer);
a genetic background of risk (e.g., one or more mutations in BRCA1 and/or BRCA2 genes, one or more mutations in the hereditary Prostate cancer gene 1 (HPC1), one or more mutations in the androgen receptor, one or more mutations in the vitamin D receptor, a TMPRSS2-ETS gene family fusion (in particular TMPRSS2-ERG or TMPRSS2-ETV1/49), a loss of one or more cancer suppressor gene(s) (e.g., in the p53 gene, the PTEN (gene), KAI1, E-cadherin and/or CD44);
lower blood levels of vitamin D;
elevated blood levels of testosterone; and/or
occurrence of an infection or inflammation of the prostate (prostatitis) (e.g., infections with chlamydia, gonorrhea, Xenotropic MuLV-related virus (XMRV) HPV-16, HPV-18, HSV-2 and/or syphilis)

As already mentioned above, the diagnosis of the patient may include readout of the radioactive signal occurring from the complexed radiometal and/or the fluorescence signal occurring from the fluorescent dye. Both signals may enable the detection of the localizations and/or size of a neoplasm.

In a preferred embodiment, the method comprises at least the following steps:
(i) administering said composition to a patient;
(ii) detecting the radioactive signal of the radiometal,
preferably wherein step (ii) is conducted by three-dimensional imaging, in particular comprising positron emission tomography (PET).

As used throughout the context of the present invention, the term "three-dimensional imaging" may be understood in the broadest sense as any method enabling to determine the localization of the complex of the compound-radiometal complex in a three-dimensional object. Such method may exemplarily be positron emission tomography (PET), magnetic resonance imaging (MRI), radiography (in particular computer tomography), single photon emission computed tomography (SPECT) or a combination of two or more thereof.

Highly preferably, the method includes positron emission tomography (PET). PET may be understood in the broadest sense as a method based on the detection of pairs of gamma rays/photons emitted in opposite directions wherein the emission of said gamma rays/photons is caused by the nihilation event provoked by the liaison of an electron present in the patient's body or sample with a proton emitted upon disintegration of the radiometal. Three-dimensional images of tracer concentration within the body or sample may then be constructed by computer analysis. PET represents a nuclear medical imaging method that enables production of a three-dimensional image reconstruction and thus visualization of the shape, size and localization of neoplasia.

The person skilled in the art will know how to conduct such measurements and that PET may very well be combined with other imaging methods such as, e.g., three-dimensional fluorescent detection (e.g. via fluorescence molecular tomography (FMT)), CT and/or MRI. Such combinational detection may be performed concomitantly or subsequently and may be conducted by the same apparatus or different apparatuses.

A combination of two or more imaging methods may enable an overlay of the data obtained from such methods and, thereby, enables combining a high-resolution image (e.g., from MRI and/or CT) with a method enabling to depict aggregation of the compound-radiometal complex of the present invention in a certain area. Such results may enable a particularly precise determination of neoplastic tissue in a patient.

Before being administered to the patient, the composition of the present invention may typically be generated by admixing the compound-radiometal complex pharmaceutically acceptable salt thereof with the radiometal (forming a complex) and optionally a pharmaceutically acceptable carrier. Therefore, the method may optionally further include the preceding step of admixing the composition according to the present invention.

As mentioned above, a benefit of the compound, compound-radiometal complex or pharmaceutically salt thereof of the present invention is the ability to diagnose neoplasia in vivo and in vitro by means of detecting two different signals, i.e., (i) radioactive radiation resulting from the radiometal and (ii) fluorescence resulting from the dye moiety.

This enables, in one step, to determine the precise localization of a neoplasm in the whole patient's body or at least in a larger part thereof by means of detecting the radioactive signal, in particular be means of PET imaging. In a further step, the fluorescence may be detected. This may likewise be performed in the whole patient's body or at least in a larger part thereof, but may also be performed when the patient's body is opened, i.e., when the tissue of interest is laid open during a surgery.

Accordingly, in a further preferred embodiment, the method further comprises: (iii) detecting the dye moiety (C), preferably comprising molecular imaging.

It will, however, be noted that alternatively optionally also either the one or the other detection method may be used, i.e., only the radioactivity signal from the radiometal or only the fluorescence signal from the dye moiety may be detected. Detecting the fluorescence signal only may allow the omittance of the radiometal what may make handling easier and decrease costs, but may, typically, reduce detection flexibility and data accuracy.

Throughout the present invention, the term "molecular imaging" in the context of detecting the dye moiety be understood in the broadest sense as any method enabling the localization of the dye moiety and, thus, the compound (or its radiometal complex) according to the present invention in an object of interest. Molecular imaging in this context may also be designated as "Fluorescence Molecular Imaging", abbreviated "FMI". As used in the in the context of detecting the dye moiety, detecting may be performed visually or in an apparatus-assisted manner.

Preferably, molecular imaging refers to detecting fluorescence in a patient's body or in a cell culture in a resolution (i.e., the nearest proximity of objects still distinguishable from another) enabling to detect localization of the compound in the object of interest. Accordingly, in a patient's body, the nearest proximity of objects still distinguishable from another by molecular imaging may preferably be lower than 1 cm, more preferably lower than 5 mm, in particular lower than 2 mm. In cell culture, the nearest proximity of objects still distinguishable from another by molecular imaging may preferably lower than 2 mm, more preferably lower than 1 mm, in particular lower than 0.5 mm or even in the microscopic range, i.e., lower than 0.1 mm. When performed in a patient's body, molecular imaging may exemplarily be fluorescence molecular tomography (FMT), Optical Imaging or Two-Photon Fluorescence Detection. When performed in cell culture, molecular imaging may exemplarily be fluorescence microscopy, confocal microscopy (e.g., Laser Scanning Microscopy (LSM)), two-photon fluorescence microscopy, Fluorescence Energy Transfer (FRET) based methods, fluorescence correlation spectroscopy (FCS) or fluorescence cross-correlation spectroscopy (FCCS). The imaging may optionally be further combined with other imaging methods such as, e.g., Positron Emission Tomography (PET), Magnetic Resonance Imaging (MRI), radiography (e.g., computed tomography) or Ultrasound Tomography (UT).

The step (iii) of detecting the dye moiety (C), preferably comprising molecular imaging may be conducted subsequent to step (ii) of detecting the radioactive signal of the radiometal, simultaneously to step (ii) or before step (ii).

In a preferred embodiment, step (iii) is conducted subsequent to step (ii).

Before detecting the dye moiety, the artisan may either administer the compound or compound-radiometal complex of the present invention or a pharmaceutically acceptable salt thereof to the patient a further time or may use the fluorescence signal obtainable from said compound, compound-radiometal complex or salt thereof administered once before the preceding detecting of radioactivity signal, such as in particular PET scan.

Both strategies may have some particular advantages. Administering said compound, compound-radiometal complex or salt thereof before the detection of the fluorescence signal a further time, enables to optimize its concentration range in order to obtain a qualitatively good fluorescence signal. Further, a local administration to the neoplastic tissue and its surrounding tissue laid open may be enabled. Such further administration may preferably be administration of the compound, compound-radiometal complex or salt thereof without the radiometal.

On the other hand, administration of said compound, compound-radiometal complex or salt thereof before the detection of the radioactivity signal only, in particular when it is administration only once, prevents the patient of being treated too often and may improve patient's compliance. Further, lower doses of said compound, compound-radiometal complex or salt thereof may prevent undesired possible side-effects thereof. In this case it may be beneficial when the half-live of the radiometal is not too long because then, when the surgical interaction takes place subsequent to the previous molecular imaging via detecting the radioactivity signal, the radioactivity of the radiometal may have been faded to a low and, thus, harmless level, when the surgical interaction actually takes place.

The artisan removing the neoplastic tissue, typically a surgeon, may optionally emit light exciting by the dye moiety during surgery and thereby visualize the neoplastic tissue that is to be removed. This may be performed in intervals or may be performed continuously. Excitation light may result from a standard lamp, from an operational lamp and/or from a headlamp worn by the surgeon and/or any other present person(s). The wavelength of the light may be either such efficiently exciting the dye moiety, in particular a wavelength near the excitation maximum, or the double of said wavelength efficiently exciting the dye moiety (for double-photon excitation), in particular the double of wavelength near the excitation maximum. In a highly preferred embodiment, step (iii) is conducted during surgery, wherein the cancerous tissue is at least partly laid open.

As mentioned before, the method of diagnosing the patient in vivo bases on the use of the composition according to the present invention, thus, on the compound, compound-radiometal complex or pharmaceutically acceptable salt thereof that has complexed the respective radiometal and optionally further comprises a pharmaceutically acceptable carrier. This represents the first and, likewise a specific medical use thereof.

Therefore, in one further aspect, the invention relates to the composition according to the present invention as specified above for use as a medicament, in particular for use as a diagnostic.

In second further aspect, the invention relates to the composition according to the present invention as specified above for use in a method for diagnosing a neoplasm in a patient suffering therefrom or being at risk thereof.

In the context of the composition for use, the definitions of the terms as specified in the context of the compound, compound-radiometal complex or pharmaceutically acceptable salt thereof above and the diagnostic method above also apply.

As mentioned above, in a preferred embodiment, the neoplasia is cancer, in particular prostate cancer.

In a preferred embodiment, the method comprises the following steps:
(i) administering said composition to a patient;
(ii) detecting the radioactive signal of the radiometal, in particular $^{68}$Ga,
preferably wherein step (ii) is conducted by three-dimensional imaging, in particular by means of positron emission tomography (PET).

As mentioned above, in a preferred embodiment, the method further comprises:
(iii) detecting the dye moiety (C), preferably by means of molecular imaging, in particular wherein said step (iii) is conducted subsequent to step (ii).

As mentioned above, the compound or compound-radiometal complex according to the present invention or a pharmaceutically acceptable salt thereof may also be used for detecting a neoplasm in vitro, such as in cell culture or in cells obtained from a patient. In this context, the user of compound, compound-radiometal complex according to the present invention or a pharmaceutically acceptable salt thereof may be also be supplied with said compound or salt thereof in the form of a kit.

Accordingly, a further aspect of the present invention relates to a kit comprising:
(a) the compound according to the present invention or a pharmaceutically acceptable salt thereof as specified above or the composition according to the present invention as specified above; and
(b) a user manual.

In the context of the kit, the definitions of the terms as specified in the context of the compound or pharmaceutically acceptable salt thereof above, the diagnostic method and the composition for use as recited above also apply.

In the context of the present invention, the term "kit" may be understood in the broadest sense as a composition of different products that may be used for performing detecting a neoplasm. The kit may comprise, but may not be limited to the compound or composition according to the present invention or a pharmaceutically acceptable salt thereof, one or more pharmaceutically acceptable carriers, a user manual, syringes, needles, etc. Optionally, the compound according to the present invention or a pharmaceutically acceptable salt thereof or the composition according to the present invention may be dissolved, may be dried or may be freeze-dried. Preferably, the kit of the invention includes a freeze-dried labeled form of the compound or composition according to the present invention or a pharmaceutically acceptable salt thereof, a buffer to dissolve it, an injection or infusion device to mix the compound according to the present invention or a pharmaceutically acceptable salt thereof with the buffer and to administer the mixture to a patient.

The user manual may include instructions on how to store the compound or composition according to the present invention or a pharmaceutically acceptable salt thereof (e.g., temperature, humidity, shelf live etc.), which radiometals to use and, optionally, were to obtain them from, how to complex the compound according to the present invention or a pharmaceutically acceptable salt thereof with the respective radiometal (e.g., buffer conditions) and/or how to use the compound or composition according to the present invention or a pharmaceutically acceptable salt thereof for detecting a neoplasm in vivo and/or in vitro, (e.g., suggested amounts/concentrations, recommended detection techniques etc.).

When the radioactive half-life of the radiometal is sufficiently long enough, the kit may also comprise one or more radiometal(s) suitable to be complexed by the compound of the present invention.

The kit may also be used for and in vitro-detection and investigation of neoplasia.

Accordingly, a still further aspect of the present invention relates to a method for detecting neoplastic cells in a sample in vitro, comprising the following steps:
(i) providing cells which are neoplastic or at risk of being neoplastic, in particular cancerous or at risk of being cancerous;
(ii) administering the compound according to the present invention or a pharmaceutically acceptable salt thereof as specified above or the composition according to the present invention as specified above to said cells;
(iii) detecting the fluorescence and/or radioactive signal of said cells.

In the context of the present in vitro method, the definitions of the terms as specified in the context of the compound or pharmaceutically acceptable salt thereof above, the diagnostic method, the composition for use and the kit as recited above also apply.

The cells which are neoplastic or at risk of being neoplastic may be isolated, i.e., singularized cells or may be cells still present in their physiological context, i.e., in their tissue, which may also comprise different cell types. The cells may be obtained as a tissue sample from a patient who is suffering from a neoplasm or who is at risk of developing neoplasia or may be obtained from a tissue culture. The in vitro sample as used in the context of the present invention may also be a part of or even a whole dead body of a patient or a laboratory animal (e.g., mouse, rat, rabbit etc.).

When cultured the cells may be cultured at suitable conditions, i.e., typically at around 37° C., at a pH of approximately pH 6.5 to 7.5, in particular pH 7.0 to 7.5, with suitable nutrients, vitamins, minerals and, optionally, growth factors. The person skilled in the art will be able to choose a suitable standard cell culture technique suitable for the cells of interest.

Optionally, the cells may be vital during conducting the entire in vitro method. Alternatively, before the step (ii) of administering the compound according to the present invention or a pharmaceutically acceptable salt thereof or the composition according to the present invention to the cells or before step (iii) detecting the fluorescence and/or radioactive signal of said cells, the cells may also be fixed (e.g., is ethanol, acetone, or another fixing agent).

The cells may optionally also be counterstained by other dyes (e.g., DAPI or HOECHT dye for staining the nucleus, and/or a labeled antibody for staining another structure of interest).

In the present in vitro method, the compound or composition according to the present invention or a pharmaceutically acceptable salt thereof may be administered to the cells by preparing a buffer comprising said compound, composition or salt thereof and adding it to the cells. Alternatively, the compound according to the present invention or a pharmaceutically acceptable salt thereof or the composition may also be administered to a patient in vivo and, subsequent a cell and/or tissue sample may be withdrawn from said patient and investigated in vitro.

The present in vitro method particularly enables the consecutive and simultaneous detection of the radioactivity signal from the radiometal and the fluorescence signal from the dye moiety. It will, however, be noted that alternatively optionally also either the one or the other detection method may be used, i.e., only the radioactivity signal from the radiometal or only the fluorescence signal from the dye moiety may be detected. Detecting the fluorescence signal only may allow the omittance of the radiometal what may make handling easier and decrease costs, but may, typically, reduce detection flexibility and data accuracy.

Depending on the employed detection method, before conducting step (iii), the cells may optionally be washed with fresh buffer or cell culture medium in order to remove the excess of unbound compound or compound-radiometal complex.

According to the present invention, neoplastic cells will typically show higher staining rates than corresponding non-neoplastic cells of the same cell type.

The cells may preferably be obtained from a patient, in particular a human.

In a preferred embodiment, the cells are obtained from a patient suffering from or being at risk of a neoplasm preferably cancer, in particular prostate cancer.

Detection may be performed by any means known in the art.

In a preferred embodiment, step (iii) includes detecting fluorescence via microscopic imaging, in particular confocal laser scanning microscopy (LSM) or two-photon microscopy.

Herein, confocal laser scanning microscopy (LSM) or two-photon microscopy may enable the detection of the compound or compound-radiometal complex according to the present invention or a pharmaceutically acceptable salt thereof at the cell surface of cells at the microscopic level. Therefore, comparably small local increases at certain membrane sites may be detectable.

In another preferred embodiment, step (iii) includes detecting fluorescence via a flow cytometer and or fluorescence activated cell sorting (FACS).

Detection via a flow cytometer may enable quantifying the fraction of neoplastic cells versus the fraction of non-neoplastic cells in a sample. Fluorescence activated cell sorting (FACS) may further enable isolating a cell population of interest, such as, e.g., the fraction of neoplastic cells, the fraction of a certain cell type (optionally identified by counterstaining with an antibody typical for a membrane protein of said cells) or the fraction of neoplastic cells of a certain cell type.

In a preferred embodiment, step (iii) includes detecting radioactivity by gamma counting.

As used in the context of the present invention, the term "gamma counting" may be understood in the broadest sense as any method based on the quantification of gamma irradiation. The person skilled in the art will know several methods based on gamma counting and how to conduct these. Exemplarily, gamma counting may be used in the context of a radio-binding assay and/or in a radio-immuno assay (RIA). The readout may be performed by direct gamma counting or by indirect gamma counting such as scintillation counting, in particular liquid scintillation counting. Gamma counting may enable quantifying the fraction of a certain cell type. Further, when combined with a preceding step of isolating a certain cell fraction, e.g., by means of FACS (cf. above), gamma counting may also provide information on the fraction of a specific cells population of interest.

As mentioned above, detecting the fluorescence and detecting radioactive signal (in particular the gamma irradiation) of said cells may be combined with another. Alternatively, only the fluorescence may be detected or only the radioactive signal may be detected.

In any case, when analyzing the data, the cells showing different intensities of fluorescence and/or radioactive signal may be grouped into different fractions. This is typically performed by setting a certain threshold. As mentioned above, according to the present invention, neoplastic cells will typically show higher staining rates, and thus a higher signal intensity compared to corresponding non-neoplastic cells of the same cell type.

Accordingly, in a preferred embodiment, the method further comprises the steps of:
(iv) determining:
   (a) the number of cells above a fluorescence and/or radioactive signal indicating a neoplastic cell, in particular a cancerous cell, and
   (b) the number of cells blow a fluorescence and/or radioactive signal indicating a non-neoplastic cell; and
(v) determining the ratio of (a):(b) and assessing the severity of the neoplastia of the patient the cells have been obtained from.

The number of cells above a fluorescence and/or radioactive signal indicating a neoplastic cell, thus, above a given threshold, show a higher signal intensity compared to corresponding non-neoplastic cells of the same cell type. The person skilled in the art will notice that the signal intensity representing the threshold depends on the investigated cells and the detection method. It may be determined by measuring:
(a) the signal obtained from cells which are known to be neoplastic; and
(b) the signal obtained from corresponding cells which are known to be healthy, i.e., non-neoplastic.

Herein, (a) will typically provide a higher measured intensity than (b). The threshold may be set in between the two measured intensities for (a) and (b).

This may enable to determine assessing the severity of a neoplasm in a patient. A high fraction of cells determined to be neoplastic cells may indicate a severe neoplasia. Therefore, a comparably high fraction of the cells of the investigated tissue are neoplastic, thus, the neoplasm is comparably widespread. In contrast, a low fraction may indicate a less severe neoplasia and the absence of neoplastic cells may indicated the absence of a neoplasm in the investigated tissue sample.

Accordingly, the compound or compound-radiometal complex according to the present invention or a pharmaceutically acceptable salt thereof may also be used for assessing the severity of a neoplasm in a sample in vitro.

Therefore, in a yet further aspect, the present invention relates to the use of the compound according to the present invention or a pharmaceutically acceptable salt thereof as specified above or the composition according to the present invention as specified above for assessing the severity of a neoplasm in a sample in vitro, wherein said sample comprises cells which are neoplastic or at risk of being neoplastic, in particular cancerous or at risk of being cancerous, and which are contacted with said compound or a pharmaceutically acceptable salt thereof or said composition.

In the context of this use, the definitions of the terms as specified throughout the invention above also apply.

In a preferred embodiment, the assessing of the severity of a neoplasm includes determining the ratio of
(a) the number of cells above a fluorescence and/or radioactive signal indicating a neoplastic cell, in particular a cancerous cell, and
(b) the number of cells blow a fluorescence and/or radioactive signal indicating a non-cancerous cell.

The following example are intended to illustrate the invention but not to limit the scope of protection conferred by the claims.
EXAMPLES
Abbreviations
PSMA-(HE)3-HBED-CC-IRdye800CW (Synonym: Glu-urea-Lys-(HE)$_3$-HBED-CC-PEG$_2$-IRDye800CW)
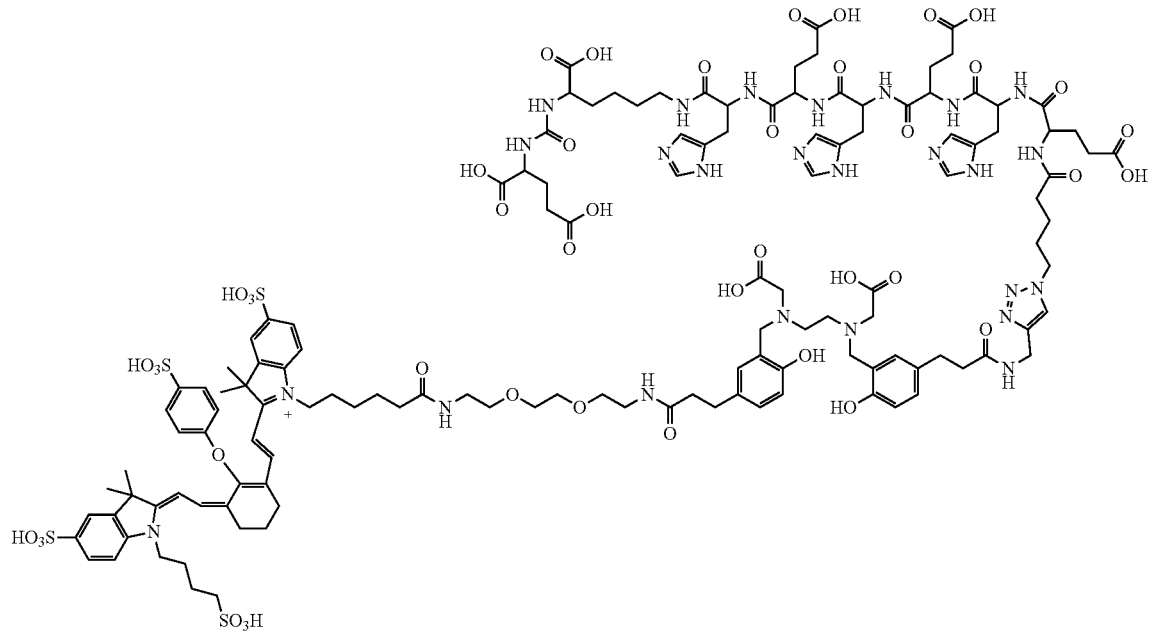
PSMA-(HE)1-HBED-CC-IRdye800CW (Synonym: Glu-urea-Lys-(HE)$_1$-HBED-CC-PEG$_2$-IRDye800CW) (Comparative Example)
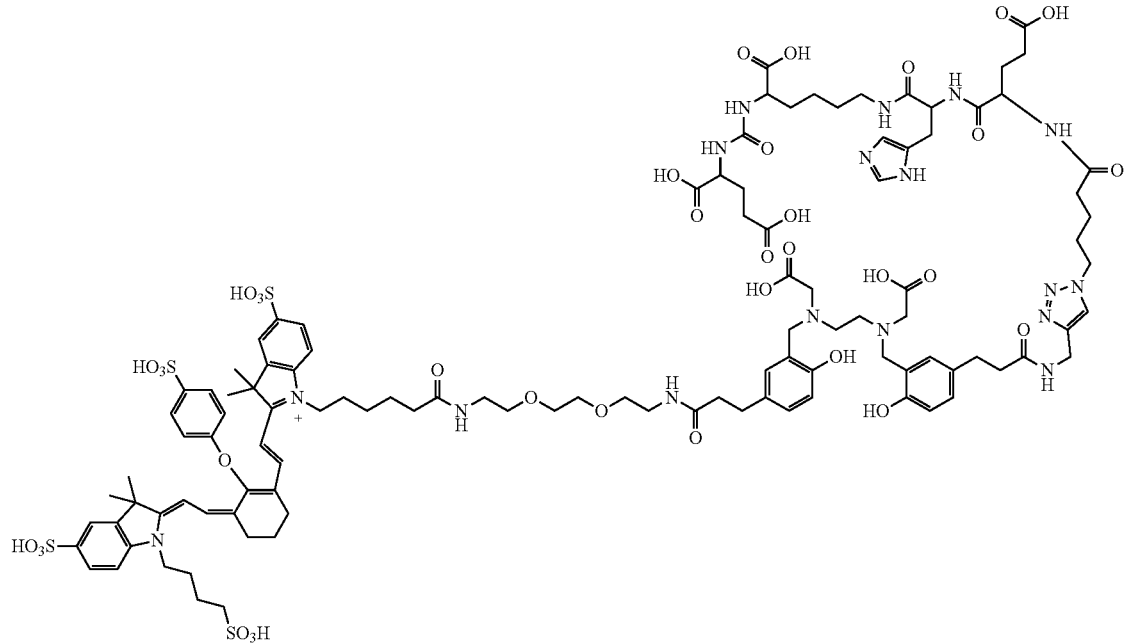

PSMA-(WE)1-HBED-CC-IRdye800CW (Synonym: Glu-urea-Lys-(WE)$_1$-HBED-CC-PEG$_2$-IRDye800CW) (Comparative Example)
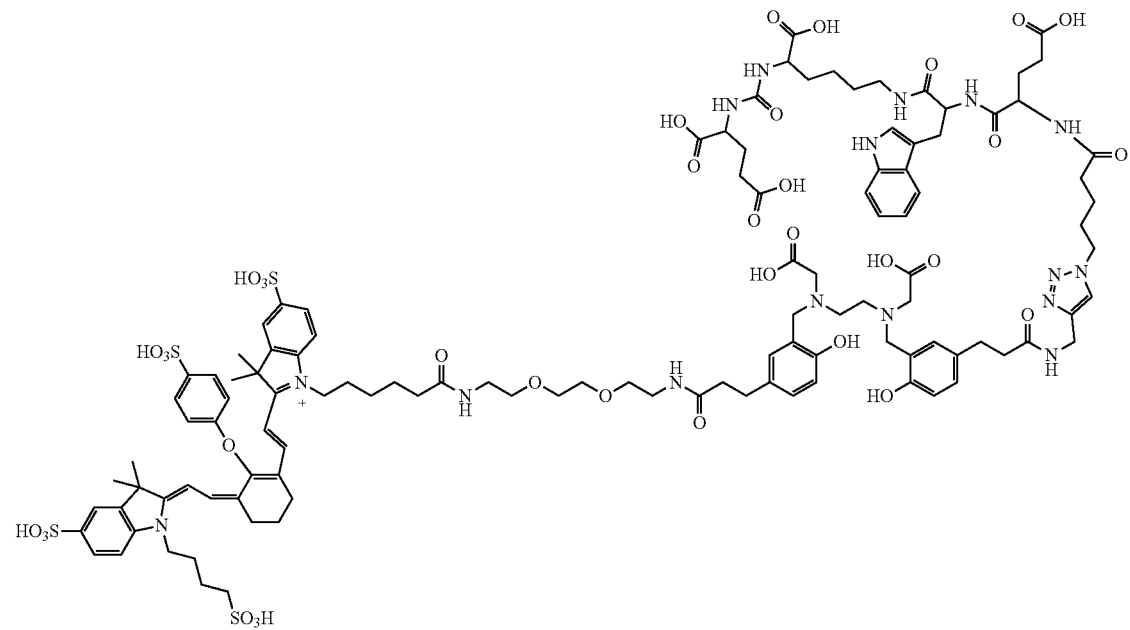
PSMA-HBED-CC-(HE)3-IRDye800CW (Synonym: Glu-urea-Lys-HBED-CC-(HE)$_3$-PEG$_2$-IRDye800CW) (Comparative Example)
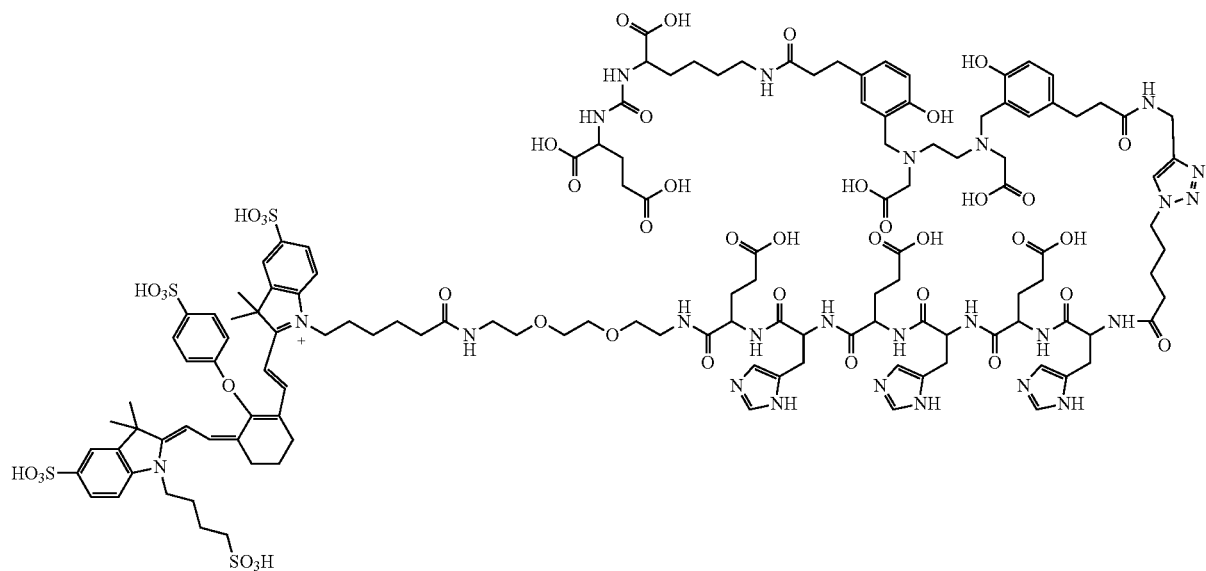

PSMA-HBED-CC-IRDye800CW (Synonym: Glu-urea-Lys-HBED-CC-PEG$_2$-IRDye800CW) (Comparative Example)

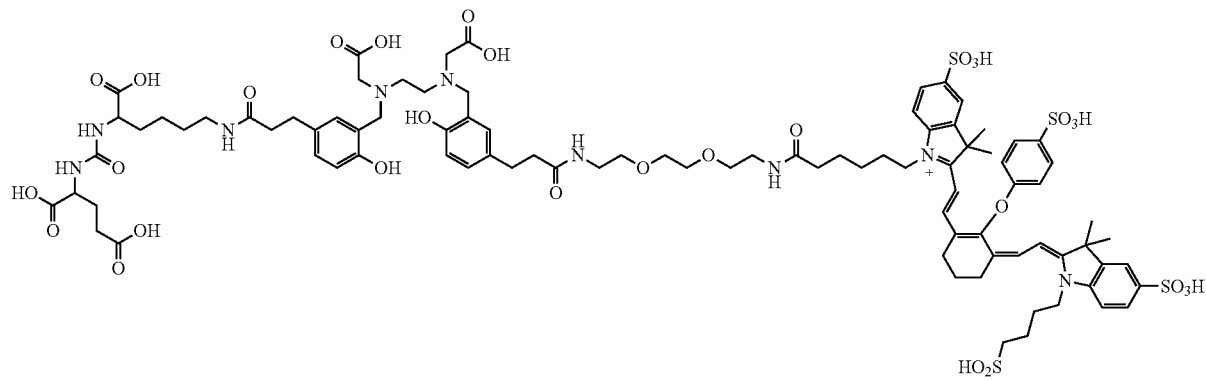

PSMA-HBED-CC (Synonym: PSMA-11, Glu-urea-Lys-(Ahx)-HBED-CC) (Comparative Example)

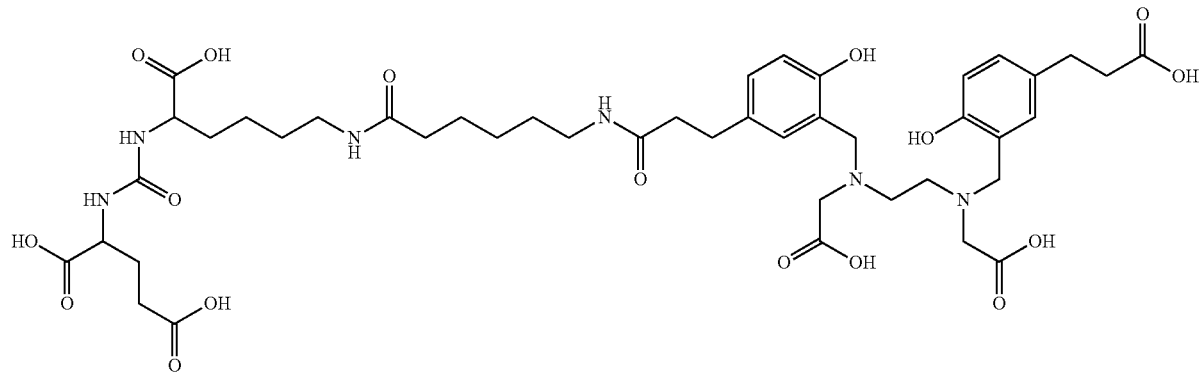 [SMILES: O=C(O)CCc1ccc(O)c(CN(CCN(CC(=O)O)Cc2cc(CCC(=O)NCCCCCC(=O)NCCCCC(NC(=O)NC(CCC(=O)O)C(=O)O)C(=O)O)ccc2O)CC(=O)O)c1]

Experimental Procedures

All commercially available chemicals were of analytical grade and used without further purification. $^{68}$Ga (half-life 68 min; $\beta^+$89%; $E_{\beta+}$ max. 1.9 MeV) was obtained from a $^{68}$Ge/$^{68}$Ga generator based on a pyrogallol resin support (1). The compounds were analyzed using reversed-phase high performance liquid chromatography (RP-HPLC; Chromolith RP-18e, 100×4.6 mm; Merck, Darmstadt, Germany). Analytical HPLC runs were performed using a linear gradient (0.1% aqueous TFA (A) to 100% B (0.1% TFA in CH$_3$CN)) in 10 min at 2 mL/min. The system L6200 A (Merck-Hitachi, Darmstadt, Germany) was equipped with a variable UV and a gamma detector (Bioscan; Washington, USA).

For preparative HPLC the system LaPrep P110 (VWR, Darmstadt, Germany) was supplied with a variable UV detector (P314, VWR, Darmstadt, Germany). Analytical HPLC runs were performed using the system Agilent 1100 series (Agilent Technologies, Santa Clara, Calif., USA). UV absorbance was measured at 214 and 254 nm, respectively. For mass spectrometry a MALDI-MS (Daltonics Microflex, Bruker Daltonics, Bremen, Germany) was used.

Glu-urea-Lys-(Ahx)-HBED-CC (PSMA-11) was purchased from ABX, Radeberg, Germany. PSMA-HBED-CC-PEG$_2$-IRDye800CW was synthesized according to US Patent (Publication number: 20150110715) Double-Labeled Probe for Molecular Imaging and Use Thereof.

Synthesis of Glu-urea-Lys-(HE)$_3$-HBED-CC-PEG$_2$-IRDye800CW

Synthesis of Glu-urea-Lys-(HE)$_3$-CO(CH$_2$)$_4$—N$_3$

The synthesis of the pharmacophore Glu-urea-Lys was performed as described previously (2). Briefly, the synthesis started with the formation of the isocyanate of the glutamyl moiety using triphosgene. A resin-immobilized (2-chlorotritylresin, Merck, Darmstadt) ε-allyloxycarbonyl protected lysine was added and reacted for 16 h with gentle agitation. The resin was filtered off and the allyloxy-protecting group was removed by reacting twice with Pd(PPh$_3$)$_4$ (0.3 eq.) and morpholine (15 eq.) under ambient conditions (1 h, RT). The resin was split and the (HE)$_3$ linker was synthesized by standard Fmoc solid phase protocols. For (HE)$_3$-containing molecules the coupling of Fmoc-His(Trt)-OH, Fmoc-Glu (otBu)-OH and 5-azidopentanoic acid (4 eq.) was performed using HBTU (4 eq.) and DIPEA (4 eq.) in DMF. In order to form (HE)$_3$ the coupling of Fmoc-His(Trt)-OH and Fmoc-Glu(otBu)-OH was repeated, respectively.

The products were cleaved from the resin for 3 hours at RT using TFA/TIPS/H$_2$O (95/2.5/2.5, v/v/v) resulting in the azido-functionalized intermediates. All products were purified using RP-HPLC and identified with mass spectrometry. Purification of Glu-urea-Lys-(HE)$_3$-CO—(CH$_2$)$_4$—N$_3$ was done using a NUCLEODUR® Sphinx RP column (VP250/21, 5 μm 250×21 mm; Macherey-Nagel, Düren, Germany) with a 20 min gradient starting at 10% B, raised to 100% B within 20 min. Solvent A consisted of 0.1% aqueous TFA and solvent B was 0.1% TFA in CH$_3$CN. The flow rate was 20 mL/min.

Synthesis of Glu-urea-Lys-(HE)$_3$-HBED-CC-PEG$_2$

The HBED-CC(TFP)$_2$ was synthesized as previously described by protection using Fe$^{3+}$ and the formation of [Fe(HBED-CC)]$^-$ (3). The bis-TFP ester was isolated with preparative HPLC using a NUCLEODUR® Sphinx RP column with a 20 min gradient starting at 10% B, raised to 100% B in 20 min. Solvent A consisted of 0.1% aqueous TFA and solvent B was 0.1% TFA in CH$_3$CN. The flow rate was 20 mL/min. The product was identified with mass spectrometry (MW: 828.7). [Fe (HBED-CC)] TFP$_2$ and 0.95 eq of Propargylamine were solved in DMF in the presence of DIPEA. After 4 h at room temperature an excess of 2,2'-(ethylenedioxy)bis(ethylamine) (100 μl) was added and stirred for 16 h at RT. The alkenyl-functionalized chelator was purified via preparative HPLC using a NUCLEODUR® Sphinx RP column with a 20 min gradient starting at 10% B, raised to 100% B. Solvent A consisted of 0.1% aqueous TFA and solvent B was 0.1% TFA in CH$_3$CN. The flow rate was 20 mL/min (MW: 699.8).

Subsequently, PEG$_2$-[Fe (HBED-CC)]-propargylamine (1 eq.) was reacted with Glu-urea-Lys-(HE)$_3$-CO(CH$_2$)$_4$—N$_3$ (1 eq.) via CuAAC, CuSO$_4$ (1 eq.), Na-Ascorbate (1 eq.), in 3 mL THF/H$_2$O (1:1, v/v) for 16 h at RT. The Fe-protected product was isolated via preparative HPLC using a NUCLEODUR® Sphinx RP column (0-100% B in 20 min, flow 20 ml/min) and identified with mass spectrometry (MW: 1943.1).

Glu-urea-Lys-(HE)$_3$-HBED-CC-PEG$_2$-IRDye800CW

IRDye800CW-NHS ester (1 eq.) (LI-COR Biosciences) was conjugated to Glu-urea-Lys-(HE)$_3$-[Fe(HBED-CC)]-PEG$_2$ in PBS-buffer (pH 8.5) for 24 h at RT. The Fe-protected product was isolated via semipreparative HPLC using a Chromolith RP-18e column (100×10 mm; Merck, Darmstadt, Germany) (0-100% B in 10 min, flow 5 ml/min) and identified with mass spectrometry (MW: 2929.2).

Complexed Fe$^{3+}$ was removed as described previously (3). Briefly, the Fe-containing product was trapped on a C18 cartridge (Waters SepPak-Classic C18; Waters Corp., Milford, Mass., USA) and was subsequently flushed with 10 mL 1 M HCl and washed with 5 mL H$_2$O. The remaining product was eluted with 2 mL H$_2$O/CH$_3$CN (3:1) and evaporated to dryness.

$^{68}$Ga—Labeling

The precursor peptides [1 nmol in HEPES buffer (580 mg/ml), 90 μL] were added to 40 μL [$^{68}$Ga]Ga$^{3+}$ eluate (~40 MBq). The pH was adjusted to 3.8 using 30% NaOH and 10% NaOH, respectively. The reaction mixture was incubated at 98° C. for 10 minutes. The radiochemical yield (RCY) was determined by HPLC.

Cell Culture

PSMA$^+$ LNCaP cells (ATCC CRL-1740) were cultured in RPMI medium supplemented with 10% fetal calf serum and 2 mmol/L L-glutamine (all from PAA). Cells were grown at 37° C. in humidified air with 5% CO$_2$ and were harvested using trypsin-ethylenediaminetetraacetic acid (trypsin-EDTA; 0.25% trypsin, 0.02% EDTA, Invitrogen).

Cell Binding and Internalization

The competitive cell binding assay and internalization experiments were performed as described previously (4). Briefly, the cells (10$^5$ per well) were incubated with a 0.2 nM solution of $^{68}$Ga-labeled radioligand [Glu-urea-Lys(Ahx)]$_2$-HBED-CC (PSMA-10, precursor ordered from ABX, Radeberg, Germany) in the presence of 12 different concentrations of analyte (0-5000 nM, 100 μL/well). After incubation, the mixture was removed and the wells were washed 3 times with PBS using a multiscreen vacuum manifold (Millipore, Billerica, Mass.). Cell-bound radioactivity was measured using a gamma counter (Packard Cobra II, GMI, Minnesota, USA). The 50% inhibitory concentration (IC50) values were calculated by fitting the data using a nonlinear regression algorithm (GraphPad Software). For internalization experiments, 10$^5$ cells per well were seeded in poly-L-lysine coated 24-well cell culture plates 24 h before incubation. After washing, the cells were incubated with 30 nM of the radiolabeled compound for 45 min at 37° C. and at 4° C., respectively. Cellular uptake was terminated by washing 3 times with 1 mL of ice-cold PBS. To remove surface-bound radioactivity, cells were incubated twice with 0.5 mL glycine-HCl in PBS (50 mM, pH=2.8) for 5 min. The cells were washed with 1 mL of ice-cold PBS and lysed using 0.3 N NaOH (0.5 mL). The surface-bound and the internalized fractions were measured in a gamma counter. The cell uptake was calculated as percent of the initially added radioactivity bound to 10$^5$ cells [% ID/10$^5$ cells].

Biodistribution

For the experimental tumor models 5×10$^6$ cells of LNCaP (in 50% Matrigel; Becton Dickinson, Heidelberg, Germany) were subcutaneously inoculated into the right trunk of 7- to 8-week-old male BALB/c nu/nu mice (Charles River). The tumors were allowed to grow until approximately 1 cm$^3$ in size. The $^{68}$Ga-labeled compounds were injected into a tail vein (1-2 MBq; 60 pmol). At 1 h after injection the animals were sacrificed. Organs of interest were dissected, blotted dry, and weighed. The radioactivity was measured using a gamma counter and calculated as % ID/g. All animal experiments complied with the current laws of the Federal Republic of Germany.

Statistical Aspects

All experiments were performed at least in triplicate and repeated at least for three times. Quantitative data were expressed as mean±SD. If applicable, means were compared using Student's t test. P values <0.05 were considered statistically significant.

Results

The internalization efficiency and the PSMA binding affinity of the conjugates were determined in order to investigate the influence of the linkers on the binding properties. The results are summarized in Table 1. The binding affinity (K) determined on LNCaP cells was slightly reduced from 9.82±1.26 nM PSMA-HBED-CC (PSMA-11) to 17.53±4.98 nM for PSMA-HBED-CC-PEG$_2$-IRDye800CW and 36.70±9.77 nM for PSMA-(HE)$_3$-HBED-CC-PEG$_2$-IRDye800CW.

TABLE 1

Cell binding and internalization data of the investigated conjugates PSMA-HBED-CC-PEG$_2$-IRDye800CW and PSMA-(HE)$_3$-HBED-CC-PEG$_2$-IRDye800CW compared to the reference PSMA-HBED-CC (PSMA-11).

| | $K_i$ [nM] | Specific cell surface bound [% ID/10$^5$ cells] | Specific internalized [% ID/10$^5$ cells] |
|---|---|---|---|
| PSMA-HBED-CC (PSMA-11) | 9.82 ± 1.26 | 2.31 ± 0.61 | 3.57 ± 0.51 |
| PSMA-HBED-CC-PEG$_2$-IRDye8000W | 17.53 ± 4.98 | 13.62 ± 4.79 | 18.70 ± 7.03 |
| PSMA-(HE)$_3$-HBED-CC-PEG$_2$-IRDye800CW | 36.70 ± 9.77 | 8.30 ± 3.93 | 6.45 ± 3.36 |

The specific cell surface binding and specific internalization of PSMA-HBED-CC-PEG$_2$-IRDye800CW and PSMA-(HE)$_3$-HBED-CC-PEG$_2$-IRDye800CW were improved as compared to the reference structure PSMA-11.

The higher PSMA-specific internalization of the conjugates observed in these assays resulted in a significant higher tumor accumulation of 13.66±3.73% ID/g (PSMA-HBED-CC-PEG$_2$-IRDye800CW) and 7.59±0.95% ID/g (PSMA-(HE)$_3$-HBED-CC-PEG$_2$-IRDye800CW) as compared to the reference (4.89±1.34% ID/g (PSMA-11); P<0.05) shown by organ distribution using LNCaP-tumor bearing nude mice (Table 2). PSMA-(HE)$_3$-HBED-CC-PEG$_2$-IRDye800CW showed a lower uptake in all background organs as compared to PSMA-HBED-CC-PEG$_2$-IRDye800CW. Through the introduction of (HE)$_3$ the spleen uptake was extremely reduced from 38.12±14.62% ID/g (PSMA-HBED-CC-PEG$_2$-IRDye800CW) to 3.47±1.39% ID/g (PSMA-(HE)$_3$-HBED-CC-PEG$_2$-IRDye800CW).

TABLE 2

Organ distribution of $^{68}$Ga labeled PSMA-11, PSMA-HBED-CC-PEG$_2$-IRDye800CW and PSMA-(HE)$_3$-HBED-CC-PEG$_2$-IRDye800CW in LNCaP-tumor bearing balb/c nu/nu mice 1 h p.i. (n = 3).

| | PSMA-11 | | PSMA-HBED-CC-PEG$_2$-IRDye800CW | | PSMA-(HE)$_3$-HBED-CC-PEG$_2$-IRDye800CW | |
|---|---|---|---|---|---|---|
| | Mean | SD | Mean | SD | Mean | SD |
| Blood | 0.53 | 0.04 | 3.04 | 1.36 | 1.12 | 0.64 |
| Heart | 0.83 | 0.08 | 2.78 | 0.83 | 1.36 | 0.37 |
| Lung | 2.36 | 0.27 | 5.60 | 1.79 | 2.34 | 0.37 |
| Spleen | 17.88 | 2.87 | 38.12 | 14.62 | 3.47 | 1.39 |
| Liver | 1.43 | 0.19 | 2.76 | 0.51 | 1.25 | 0.18 |
| Kidney | 139.44 | 21.40 | 204.98 | 56.24 | 109.27 | 10.33 |
| Muscle | 1.00 | 0.24 | 2.86 | 0.88 | 1.18 | 0.15 |
| Intestine | 1.14 | 0.46 | 2.41 | 0.72 | 1.31 | 0.00 |
| Brain | 0.40 | 0.19 | 0.43 | 0.14 | 0.18 | 0.02 |
| Tumor | 4.89 | 1.34 | 13.66 | 3.73 | 7.59 | 0.95 |

TABLE 3

Tumor-to-Organ ratio of $^{68}$Ga labeled PSMA-11, PSMA-HBED-CC-PEG$_2$-IRDye800CW and PSMA-(HE)$_3$-HBED-CC-PEG$_2$-IRDye800CW in LNCaP-tumor bearing balb/c nu/nu mice 1 h p.i. (n = 3).

| | PSMA-11 | PSMA-HBED-CC-PEG$_2$-IRDye8000W | PSMA-(HE)$_3$-HBED-CC-PEG$_2$-IRDye8000W |
|---|---|---|---|
| T/Blood | 9.23 | 4.49 | 6.80 |
| T/Heart | 5.89 | 4.92 | 5.57 |
| T/Lung | 2.07 | 2.44 | 3.24 |
| T/Spleen | 0.27 | 0.36 | 2.19 |
| T/Liver | 3.42 | 4.94 | 6.08 |
| T/Kidney | 0.04 | 0.07 | 0.07 |
| T/Muscle | 4.89 | 4.78 | 6.45 |
| T/Intestine | 4.29 | 5.66 | 5.80 |
| T/Brain | 12.23 | 31.39 | 42.63 |

In order to evaluate the influence of the (HE)$_3$ linker introduction on the uptake in background organs, tumor-to-organ ratios were calculated and summarized in Table 3. Compared to PSMA-HBED-CC-PEG$_2$-IRDye800CW, the linker bearing compound PSMA-(HE)$_3$-HBED-CC-PEG$_2$-IRDye800CW showed a higher T/O-ratio for all organs except kidney, clearly indicating an improved pharmacokinetic profile.

Noticeably, localizing the (HE)$_3$ as linker between the binding motif and the chelator resulted in a clear reduction of the spleen signal.

To compare the influence of the (HE)$_3$ linker introduction to other amino acid linkers at different positions, their uptake in background organs were determined and the tumor-to-organ ratios calculated. The data is summarized in and Table 4.

Tables 4a and 4b. Organ distribution of $^{68}$Ga labeled PSMA-11, PSMA-HBED-CC-PEG$_2$-IRDye800CW, PSMA-(HE)$_3$-HBED-CC-PEG$_2$-IRDye800CW; PSMA-HBED-CC-(HE)$_3$-PEG$_2$-IRDye800CW, PSMA-(HE)$_1$-HBED-CC-PEG$_2$-IRDye800CW and PSMA-(WE)$_1$-HBED-CC-PEG$_2$-IRDye800CW in LNCaP-tumor bearing balb/c nu/nu mice 1 h p.i. (n=3).

TABLE 4a

| | PSMA-11 | | PSMA-HBED-CC-PEG$_2$-IRDye8000W | | PSMA-(HE)$_3$-HBED-CC-PEG$_2$-IRDye8000W | |
|---|---|---|---|---|---|---|
| | Mean | SD | Mean | SD | Mean | SD |
| Blood | 0.53 | 0.04 | 3.04 | 1.36 | 1.12 | 0.64 |
| Heart | 0.83 | 0.08 | 2.78 | 0.83 | 1.36 | 0.37 |
| Lung | 2.36 | 0.27 | 5.60 | 1.79 | 2.34 | 0.37 |
| Spleen | 17.88 | 2.87 | 38.12 | 14.62 | 3.47 | 1.39 |
| Liver | 1.43 | 0.19 | 2.76 | 0.51 | 1.25 | 0.18 |
| Kidney | 139.44 | 21.40 | 204.98 | 56.24 | 109.27 | 10.33 |
| Muscle | 1.00 | 0.24 | 2.86 | 0.88 | 1.18 | 0.15 |
| Intestine | 1.14 | 0.46 | 2.41 | 0.72 | 1.31 | 0.00 |
| Brain | 0.40 | 0.19 | 0.43 | 0.14 | 0.18 | 0.02 |
| Tumor | 4.89 | 1.34 | 13.66 | 3.73 | 7.59 | 0.95 |

TABLE 4b

| | PSMA-(HE)$_3$-HBED-CC-PEG$_2$-IRDye800CW | | PSMA-HBED-CC-(HE)$_3$-PEG$_2$-IRDye800CW | | PSMA-(HE)$_1$-HBED-CC-PEG$_2$-IRDye800CW | | PSMA-(WE)$_1$-HBED-CC-PEG$_2$-IRDye800CW | |
|---|---|---|---|---|---|---|---|---|
| | Mean | SD | Mean | SD | Mean | SD | Mean | SD |
| Blood | 1.12 | 0.64 | 0.80 | 0.31 | 1.52 | 0.64 | 1.61 | 0.55 |
| Heart | 1.36 | 0.37 | 0.57 | 0.26 | 0.94 | 0.14 | 1.49 | 0.51 |
| Lung | 2.34 | 0.37 | 1.78 | 1.19 | 2.46 | 0.46 | 2.57 | 1.01 |
| Spleen | 3.47 | 1.39 | 8.88 | 2.93 | 8.17 | 0.23 | 12.94 | 2.00 |
| Liver | 1.25 | 0.18 | 0.72 | 0.05 | 1.19 | 0.30 | 1.73 | 0.61 |
| Kidney | 109.27 | 10.33 | 92.54 | 21.07 | 84.34 | 2.13 | 104.58 | 20.79 |
| Muscle | 1.18 | 0.15 | 0.97 | 0.38 | 1.03 | 0.34 | 1.00 | 0.37 |
| Intestine | 1.31 | 0.00 | 0.65 | 0.21 | 1.29 | 0.36 | 0.96 | 0.37 |
| Brain | 0.18 | 0.02 | 0.18 | 0.06 | 0.30 | 0.10 | 0.15 | 0.04 |
| Tumor | 7.59 | 0.95 | 3.32 | 1.51 | 3.92 | 0.31 | 3.85 | 1.10 |

PSMA-(HE)$_3$-HBED-CC-PEG$_2$-IRDye800CW (7.59±0.95% ID/g) showed a significant higher tumor uptake compared to other linker bearing compounds (PSMA-HBED-CC-(HE)$_3$-PEG$_2$-IRDye800CW: 3.32±1.51% ID/g, PSMA-(HE)$_1$-HBED-CC-PEG$_2$-IRDye800CW: 3.92±0.31% ID/g, PSMA-(WE)$_1$-HBED-CC-PEG$_2$-IRDye800CW: 3.85±1.10% ID/g). The spleen uptake of PSMA-(HE)$_3$-HBED-CC-PEG$_2$-IRDye800CW is extremely reduced as compared to all other compounds represented in Table 4.

The tumor-to-organ ratios (Table 5) of for all background organs are the highest for PSMA-(HE)$_3$-HBED-CC-PEG$_2$-IRDye800CW (except T/heart: 5.57 vs PSMA-HBED-CC-(HE)$_3$-PEG$_2$-IRDye800CW T/heart: 5.80).

TABLE 5

Tumor-to-Organ ratio of $^{68}$Ga labeled PSMA-11, PSMA-HBED-CC-PEG$_2$-IRDye800CW, PSMA-(HE)$_3$-HBED-CC-PEG$_2$-IRDye800CW; PSMA-HBED-CC-(HE)$_3$-PEG$_2$-IRDye800CW, PSMA-(HE)$_1$-HBED-CC-PEG$_2$-IRDye800CW and PSMA-(WE)$_1$-HBED-CC-PEG$_2$-IRDye800CW in LNCaP-tumor bearing balb/c nu/nu mice 1 h p.i. (n = 3).

| | PSMA-11 | PSMA-HBED-CC-PEG$_2$-IRDye800CW | PSMA-(HE)$_3$-HBED-CC-PEG$_2$-IRDye800CW | PSMA-HBED-CC-(HE)$_3$-PEG$_2$-IRDye800CW | PSMA-(HE)$_1$-HBED-CC-PEG$_2$-IRDye800CW | PSMA-(WE)$_1$-HBED-CC-PEG$_2$-IRDye800CW |
|---|---|---|---|---|---|---|
| T/Blood | 9.23 | 4.49 | 6.80 | 4.12 | 2.58 | 2.39 |
| T/Heart | 5.89 | 4.92 | 5.57 | 5.80 | 4.19 | 2.59 |
| T/Lung | 2.07 | 2.44 | 3.24 | 1.86 | 1.60 | 1.50 |
| T/Spleen | 0.27 | 0.36 | 2.19 | 0.37 | 0.48 | 0.30 |
| T/Liver | 3.42 | 4.94 | 6.08 | 4.60 | 3.30 | 2.23 |
| T/Kidney | 0.04 | 0.07 | 0.07 | 0.04 | 0.05 | 0.04 |
| T/Muscle | 4.89 | 4.78 | 6.45 | 3.43 | 3.81 | 3.86 |
| T/Intestine | 4.29 | 5.66 | 5.80 | 5.13 | 3.05 | 4.01 |
| T/Brain | 12.23 | 31.39 | 42.63 | 18.15 | 13.01 | 25.56 |

To further analyze the pharmacokinetic influence of the (HE)$_3$ linker, additional organ distribution studies at 2 h p.i. with the favourable $^{68}$Ga-labeled compound PSMA-(HE)$_3$-HBED-CC-PEG$_2$-IRDye800CW in comparison to $^{68}$Ga labeled PSMA-11 PSMA-HBED-CC-PEG$_2$-IRDye800CW were performed (Table 6).

TABLE 6

Organ distribution of $^{68}$Ga labeled PSMA-11, PSMA-HBED-CC-PEG$_2$-IRDye800CVV, PSMA-(HE)$_3$-HBED-CC-PEG$_2$-IRDye800CW in LNCaP-tumor bearing balb/c nu/nu mice 2 h p.i. (n = 3).

|  | PSMA-11 | | PSMA-HBED-CC-PEG$_2$-IRDye8000W | | PSMA-(HE)$_3$-HBED-CC-PEG$_2$-IRDye8000W | |
| --- | --- | --- | --- | --- | --- | --- |
|  | Mean | SD | Mean | SD | Mean | SD |
| Blood | 0.32 | 0.14 | 0.76 | 0.23 | 0.65 | 0.01 |
| Heart | 0.31 | 0.01 | 1.00 | 0.11 | 0.53 | 0.08 |
| Lung | 1.19 | 0.11 | 2.53 | 0.27 | 0.89 | 0.05 |
| Spleen | 12.41 | 0.7 | 13.73 | 1.63 | 0.76 | 0.16 |
| Liver | 0.34 | 0.05 | 1.21 | 0.05 | 0.76 | 0.11 |
| Kidney | 129.73 | 13.77 | 119.56 | 5.13 | 55.81 | 9.76 |
| Muscle | 2.06 | 0.36 | 1.96 | 0.57 | 0.47 | 0.11 |
| Intestine | 1.19 | 0.35 | 1.37 | 0.27 | 0.67 | 0.17 |
| Brain | 0.23 | 0.05 | 0.22 | 0.01 | 0.23 | 0.15 |
| Tumor | 6.09 | 0.71 | 7.94 | 0.19 | 3.10 | 1.17 |

Introduction of (HE)$_3$ between PSMA-binding motif and chelator resulted in rapid clearance from background organs. Especially, kidney and spleen uptake was reduced compared to the other compounds.

REFERENCES (1) Schuhmacher, J., and Maier-Borst, W. (1981) A new Ge-68/Ga-68 radioisotope generator system for production of Ga-68 in dilute HCl. *Int J Appl Radiat Isot* 32, 31-36.

(2) Schafer, M., Bauder-Wust, U., Leotta, K., Zoller, F., Mier, W., Haberkorn, U., Eisenhut, M., and Eder, M. (2012) A dimerized urea-based inhibitor of the prostate-specific membrane antigen for 68Ga-PET imaging of prostate cancer. *EJNMMI Res* 2, 23.

(3) Eder, M., Wangler, B., Knackmuss, S., Legall, F., Little, M., Haberkorn, U., Mier, W., and Eisenhut, M. (2008) Tetrafluorophenolate of HBED-CC: a versatile conjugation agent for (68)Ga-labeled small recombinant antibodies. *Eur J Nucl Med Mol Imaging* 35, 1878-86.

(4) Eder, M., Schafer, M., Bauder-Wust, U., Hull, W. E., Wangler, C., Mier, W., Haberkorn, U., and Eisenhut, M. (2012) (68)Ga-Complex Lipophilicity and the Targeting Property of a Urea-Based PSMA Inhibitor for PET Imaging. *Bioconjug Chem* 23, 688-97.

The invention claimed is:

1. A compound or a pharmaceutically acceptable salt thereof of formula (I):

(A)-$x_1$-(B)-$x_2$-(C), wherein
(A) is at least one motif specifically binding to cell membranes of neoplastic cells;
(B) at least one chelator moiety of radiometals;
(C) a dye moiety;
$x_1$ is a spacer covalently connecting (A) and (B);
$x_2$ is a spacer or a chemical single bond connecting (B) and (C);
wherein the dye moiety (C) has the formula

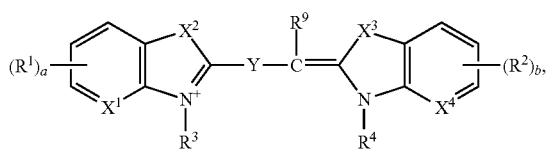

wherein
$X^1$ and $X^4$ are independently selected from the group consisting of —N=, —N($R^5$)=, and —C($R^6$)=;
$X^2$ and $X^3$ are independently selected from the group consisting of O, S, Se, N($R^5$), and C($R^6R^7$);
Y is a linker connecting the two moieties of (C) and permitting electron delocalization between said moieties, wherein Y optionally comprises a group (L-)$_c Z^0$;
a and b are independently selected from the group consisting of 1, 2, and 3;
each $R^1$ and each $R^2$ is independently (L-)$_c Z$, (L-)$_c Z^0$ or H; and two adjacent $R^1$ and/or two adjacent $R^2$ can also form an aromatic ring, which is optionally substituted with one or more (L-)$_c Z$ or (L-)$_c Z^0$;
$R^3$, $R^4$, $R^5$, $R^6$, $R^7$, $R^9$ are independently selected from the group consisting of (L-)$_c Z$, (L-)$_c Z^0$, and H;
each c is independently 0, or 1;
each L is independently $T^1$, —O$T^1$-, —S$T^1$-, —C(O)$T^1$-, —C(O)O$T^1$-, —OC(O)$T^1$-, —C(O)NH$T^1$-, —NHC(O)$T^1$-, or a $C_{1-10}$ alkylene group, which is optionally interrupted and/or terminated by one or more of —O—, —S—, —C(O)—, —C(O)O—, —OC(O)—, —C(O)NH—, —NHC(O)O—, and $T^1$;
$T^1$ is phenyl, naphthyl, indenyl, indanyl, tetralinyl, decalinyl, adamantyl, $C_{3-7}$ cycloalkyl, 3 to 7 membered heterocyclyl, or 7 to 11 membered heterobicyclyl, wherein $T^1$ is optionally substituted with one or more substituents selected from the group consisting of halogen, CN, C(O)$R^8$, COO$R^8$, O$R^8$, C(O)N($R^8R^{8a}$), S(O)$_2$N($R^8R^{8a}$), S(O)N($R^8R^{8a}$), S(O)$_2R^8$, N($R^8$)S(O)$_2$N($R^{8a}R^{8b}$), S$R^8$, N($R^8R^{8a}$), NO$_2$; OC(O)$R^8$, N($R^8$)C(O)$R^{8a}$, N($R^8$)S(O)$_2R^{8a}$, N($R^8$)S(O)$R^{8a}$, N($R^8$)C(O)N($R^{8a}R^{8b}$), N($R^8$)C(O)O$R^{8a}$, OC(O)N($R^8R^{8a}$), oxo (=O), where the ring is at least partially saturated, or $C_{1-6}$ alkyl, wherein $C_{1-6}$ alkyl is optionally substituted with one or more halogen, which are the same or different;

each Z is independently H, halogen, CN, C(O)$R^8$, C(O)O$R^8$, C(O)O$^-$ O$R^8$, C(O)N($R^8R^{8a}$), S(O)$_2$O$R_8$, S(O)$_2$O$^-$, S(O)$_2$N($R^8R^{8a}$), S(O)N($R^8R^{8a}$), S(O)$_2R^8$, S(O)$R^8$, N($R^8$)S(O)$_2$N($R^{8a}R^{8b}$), S$R^8$, N($R^8R^{8a}$), NO$_2$; P(O)(O$R^8$)$_2$, P(O)(O$R^8$)O$^-$, OC(O)$R^8$, N($R^8$)C(O)$R^{8a}$, N($R^8$)S(O)$_2R^{8a}$, N($R^8$)S(O)$R^{8a}$, N($R^8$)C(O)N($R^{8a}R^{8b}$), N($R^8$)C(O)O$R^{8a}$, or OC(O)N($R^8R^{8a}$);

$R^8$, $R^{8a}$, $R^{8b}$ are independently selected from the group consisting of H, or $C_{1-6}$ alkyl, wherein $C_{1-6}$ alkyl is optionally substituted with one or more halogen, which are the same or different;

$Z^0$ is a chemical bond connecting (C) to $x_2$ or to (B) in case $x_2$ is a chemical single bond;

provided that one of $R^1$, $R^2$, $R^3$, $R^4$, $R^5$, $R^6$, $R^7$, $R^9$ is (L-)$_c Z^0$ or that Y comprises (L-)$_c Z^0$;

wherein $x_1$ comprises a group -AA-, wherein AA is an amino acid sequence of 4 to 8 naturally occurring amino acids and wherein at least two amino acids are histidine and wherein any remaining positive or negative charge or charges are compensated by pharmaceutically acceptable negatively or positively charged counterion or counterions.

2. The compound or a pharmaceutically acceptable salt thereof of claim 1, wherein said compound has a molecular weight of not more than 10 kDa.

3. The compound or a pharmaceutically acceptable salt thereof of claim 1, wherein the motif specifically binding to cell membranes of neoplastic cells (A) is a motif specifically binding to cell membranes of cancerous cells.

4. The compound or a pharmaceutically acceptable salt thereof according to claim 3, wherein the motif specifically binding to cell membranes of neoplastic cells (A) is a PSMA binding motif having the following structure:

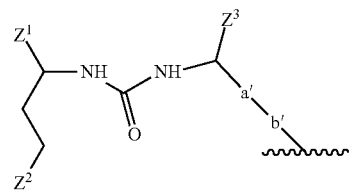

wherein $Z^1$, $Z^2$ and $Z^3$ are each independently from another selected from the group consisting of —C(O)O$R^{1a}$, —SO$_2R^{1a}$, —SO$_3R^{1a}$, —SO$_4R^{1a}$, —PO$_2R^{1a}$, —PO$_3R^{1a}$, and —PO$_4R^{1a}R^{2a}$, wherein $R^{1a}$ and $R^{2a}$ are independently from another H or a $C_{1-4}$-alkyl residue;

wherein a' represents a —[CH$_2$]$_o$— residue, wherein o is an integer from 1 to 4;

wherein b' represents a residue selected from the group consisting of —NH—, —C(O)— and —O—; and wherein the wavy line indicates the conjugation site to the chelator moiety of radiometals (B), conjugated via a spacer molecule x$_1$.

5. The compound or a pharmaceutically acceptable salt thereof of claim 4, wherein a' represents a —[CH$_2$]$_o$— residue, wherein o is 3 or 4; or wherein b' is —NH—.

6. The compound or a pharmaceutically acceptable salt thereof of claim 5, wherein o is 4.

7. The compound or a pharmaceutically acceptable salt thereof of claim 1, wherein the motif specifically binding to cell membranes of neoplastic cells (A) is a PSMA binding motif having the following structure:

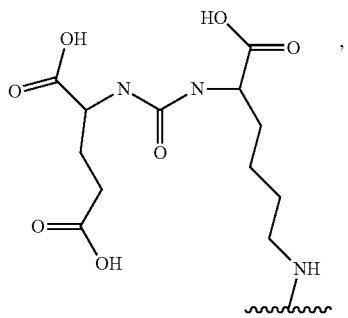 [SMILES: *NCCCCC(NC(=O)NC(CCC(=O)O)C(=O)O)C(=O)O]

wherein the wavy line indicates the conjugation site to the chelator moiety of radiometals (B), conjugated via a spacer molecule x$_1$.

8. The compound or pharmaceutically acceptable salt thereof of claim 1, wherein AA comprises three histidine amino acids.

9. The compound or pharmaceutically acceptable salt thereof of claim 1, wherein AA consists of histidine and glutamic acid.

10. The compound or pharmaceutically acceptable salt thereof of claim 1, wherein AA is represented by the formula -His-Glu-His-Glu-His-Glu-.

11. The compound or pharmaceutically acceptable salt thereof of claim 1 wherein the C-terminus or the N-terminus, of AA forms an amide bond with (A).

12. The compound or a pharmaceutically acceptable salt thereof of claim 11, wherein AA comprises a histidine.

13. The compound or a pharmaceutically acceptable salt thereof according to claim 1, wherein the spacer x$_1$ bears the following structure:

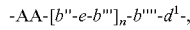

wherein b'' is —C(O)— or —N(H);

wherein e represents a residue selected from the group consisting of an C$_{1-8}$-alkylene wherein one or more —CH$_2$— moieties may optionally be replaced by one or more —O—, —S—, —C(O)NH— —C(O)N(C$_{1-6}$ alkyl), —C(O)O—, succinimide, triazole, wherein b''' is selected from the group consisting of —NH—, and —C(O)—;

wherein b'''' is selected from the group consisting of —C(O)—, and —NH—;

and wherein b''' and b'''' or a terminus of AA, and b'''' together form an amide group;

wherein d$^1$ is —[CH$_2$]$_p$—, wherein p is 1 or 2; and wherein n is 0 or 1.

14. The compound or a pharmaceutically acceptable salt thereof of claim 13, wherein b'' is —C(O)—; wherein e is without any replacement, or with one, two or three replacements wherein the N-terminus of AA, and b'''' together form an amide group; wherein d$^1$ is —[CH$_2$]$_p$—, wherein p is 2; or wherein n is 1.

15. The compound or a pharmaceutically acceptable salt thereof of claim 14, wherein b'' forms an amide bond with AA.

16. The compound or a pharmaceutically acceptable salt thereof of claim 14, wherein e is with one replacement.

17. The compound or a pharmaceutically acceptable salt thereof of claim 16, wherein the replacement is triazole.

18. The compound or a pharmaceutically acceptable salt thereof of claim 16, wherein e is C$_6$ alkylene with one replacement.

19. The compound or a pharmaceutically acceptable salt thereof of claim 13, wherein e is a residue selected from the group consisting of an unsubstituted C$_{1-8}$-alkylene, C$_{4-8}$ alkylene where one —CH$_2$— is replaced by triazole, C$_{1-6}$ alkylene, where one —CH$_2$—is replaced by triazole, —CH$_2$—(O—CH$_2$—CH$_2$)$_2$—CH$_2$—, —(CH$_2$)$_2$—(O—CH$_2$—CH$_2$)$_2$—, —(CH$_2$)$_3$—O—CH$_2$—CH$_2$—O—CH$_2$—, —CH$_2$—O—(CH$_2$)$_6$—, —(CH$_2$)$_2$—O—(CH$_2$)$_5$—, —(CH$_2$)$_3$—O—(CH$_2$)$_4$—, —(CH$_2$)$_4$—O—(CH$_2$)$_3$—, —(CH$_2$)$_5$—O—(CH$_2$)$_2$—, —(CH$_2$)$_6$—O—CH$_2$—, —CH$_2$—(O—CH$_2$—CH$_2$)$_2$—, —(CH$_2$)$_2$—O—CH$_2$—CH$_2$—O—CH$_2$—, —CH$_2$—O—(CH$_2$)$_5$—, —(CH$_2$)$_2$—O—(CH$_2$)$_4$—, —(CH$_2$)$_3$—O—(CH$_2$)$_3$—, —(CH$_2$)$_4$—O—(CH$_2$)$_2$—, —(CH$_2$)$_5$—O—CH$_2$—, —CH$_2$—O—CH$_2$—CH$_2$—O—CH$_2$—, —CH$_2$—O—(CH$_2$)$_4$—, —(CH$_2$)$_2$—O—(CH$_2$)$_3$—, —(CH$_2$)$_3$—O—(CH$_2$)$_2$—, —(CH$_2$)$_4$—O—CH$_2$—, —CH$_2$—O—(CH$_2$)$_3$—, —(CH$_2$)$_2$—O—(CH$_2$)$_2$—, —(CH$_2$)$_3$—O—CH$_2$—, —CH$_2$—O—(CH$_2$)$_2$—, —(CH$_2$)$_2$—O—CH$_2$—, and —CH$_2$—O—CH$_2$—.

20. The compound or a pharmaceutically acceptable salt thereof of claim 13, wherein e is a residue selected from the group consisting of a butylene residue, a pentylene residue a hexylene residue and C$_{4-8}$ alkylene, where one —CH$_2$— is replaced by triazole.

21. The compound of claim 1, wherein (A)-x$_1$- is represented by the following structure:

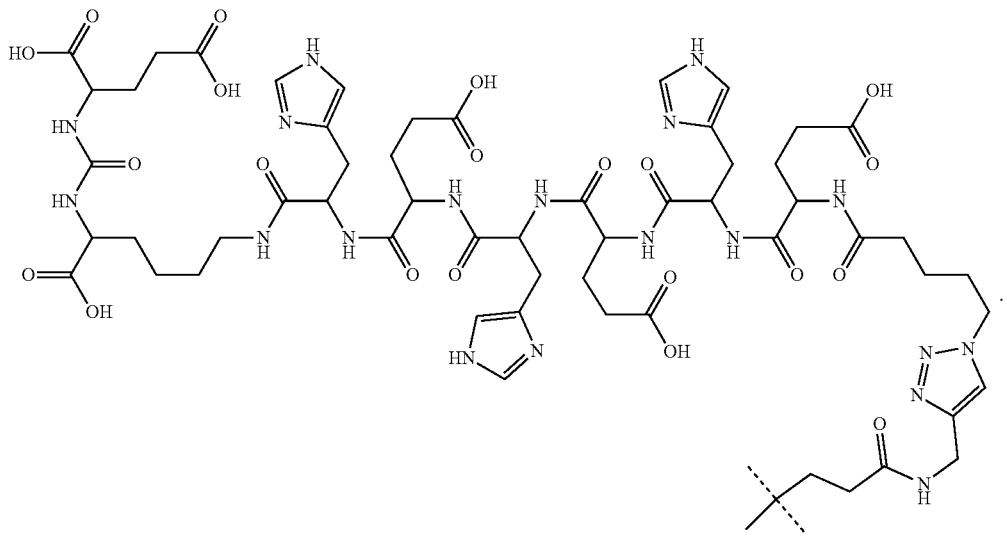

22. The compound or a pharmaceutically acceptable salt thereof according to claim 1, wherein the spacer $x_2$ bears the following structure:

-$d^2$-$e'$-[$f$-$e''$]$_m$- wherein $d^2$ is —[CH$_2$]$_r$—, wherein r is 1 or 2; and
wherein e' is selected from the group consisting of —C(O)—NH—, —NH—C(O)—, —C(O)—O— and —O—C(O)—, —NH—C(O)—NH—, —NH—C(S)—NH—,

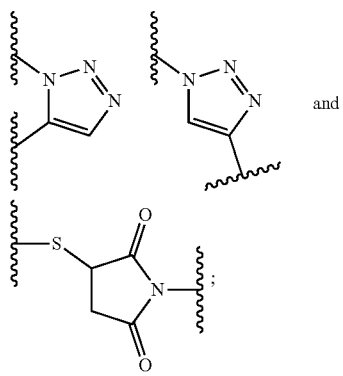 and wherein one of the wavy lines indicates the conjugation site to $d^2$ and the other wavy line indicates the conjugation site to f,
wherein each f independently represents a residue selected from the group consisting of an C$_{1-10}$-alkylene wherein one or more —CH$_2$— moieties may optionally be replaced by —O— or —NH—, and wherein f is unsubstituted or substituted with one or more groups independently selected from the group consisting of —NH$_2$, —COOH and R$^{3a}$,
wherein R$^{3a}$ is selected from the group consisting of —(CH$_2$)$_2$—COOH, —(CH$_2$)$_4$—NH$_2$, —(CH$_2$)$_4$—N$^+$(CH$_3$)$_3$+X$^-$, —CH$_2$—COOH, —CH$_2$—SH, —CH$_2$—SO$_3$H, and

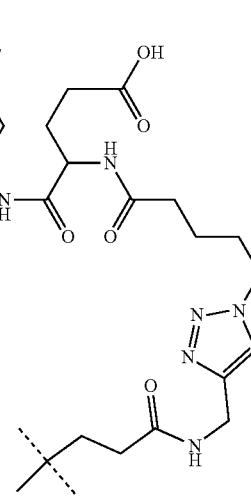

wherein X$^-$ is a pharmaceutically acceptable negatively charged counterion;
wherein each e'' is independently selected from the group consisting of a chemical bond, —NH—C(O)—, —C(O)—NH—, —C(O)—O— and —O—C(O)—, —NH—C(O)—NH—, —NH—C(S)—NH—, —C(O)—N(CH$_3$)—, —N(CH$_3$)—C(O)—, —NH—C(S)—, —C(S)—NH—,

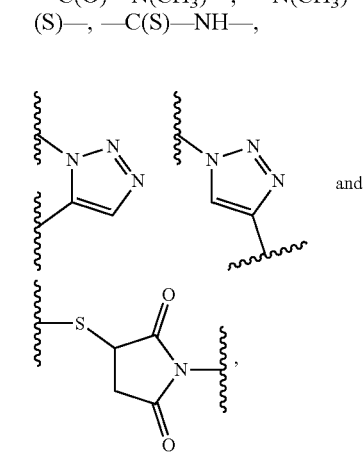

wherein one of the wavy lines indicates the conjugation site to f and the other wavy line indicates the conjugation site to the at least one dye moiety (C); and
wherein m indicates an integer from 0 to 8.

23. The compound or a pharmaceutically acceptable salt thereof of claim 22, wherein the spacer $x_2$ bears one of the following structures:
—(CH$_2$)$_t$—C(O)—NH—(CH$_2$)$_u$—(O—CH$_2$—CH$_2$)$_v$—(CH$_2$)$_w$-e''-, or
—(CH$_2$)$_t$—C(O)—NH—(CH$_2$—CH$_2$—O)$_v$—CH$_2$-e''-
wherein t is 1 or 2; wherein u is an integer from 1 to 10; wherein v is an integer from 0 to 3;

wherein w is an integer from 0 to 2.

24. The compound or a pharmaceutically acceptable salt thereof according to claim 23, wherein the spacer $x_2$ bears one of the following structures:

—$(CH_2)_2$—C(O)—NH—$(CH_2)_2$—(O—$CH_2$—$CH_2)_2$-e''-,

—$(CH_2)_2$—C(O)—NH—$(CH_2)_2$—(O—$CH_2$—$CH_2)_2$—NH—C(O)—$CH_2$—(O—$CH_2$—$CH_2)_{n'}$—O—$CH_2$-e''-,

—$(CH_2)_2$—C(O)—NH—$(CH_2)_2$—(O—$CH_2$—$CH_2)_2$—NH—[C(O)—CH$((CH_2)_2$COOH)—NH]$_{n''}$—C(O)—CH$((CH_2)_2$COOH)-e''-,

—$(CH_2)_2$—C(O)—NH—$(CH_2)_2$—(O—$CH_2$—$CH_2)_2$—NH—[C(O)—CH$((CH_2)_4NH_2)$—NH]$_{n''}$—C(O)—CH$((CH_2)_4NH_2)$-e''-, or

—$(CH_2)_2$—C(O)—NH—$(CH_2)_2$—(O—$CH_2$—$CH_2)_2$—NH—[C(O)—CH$((CH_2)_4N^+(CH_3)_3)$—NH]$_{n''}$—C(O)—CH$((CH_2)_4N^+(CH_3)_3)$-e''-+$X^-$, wherein n' is an integer from 1 to 3; wherein n'' is an integer from 0 to 2;

wherein $X^-$ is a pharmaceutically acceptable negatively charged counterion; and wherein each e'' is independently selected from the group consisting of a chemical bond, —NH—C(O)—, —C(O)—NH—, —C(O)—O— and —O—C(O)—, —NH—C(O)—NH—, —NH—C(S)—NH—, —C(O)—N(CH$_3$)—, —N(CH$_3$)—C(O)—, —NH—C(S)—, —C(S)—NH—,

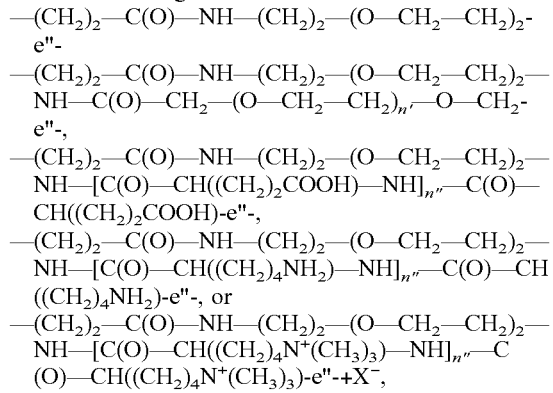

and

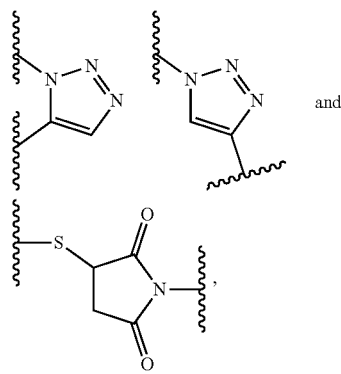

wherein one of the wavy lines indicates the conjugation site to f and the other wavy line indicates the conjugation site to the at least one dye moiety (C).

25. The compound or a pharmaceutically acceptable salt thereof of claim 24, wherein e'' is —NH—C(O)—.

26. The compound or a pharmaceutically acceptable salt thereof of claim 23, wherein t is 2;
wherein u is an integer from 1 to 3; wherein v is 2; or wherein w is 0.

27. The compound or a pharmaceutically acceptable salt thereof of claim 23, wherein u is 2.

28. The compound or a pharmaceutically acceptable salt thereof of claim 22, wherein $d^2$ is —[CH$_2$]$_r$—, wherein r is 2; wherein e' is —C(O)—NH—;
wherein f is selected from the group consisting of —CH$_2$—(O—CH$_2$—CH$_2$)$_2$—CH$_2$—, —(CH$_2$)$_2$—(O—CH$_2$—CH$_2$)$_2$—, —(CH$_2$)$_2$—(CH$_2$—CH$_2$—O)$_2$(CH$_2$)$_2$—, —(CH$_2$)$_3$—(CH$_2$—CH$_2$—O)$_2$—CH$_2$—, —(CH$_2$—CH$_2$—O)$_3$—CH$_2$—, —(CH$_2$)$_2$—(CH$_2$—CH$_2$—O)$_2$—CH$_2$—, —(CH$_2$)$_2$—(CH$_2$—CH$_2$—NH)$_2$—(CH$_2$)$_2$—, —(CH$_2$)$_3$—(CH$_2$—CH$_2$—NH)$_2$—CH$_2$—, —(CH$_2$—CH$_2$—NH)$_3$—CH$_2$—, —(CH$_2$)$_2$—(CH$_2$—CH$_2$—NH)$_2$—CH$_2$—, —(CH$_2$)$_3$—O—CH$_2$—CH$_2$—O—CH$_2$—, —CH$_2$—O—(CH$_2$)$_6$—, —(CH$_2$)$_2$—O—(CH$_2$)$_5$—, —(CH$_2$)$_3$—O—(CH$_2$)$_4$—, —(CH$_2$)$_4$—O—(CH$_2$)$_3$—, —(CH$_2$)$_5$—O—(CH$_2$)$_2$—, —(CH$_2$)$_6$—O—CH$_2$—, —CH$_2$—(O—CH$_2$—CH$_2$)$_2$—, —(CH$_2$)$_2$—O—CH$_2$—CH$_2$—O—CH$_2$—, —CH$_2$—O—(CH$_2$)$_5$—, —(CH$_2$)$_2$—O—(CH$_2$)$_4$—, —(CH$_2$)$_3$—O—(CH$_2$)$_3$—, —(CH$_2$)$_4$—O—(CH$_2$)$_2$—, —(CH$_2$)$_5$—O—CH$_2$—, —CH$_2$—O—CH$_2$—CH$_2$—O—CH$_2$—, —CH$_2$—O—(CH$_2$)$_4$—, —(CH$_2$)$_2$—O—(CH$_2$)$_3$—, —(CH$_2$)$_3$—O—(CH$_2$)$_2$—, —(CH$_2$)$_4$—O—CH$_2$—, —CH$_2$—O—(CH$_2$)$_3$—, —(CH$_2$)$_2$—O—(CH$_2$)$_2$—, —(CH$_2$)$_3$—O—CH$_2$—, —CH$_2$—O—(CH$_2$)$_2$—, —(CH$_2$)$_2$—O—CH$_2$—, —CH$_2$—O—CH$_2$—, —(CH$_2$)$_3$—(O—CH$_2$—CH$_2$)$_2$—CH$_2$—, —(CH$_2$)$_2$—(O—CH$_2$—CH$_2$)$_2$—(CH$_2$)$_2$, —CH$_2$—(O—CH$_2$—CH$_2$)$_2$—(CH$_2$)$_3$, —CH$_2$—(O—CH$_2$—CH$_2$)$_3$—, —(CH$_2$)$_2$—(O—CH$_2$—CH$_2$)$_2$—CH$_2$—, —CH$_2$—(O—CH$_2$—CH$_2$)$_2$—(CH$_2$)$_2$—, and —(CH$_2$)$_3$—(O—CH$_2$—CH$_2$)$_2$—, CH$_2$—(NH—CH$_2$—CH$_2$)$_2$—CH$_2$—, —(CH$_2$)$_2$—(NH—CH$_2$—CH$_2$)$_2$—, —(CH$_2$)$_3$—NH—CH$_2$—CH$_2$—NH—CH$_2$—, —CH$_2$—NH—(CH$_2$)$_6$—, —(CH$_2$)$_2$—NH—(CH$_2$)$_5$—, —(CH$_2$)$_3$—NH—(CH$_2$)$_4$—, —(CH$_2$)$_4$—NH—(CH$_2$)$_3$—, —(CH$_2$)$_5$—NH—(CH$_2$)$_2$—, —(CH$_2$)$_6$—NH—CH$_2$—, —CH$_2$—(NH—CH$_2$—CH$_2$)$_2$—, —(CH$_2$)$_2$—NH—CH$_2$—CH$_2$—NH—CH$_2$—, —CH$_2$—NH—(CH$_2$)$_5$—, —(CH$_2$)$_2$—NH—(CH$_2$)$_4$—, —(CH$_2$)$_3$—NH—(CH$_2$)$_3$—, —(CH$_2$)$_4$—NH—(CH$_2$)$_2$—, —(CH$_2$)$_5$—NH—CH$_2$—, —CH$_2$—NH—CH$_2$—CH$_2$—NH—CH$_2$—, —CH$_2$—NH—(CH$_2$)$_4$—, —(CH$_2$)$_2$—NH—(CH$_2$)$_3$—, —(CH$_2$)$_3$—NH—(CH$_2$)$_2$—, —(CH$_2$)$_4$—NH—CH$_2$—, —CH$_2$—NH—(CH$_2$)$_3$—, —(CH$_2$)$_2$—NH—(CH$_2$)$_2$—, —(CH$_2$)$_3$—NH—CH$_2$—, —CH$_2$—NH—(CH$_2$)$_2$—, —(CH$_2$)$_2$—NH—CH$_2$—, —CH$_2$—NH—CH$_2$—, —(CH$_2$)$_3$—(NH—CH$_2$—CH$_2$)$_2$—CH$_2$—, —(CH$_2$)$_2$(NH—CH$_2$—CH$_2$)$_2$—(CH$_2$)$_2$, —CH$_2$—(NH—CH$_2$—CH$_2$)$_2$—(CH$_2$)$_3$, —CH$_2$—(NH—CH$_2$—CH$_2$)$_3$—, —(CH$_2$)$_2$—(NH—CH$_2$—CH$_2$)$_2$—CH$_2$—, —CH$_2$—(NH—CH$_2$—CH$_2$)$_2$—(CH$_2$)$_2$—, —(CH$_2$)$_3$—(NH—CH$_2$—CH$_2$)$_2$—, —CH$_2$—O—(CH$_2$)$_8$—, —(CH$_2$)$_2$—O—(CH$_2$)$_7$—, —(CH$_2$)$_3$—O—(CH$_2$)$_6$—, —(CH$_2$)$_4$—O—(CH$_2$)$_5$—, —(CH$_2$)$_5$—O—(CH$_2$)$_4$—, —(CH$_2$)$_6$—O—(CH$_2$)$_3$—, —(CH$_2$)$_7$—O—(CH$_2$)$_2$—, —(CH$_2$)$_8$—O—CH$_2$—, —CH$_2$—O—(CH$_2$)$_7$—, —(CH$_2$)$_2$—O—(CH$_2$)$_6$—, —(CH$_2$)$_3$—O—(CH$_2$)$_5$—, —(CH$_2$)$_4$—O—(CH$_2$)$_4$—, —(CH$_2$)$_5$—O—(CH$_2$)$_3$—, —(CH$_2$)$_6$—O—(CH$_2$)$_2$—, —(CH$_2$)$_7$—O—CH$_2$—, —CH$_2$—NH—(CH$_2$)$_8$—, —(CH$_2$)$_2$—NH—(CH$_2$)$_7$—, —(CH$_2$)$_3$—NH—(CH$_2$)$_6$—, —(CH$_2$)$_4$—NH—(CH$_2$)$_5$—, —(CH$_2$)$_5$—NH—(CH$_2$)$_4$—, —(CH$_2$)$_6$—NH—(CH$_2$)$_3$—, —(CH$_2$)$_7$—NH—(CH$_2$)$_2$—, —(CH$_2$)$_8$—NH—CH$_2$—, —CH$_2$—NH—(CH$_2$)$_7$—, —(CH$_2$)$_2$—NH—(CH$_2$)$_6$—, —(CH$_2$)$_3$—NH—(CH$_2$)$_5$—, —(CH$_2$)$_4$—NH—(CH$_2$)$_4$—, —(CH$_2$)$_5$—NH—(CH$_2$)$_3$—, —(CH$_2$)$_6$—NH—(CH$_2$)$_2$—, —(CH$_2$)$_7$—NH—CH$_2$—, —CH(NH$_2$)—CH$_2$—, —CH$_2$—CH(NH$_2$)—, —CH(COOH)—CH$_2$—, —CH$_2$—CH(COOH), and —CH(R$^3$)—, wherein e'' is —NH—C(O)—; or wherein m indicates an integer from 0 to 4.

29. The compound or a pharmaceutically acceptable salt thereof of claim 28, wherein f is a residue selected from the group consisting of —(CH$_2$)$_2$—(O—CH$_2$—CH$_2$)$_2$—, —CH$_2$—(O—CH$_2$—CH$_2$)$_2$—CH$_2$—, and —(CH$_2$)$_3$—O—CH$_2$—CH$_2$—O—CH$_2$—.

30. The compound or a pharmaceutically acceptable salt thereof of claim 28, wherein m indicates an integer from 0 to 2.

31. The compound or a pharmaceutically acceptable salt thereof of claim 28, wherein m indicates an integer from 0 to 1.

32. The compound or a pharmaceutically acceptable salt thereof of claim 28, wherein m is 1.

33. The compound or a pharmaceutically acceptable salt thereof according to claim 1, wherein the chelator moiety of radiometals (B) is selected from the group consisting of:

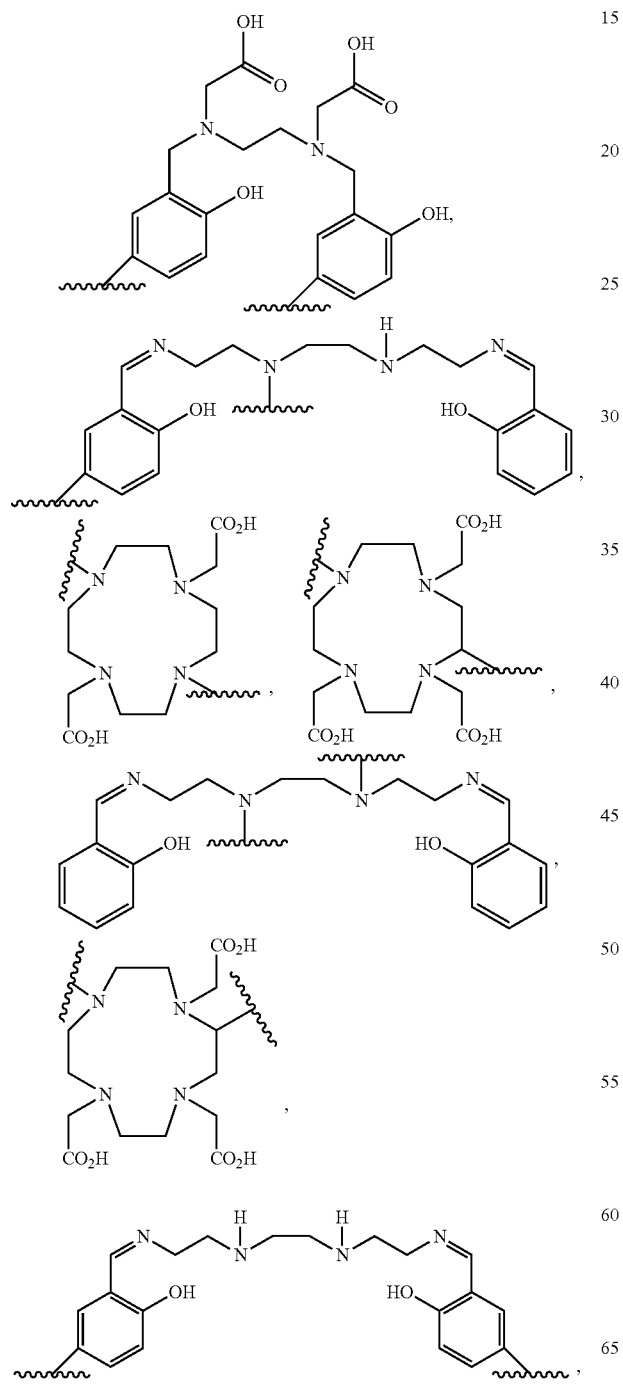

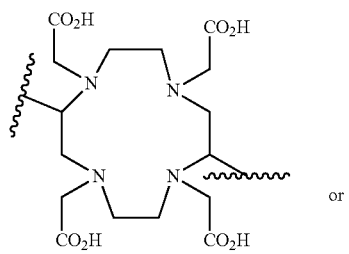

or

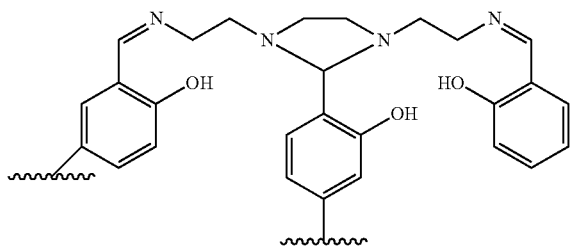

wherein in each of the chelator moieties one of the wavy lines indicates the conjugation site to the at least one motif specifically binding to cell membranes of neoplastic cells (A) via a spacer $x_1$, and the other wavy line indicates the conjugation site to the at least one dye moiety (C).

34. The compound or a pharmaceutically acceptable salt thereof of claim 33, wherein in each of the chelator moieties one of the wavy lines indicates the conjugation site to the at least one motif specifically binding to cell membranes of neoplastic cells (A) via a spacer $x_1$, and the other wavy line indicates the conjugation site to the at least one dye moiety (C) via the spacer $x_2$; or wherein the chelator moiety is

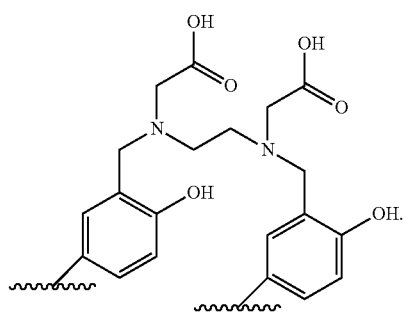 [SMILES: *c1ccc(O)c(CN(CCN(CC(=O)O)Cc2cc(*)ccc2O)CC(=O)O)c1]

35. The compound or a pharmaceutically acceptable salt thereof according to claim 1, wherein (A)-$x_1$-(B)-$x_2$- is represented by the following structure:

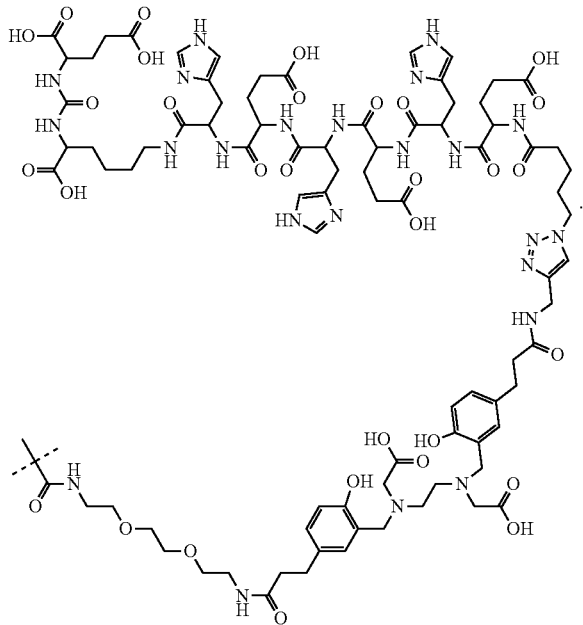

36. The compound or a pharmaceutically acceptable salt thereof according to claim 1, wherein the dye moiety (C) $X^1$ and $X^4$ are the same.

37. The compound or a pharmaceutically acceptable salt thereof according to claim 36, wherein the dye moiety (C) $X^1$ and $X^4$ are $C(R^6)$.

38. The compound or a pharmaceutically acceptable salt thereof according to claim 36, wherein the dye moiety (C) $X^1$ and $X^4$ are CH.

39. The compound or a pharmaceutically acceptable salt thereof according to claim 1, wherein the dye moiety (C) $X^2$ and $X^3$ are the same.

40. The compound or a pharmaceutically acceptable salt thereof according to claim 39, wherein the dye moiety (C) $X^2$ and $X^3$ are $C(R^6R^7)$.

41. The compound or a pharmaceutically acceptable salt thereof according to claim 40, wherein $R^6$ and $R^7$ are the same.

42. The compound or a pharmaceutically acceptable salt thereof according to claim 40, wherein $R^6$ and $R^7$ are L-Z with L=$C_{1-10}$ alkylene and Z=H.

43. The compound or a pharmaceutically acceptable salt thereof according to claim 42, wherein L is $CH_2$.

44. The compound or a pharmaceutically acceptable salt thereof according to claim 1, wherein the dye moiety (C) Y does not comprise $(L-)_c Z^0$.

45. The compound or a pharmaceutically acceptable salt thereof according to claim 44, wherein Y is

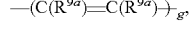

wherein g is 1, 2, 3, or 4 and each $R^{9a}$ is $(L-)_c Z$, or H; and two $R^{9a}$ can also form a carbocyclic ring having 5, 6, or 7 carbon atoms or a 4 to 7 membered heterocyclic ring;

each c is independently 0, or 1;

each L is independently $T^1$, —$OT^1$-, —$ST^1$-, —C(O)$T^1$-, —C(O)O$T^1$-, —OC(O)$T^1$-, —C(O)NH$T^1$-, —NHC(O) $T^1$, or a $C_{1-10}$ alkylene group, which is optionally interrupted and/or terminated by one or more of —O—, —S—, —C(O)—, —C(O)O—, —OC(O)—, —C(O)NH—, —NHC(O)O—, and $T^1$;

$T^1$ is phenyl, naphthyl, indenyl, indanyl, tetralinyl, decalinyl, adamantyl, $C_{3-7}$ cycloalkyl, 4 to 7 membered heterocyclyl, or 7 to 11 membered heterobicyclyl, wherein $T^1$ is optionally substituted with one or more substituents selected from the group consisting of halogen, CN, C(O)$R^8$, COO$R^8$, O$R^8$, C(O)N($R^8R^{8a}$), S(O)$_2$N($R^8R^{8a}$), S(O)N($R^8R^{8a}$), S(O)$_2R^8$, N($R^8$) S(O)$_2$N($R^{8a}R^{8b}$), S$R^8$, N($R^8R^{8a}$), NO$_2$; OC(O)$R^8$, N($R^8$)C(O)$R^{8a}$, N($R^8$)S(O)$_2R^{8a}$, N($R^8$)S(O)$R^{8a}$, N($R^8$) C(O)N($R^{8a}R^{8b}$), N($R^8$)C(O)O$R^{8a}$, OC(O)N($R^8R^{8a}$), oxo (=O), where the ring is at least partially saturated, or $C_{1-6}$ alkyl, wherein $C_{1-6}$ alkyl is optionally substituted with one or more halogen, which are the same or different;

$R^8$, $R^{8a}$, $R^{8b}$ are independently selected from the group consisting of H, or $C_{1-6}$ alkyl, wherein $C_{1-6}$ alkyl is optionally substituted with one or more halogen, which are the same or different; and each Z is independently H, halogen, CN, C(O)$R^8$, C(O) O$R^8$, C(O)O$^-$ O$R^8$, C(O)N($R^8R^{8a}$), S(O)$_2$O$R_8$, S(O)$_2$O$^-$, S(O)$_2$N($R^8R^{8a}$), S(O)N($R^8R^{8a}$), S(O)$_2R^8$, S(O)$R^8$, N($R^8$)S(O)$_2$N($R^{8a}R^{8b}$), S$R^8$, N($R^8R^{8a}$), NO$_2$; P(O)(O$R^8$)$_2$, P(O)(O$R^8$)O$^-$, OC(O)$R^8$, N($R^8$)C(O)$R^{8a}$, N($R^8$)S(O)$_2R^{8a}$, N($R^8$)S(O)$R^{8a}$, N($R^8$)C(O)N($R^{8a}R^{8b}$), N($R^8$)C(O)O$R^{8a}$, or OC(O)N($R^8R^{8a}$); or Y is selected from:

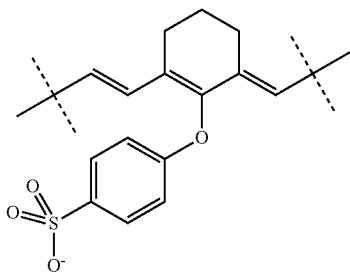

or —$(C(R^{9a})=C(R^{9a}))_g$— with g=2 and each $R^{9a}$=H.

46. The compound or a pharmaceutically acceptable salt thereof according to claim 1, wherein the dye moiety (C) a and b are the same.

47. The compound or a pharmaceutically acceptable salt thereof according to claim 1, wherein the dye moiety (C) a and b are 2.

48. The compound or a pharmaceutically acceptable salt thereof according to claim 1, wherein the dye moiety (C) one of $R^3$ and $R^4$ is $(L-)_c Z^{Z0}$ and the other is $(L-)_c Z$ with L-=$C_{1-10}$ alkylene and Z=H or $SO_3$—.

49. The compound or a pharmaceutically acceptable salt thereof according to claim 48, wherein c=1.

50. The compound or a pharmaceutically acceptable salt thereof of claim 1, wherein $(L-)_c Z^{Z0}$ is $C_{1-10}$ alkylene connecting (C) to $x_2$ or to (B) in case $x_2$ is a chemical single bond.

51. The compound or a pharmaceutically acceptable salt thereof of claim 1, wherein the dye moiety (C) is selected from the group consisting of the following structures:

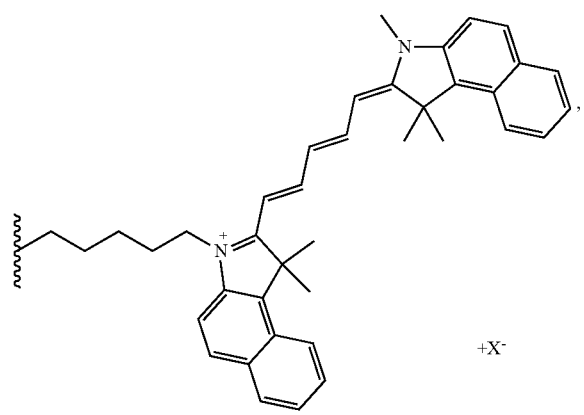

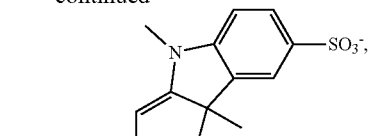

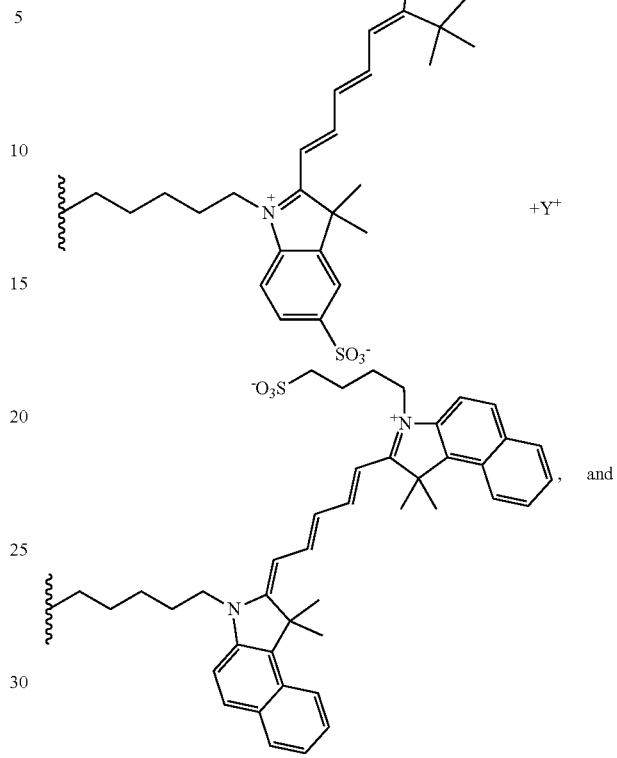

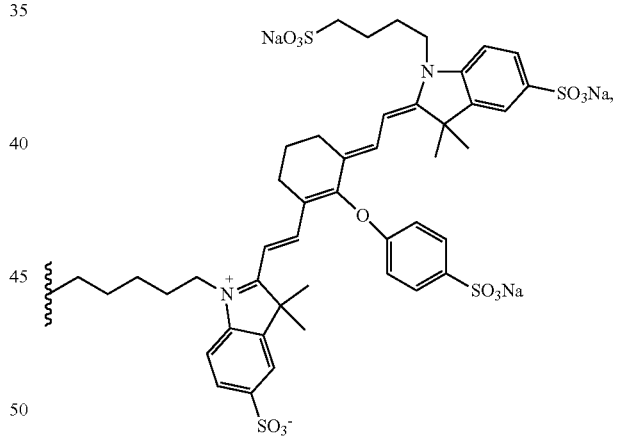

wherein X⁻ is a pharmaceutically acceptable negatively charged counterion;

wherein Y+ is a pharmaceutically acceptable positively charged counterion; and wherein the wavy line indicates the conjugation site to the rest of the compound.

52. The compound of claim 1, wherein in the dye moiety (C) is a fluorescent dye moiety having an emission maximum in the range from 400 nm to 1000 nm.

53. The compound or a pharmaceutically acceptable salt thereof of claim 1, wherein said compound has the following chemical structure, wherein the positive charge is compensated by a pharmaceutically acceptable negatively charged counterion:

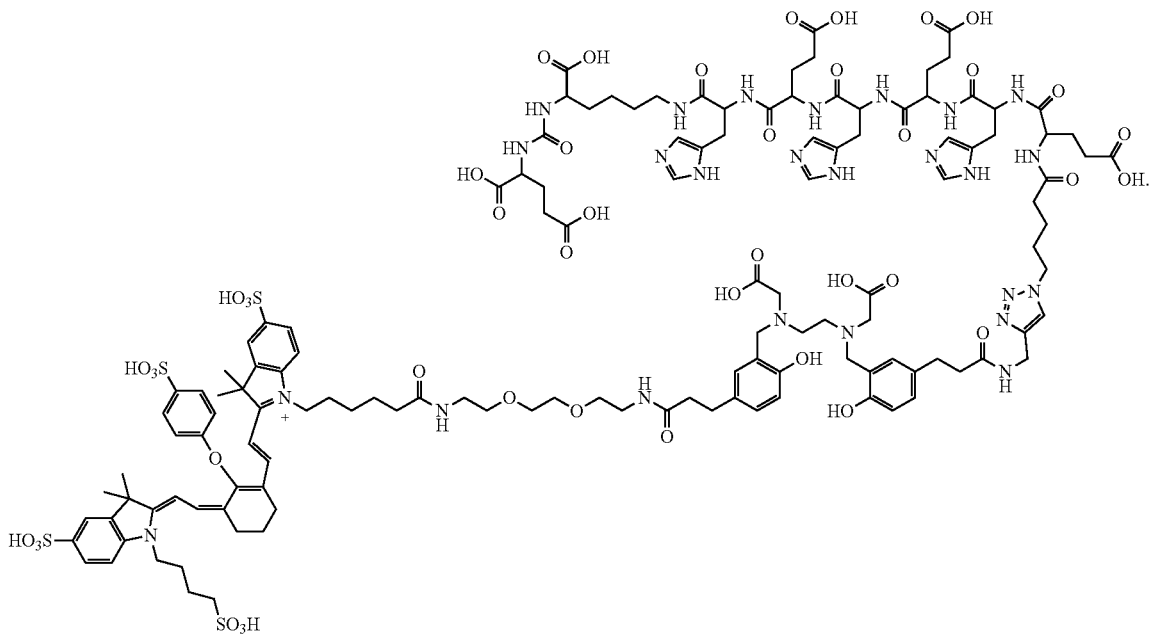

54. A composition comprising:
(a) the compound or a pharmaceutically acceptable salt thereof of claim 1;
(b) a radiometal; and optionally
(c) one or more pharmaceutically acceptable carriers.

55. The composition of claim 54, wherein the radiometal is selected from the group consisting of $^{89}$Zr, $^{44}$Sc, $^{111}$In, $^{90}$Y, $^{67}$Ga, $^{68}$Ga, $^{177}$Lu, $^{99m}$Tc, $^{82}$Rb, $^{64}$Cu, $^{67}$Cu, $^{153}$Gd, $^{155}$Gd, $^{157}$Gd, $^{213}$Bi, $^{225}$Ac and $^{59}$Fe.

56. The composition of claim 54, wherein the radiometal is $^{68}$Ga.

57. A method for detecting neoplastic cells in a sample in vitro, comprising the following steps:
(i) providing cells which are neoplastic or at risk of being neoplastic;
(ii) administering the compound or a pharmaceutically acceptable salt thereof according to claim 1 to said cells;
(iii) detecting the fluorescence and/or radioactive signal of said cells.

58. The method of claim 57, wherein the cells which are neoplastic or at risk of being neoplastic are cancerous or at risk of being cancerous.

59. The compound or a pharmaceutically acceptable salt thereof of claim 1, wherein AA is an amino acid sequence of 5 to 7 naturally occurring amino acids and wherein at least two amino acids are histidine.

60. The compound or a pharmaceutically acceptable salt thereof of claim 1, wherein AA is an amino acid sequence of 6 naturally occurring amino acids and wherein at least two amino acids are histidine.

61. The compound or a pharmaceutically acceptable salt thereof of claim 1, wherein said compound has a molecular weight of not more than 5 kDa.

62. The compound or a pharmaceutically acceptable salt thereof of claim 1, wherein the motif specifically binding to cell membranes of neoplastic cells (A) comprises a prostate-specific membrane antigen (PSMA) binding motif.

63. The compound or pharmaceutically acceptable salt thereof of claim 1 wherein the C-terminus of AA forms an amide bond with (A).

64. The compound or a pharmaceutically acceptable salt thereof according to claim 1, wherein the dye moiety (C) a and b are 1.

65. The compound or a pharmaceutically acceptable salt thereof according to claim 1, wherein the dye moiety (C) $R^1$ and $R^2$=$SO_3$—.

66. The compound or a pharmaceutically acceptable salt thereof according to claim 1, wherein two adjacent $R^1$ and two adjacent $R^2$ form a phenyl ring.

* * * * *